US006677349B1

(12) United States Patent
Griesgraber

(10) Patent No.: US 6,677,349 B1
(45) Date of Patent: Jan. 13, 2004

(54) SULFONAMIDE AND SULFAMIDE SUBSTITUTED IMIDAZOQUINOLINES

(75) Inventor: George W. Griesgraber, Eagan, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 0 days.

(21) Appl. No.: 10/425,054

(22) Filed: Apr. 28, 2003

Related U.S. Application Data

(63) Continuation of application No. 10/027,273, filed on Dec. 21, 2001, now abandoned.

(51) Int. Cl.[7] ............... A61K 31/4745; A61K 31/541; C07D 471/04; C07D 417/14; A61P 37/02
(52) U.S. Cl. ............... 514/293; 514/228.5; 514/253.03; 546/82; 544/60; 544/361; 544/364
(58) Field of Search ...................... 546/82; 514/293, 514/228.5, 253.03; 544/60, 361, 364

(56) References Cited

U.S. PATENT DOCUMENTS

| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 2002/0055517 A1 | 5/2002 | Smith |
| 2002/0058674 A1 | 5/2002 | Hedenstrom et al. |

FOREIGN PATENT DOCUMENTS

| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 00/47719 | 8/2000 |
| WO | WO 00/76518 | 12/2000 |
| WO | WO 01/74343 | 10/2001 |
| WO | WO 02/36592 | 5/2002 |
| WO | WO 02/46188 | 6/2002 |
| WO | WO 02/46189 | 6/2002 |
| WO | WO 02/46190 | 6/2002 |
| WO | WO 02/46191 | 6/2002 |
| WO | WO 02/46192 | 6/2002 |
| WO | WO 02/46193 | 6/2002 |
| WO | WO 02/46749 | 6/2002 |
| WO | WO 02/102377 | 12/2002 |
| WO | WO 03/020889 | 3/2003 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul. 78, 1983.

Testerman, et al., "Cytokine Induction by the Immunomodulators Imiquimod and S–27609", *Journal of Leukocyte Biology*, vol. 58, pp. 365–372, Sep. 1995.

Bachman, et al, "Synthesis of Substituted Quinolylamines. Derivatives of 4–Amino–7–Chloroquinoline" *J. Org. Chem*, 15, pp 1278–1284 (1950).

Jain, et al, "Chemical and Pharmacological Investigations of Some ω–Substituted Alkylamino–3–aminopyridines", *J. Med. Chem.*, 11, pp 87–92 (1968).

Baranov, et al., *Chem. Abs.* 85, 94371, (1976).

Berényi, et al, "Ring Transformation of Condensed Dihydro–as–triazines" ,*J. Heterocyclic Chem.*, 18, pp 1537–1540 (1981).

Chollet, et al, "Development of a Topically Active Imiquimod Formulation", *Pharmaceutical Development and Technology*, 4(1), pp 35–43 (1999).

*Primary Examiner*—Evelyn Mei Huang
(74) *Attorney, Agent, or Firm*—Dean A. Ersfeld

(57) ABSTRACT

Imidazoquinoline and tetrahydroimidazoquinoline compounds that contain sulfonamide or sulfamide functionality at the 1-position are useful as immune response modifiers. The compounds and compositions of the invention can induce the biosynthesis of various cytokines and are useful in the treatment of a variety of conditions including viral diseases and neoplastic diseases.

3 Claims, No Drawings

SULFONAMIDE AND SULFAMIDE SUBSTITUTED IMIDAZOQUINOLINES

CROSS REFERENCE TO RELATED APPLICATIONS

This application is a continuation of U.S. application Ser. No. 10/027273 filed on Dec. 21, 2001, now abandoned.

FIELD OF THE INVENTION

This invention relates to imidazoquinoline compounds that have sulfonamide or sulfamide substitution at the 1-position and to pharmaceutical compositions containing the compounds. A further aspect of this invention relates to the use of these compounds as immunomodulators, for inducing cytokine biosynthesis in animals and in the treatment of diseases including viral and neoplastic diseases.

BACKGROUND OF THE INVENTION

The first reliable report on the 1H-imidazo[4,5-c] quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl) ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system, as seen for example in WO 98/30562, EP 894 797 and WO 00/09506. EP 894 797 discloses amide substituted imidazoquinoline compounds that are disclosed to be useful as immune response modifying compounds, while WO 00/09506 discloses imidazoquinoline compounds that contain a sulfonamide substituent wherein the sulfonamide nitrogen is part of a saturated heterocyclic ring. Despite these efforts, however, there is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides compounds of Formula I:

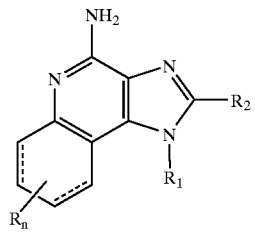

wherein R, $R_1$ and $R_2$ are as defined herein.

The compounds of Formula I are useful as immune response modifiers due to their ability to induce cytokine biosynthesis and otherwise modulate the immune reponse when administered to animals. This makes the compounds useful in the treatment of a variety of conditions such as viral diseases and tumors that are responsive to such changes in the immune response.

The invention further provides pharmaceutial compositions containing a therapeutically effective amount of a compound of Formula I and methods of inducing cytokine biosynthesis in an animal, treating a viral infection and/or treating a neoplastic disease in an animal by administering a effective amount of a compound of Formula I to the animal.

In addition, methods of synthesizing compounds of Formula I and intermediates useful in the synthesis of these compounds are provided.

DETAILED DESCRIPTION OF THE INVENTION

As mentioned earlier, the invention provides compounds of Formula I:

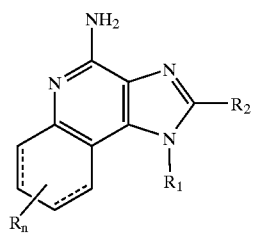

wherein
$R_1$ is -alkyl-$NR_3$—$SO_2$—X—$R_4$ or -alkenyl-$NR_3$—$SO_2$—X—$R_4$;
X is a bond or —$R_5$—;
$R_4$ is aryl, heteroaryl, heterocyclyl, alkyl or alkenyl, each of which may be unsubstituted or substituted by one or more substituents selected from the group consisting of:
-alkyl;
-alkenyl;
-aryl;
-heteroaryl;
-heterocyclyl;
-substituted aryl;
-substituted heteroaryl;
-substituted heterocyclyt;
-O-alkyl;
—O-(alkyl)$_{0-1}$-aryl;
—O-(alkyl)$_{0-1}$-substituted aryl;
—O-(alkyl)$_{0-1}$-heteroaryl;

—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-alkyl)$_{0-1}$-aryl;
—S(O)$_{0-2}$-alkyl)$_{0-1}$-substituted aryl;
—S(O)$_{0-2}$-alkyl)$_{0-1}$-heteroaryl;
—S(O)$_{0-2}$-alkyl)$_{0-1}$-substituted heteroaryl;
—S(O)$_{0-2}$-alkyl)$_{0-1}$-heterocyclyl;
—S(O)$_{0-2}$-alkyl)$_{0-1}$-substituted heterocyclyl;
-(alkyl)$_{0-1}$-R$_3$R$_3$;
-(alkyl)$_{0-1}$-NR$_3$—CO—O-alkyl;
-(alkyl)$_{0-1}$-NR$_3$—CO-alkyl;
-(alkyl)$_{0-1}$-NR$_3$—CO-aryl;
-(alkyl)$_{0-1}$-NR$_3$—CO-substituted aryl;
-(alkyl)$_{0-1}$-R$_3$—CO-heteroaryl;
-(alkyl)$_{0-1}$-R$_3$—CO-substituted heteroaryl;
—N$_3$;
-halogen;
-haloalkyl;
-haloalkoxy;
—CO-haloalkoxy;
—NO$_2$;
—CN;
—OH;
—SH; and in the case of alkyl alkenyl, or heterocyclyl, oxo;

R$_2$ is selected from the group consisting of:
  -hydrogen;
  -alkyl;
  -alkenyl;
  -aryl;
  -substituted aryl;
  -heteroaryl;
  -substituted heteroaryl;
  -alkyl-O-alkyl;
  -alkyl-O-alkenyl; and
  -alkyl or alkenyl substituted by one or more substituents selected from the group consisting of:
    —OH;
    -halogen;
    —N(R$_3$)$_2$;
    —CO—N(R$_3$)$_2$;
    —CO—C$_{1-10}$ alkyl;
    —CO—O—C$_{1-10}$ alkyl;
    —$_3$;
    -aryl;
    -substituted aryl;
    -heteroaryl;
    -substituted heteroaryl;
    -heterocyclyl;
    -substituted heterocyclyl;
    —CO-aryl;
    —CO-(substituted aryl);
    —CO-heteroaryl; and
    —CO-(substituted heteroaryl);
each R$_3$ is independently selected from the group consisting of hydrogen and C$_{1-10}$ alkyl;
R$_5$ is selected from the group consisting of hydrogen and C$_{1-10}$ alkyl, or R$_4$ and R$_5$ can combine to form a 3 to 7 membered heterocyclic or substituted heterocyclic ring;
n is 0 to 4 and each R present is independently selected from the group consisting of C$_{1-10}$ alkyl, C$_{1-10}$ alkoxy, halogen and trifluoromethyl, or a pharmaceutically acceptable salt thereof.

Preparation of the Compounds

Imidazoquinolines of the invention can be prepared according to Reaction Scheme I where R, R$_1$, R$_2$ and n are as defined above.

In step (1) of Reaction Scheme I a 4-chloro-3-nitroquinoline of Formula II is reacted with an amine of Formula R$_1$NH$_2$ where R$_1$ is as defined above to provide a 3-nitroquinolin-4-amine of Formula III. The reaction can be carried out by adding amine to a solution of a compound of Formula II in a suitable solvent such as chloroform or dichloromethane and optionally heating. Many quinolines of Formula II are known compounds (see for example, U.S. Pat. No. 4,689,338 and references cited therein).

In step (2) of Reaction Scheme I a 3-nitroquinolin-4-amine of Formnula III is reduced to provide a quinoline-3,4-diamine of Formula IV. Preferably, the reduction is carried out using a conventional heterogeneous hydrogenation catalyst such as platinum on carbon or palladium on carbon. The reaction can conveniently be carried out on a Parr apparatus in a suitable solvent such as isopropyl alcohol or toluene.

In step (3) of Reaction Scheme I a quinoline-3,4-diamine of Formula IV is reacted with a carboxylic acid or an equivalent thereof to provide a 1H-imidazo[4,5-c]quinoline of Formula V. Suitable equivalents to carboxylic acid include acid halides, orthoesters, and 1,1-dialkoxyalkyl alkanoates. The carboxylic acid or equivalent is selected such that it will provide the desired R$_2$ substituent in a compound of Formula V. For example, triethyl orthoformate will provide a compound where R$_2$ is hydrogen and triethyl orthoacetate will provide a compound where R$_2$ is methyl. The reaction can be run in the absence of solvent or in an inert solvent such as toluene. The reaction is run with sufficient heating to drive off any alcohol or water formed as a byproduct of the reaction.

In step (4) of Reaction Scheme I a 1H-imidazo[4,5-c]quinoline of Formula V is oxidized to provide a 1H-imidazo[4,5-c]quinoline-5N-oxide of Formula VI using a conventional oxidizing agent that is capable of forming N-oxides. Preferred reaction conditions involve reacting a solution of a compound of Formula V in chloroform with 3-chloroperoxybenzoic acid at ambient conditions.

In step (5) of Reaction Scheme I a 1H-imidazo[4,5-c]quinoline-5N-oxide of Formula VI is aminated to provide a 1H-imidazo[4,5-c]quinolin-4-amine of Formula VII which is a subgenus of Formula I. Step (5) involves (i) reacting a compound of Formula VI with an acylating agent and then (ii) reacting the product with an aminating agent. Part (i) of step (5) involves reacting an N-oxide of Formula VI with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (5) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula VI in an inert solvent such as dichloromethane, adding the aminating agent to the solution, and then slowly adding the acylating agent. The product or a pharmaceutically acceptable salt thereof can be isolated using conventional methods.

Alternatively, step (5) may be carried out by (i) reacting an N-oxide of Formula VI with an isocyanate and then (ii) hydrolyzing the resulting product. Part (i) involves reacting the N-oxide with an isocyanate wherein the isocyanato group is bonded to a carbonyl group. Preferred isocyanates include trichloroacetyl isocyanate and aroyl isocyanates such as benzoyl isocyanate. The reaction of the isocyanate with the N-oxide is carried out under substantially anhydrous conditions by adding the isocyanate to a solution of the N-oxide in an inert solvent such as chloroform or dichloromethane. Part (ii) involves hydrolysis of the product from part (i). The hydrolysis can be carried out by conventional methods such as heating in the presence of water or a lower alkanol optionally in the presence of a catalyst such as an alkali metal hydroxide or lower alkoxide.

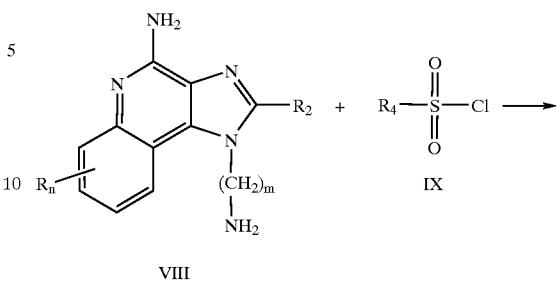

Reaction Scheme II

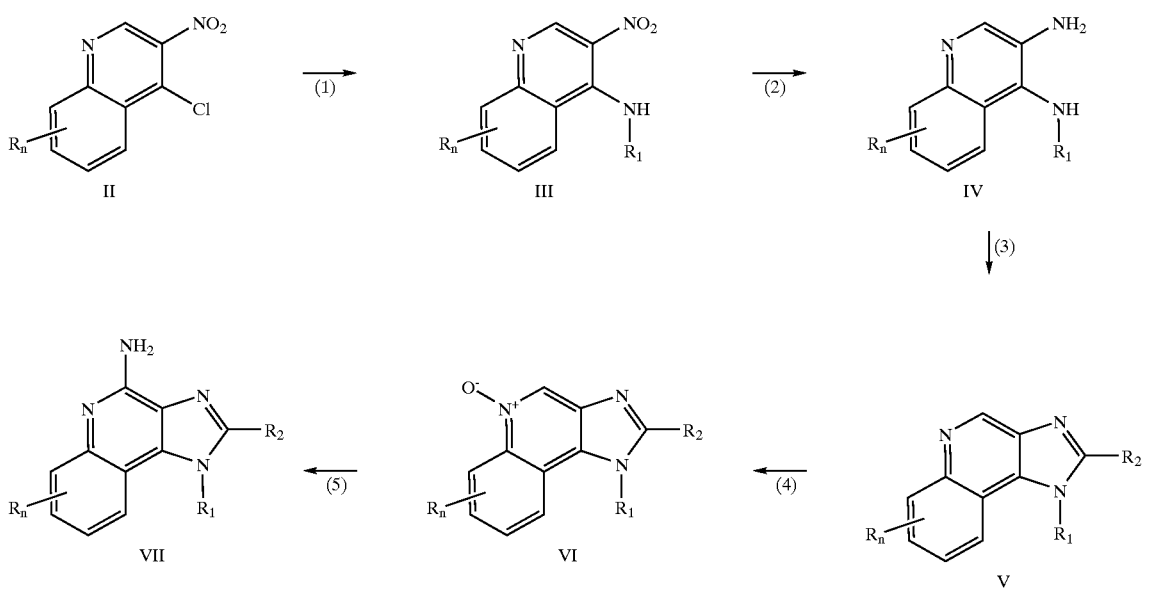

Reaction Scheme I

Compounds of the invention where the $R_1$ substituent contains a sulfonamide can also be prepared according to Reaction Scheme II where R, $R_2$, $R_4$ and n are as defined above and m is 1–20.

In Reaction Scheme II an aminoalkyl substituted 1H-imidazo[4,5-c]quinolin-4-amine of Formula VIII is reacted with a sulfonyl chloride of Formula IX to provide a compound of Formula X which is a subgenus of Formula I. The reaction can be run at ambient temperature in an inert solvent such as dichloromethane in the presence of a base such as pyridine or N,N-diisopropylethylamine. Many 1H-imidazo[4,5-c]quinolin-4-amines of Formula VIII are known compounds, see for example U.S. Pat. No. 6,069,149 (Namba); others can be readily prepared using known synthetic methods. Many sulfonyl chlorides of Formula IX are commercially available; others can be readily prepared using known synthetic methods. The product or a pharmaceutically acceptable salt thereof can be isolated using conventional methods.

-continued

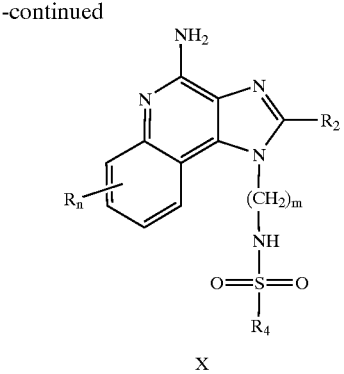

X

Compounds of the invention where the $R_1$ substituent contains a sulfonamide can also be prepared according to Reaction Scheme III where R, $R_2$, $R_4$ and n are as defined above and m is 1–20.

In Reaction Scheme III an aminoalkyl substituted 1H-imidazo[4,5-c]quinolin-4-amine of Formula VIII is reacted with a sulfonic anhydride of Formula XI to provide a compound of Formula X which is a subgenus of Formula I. The reaction can be run at ambient temperature in an inert solvent such as dichloromethane in the presence of a base such as pyridine or N,N-diisopropylethylamine. Alternatively, the reaction can be run at ambient temperature in acetonitrile. Many sulfonic anhydrides of Formula XI are commercially available; others can be readily prepared using known synthetic methods. The product or a pharmaceutically acceptable salt thereof can be isolated using conventional methods.

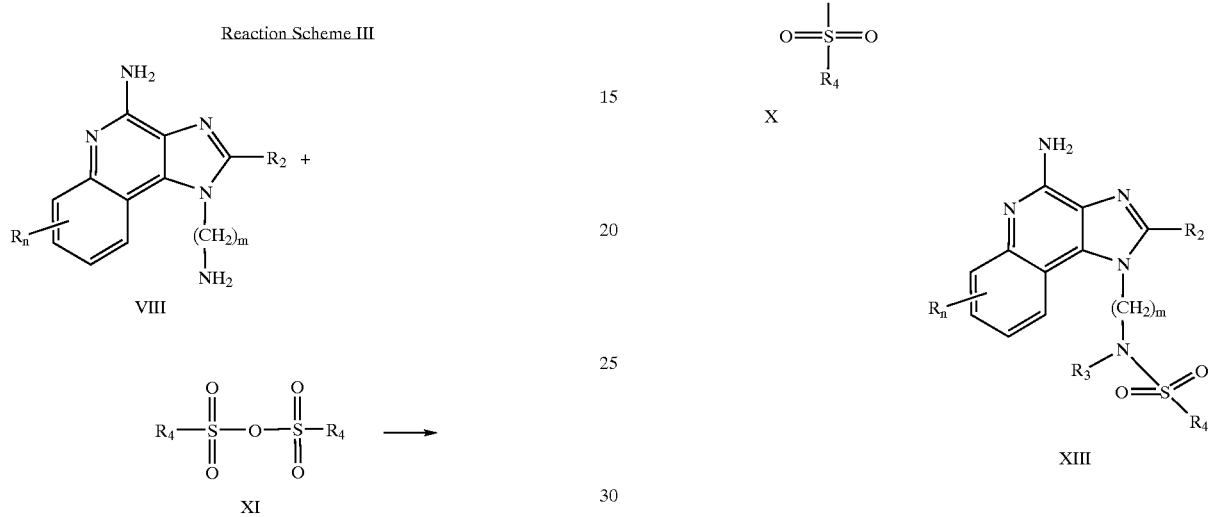

Tertiary sulfonamides of the invention can be prepared according to Reaction Scheme IV where R, $R_2$, $R_3$, $R_4$ and n are as defined above and m is 1–20.

In Reaction Scheme IV a 1H-imidazo[4,5-c]quinolinyl sulfonamide of Formula X is reacted with a halide of Formula XII to provide a compound of Formula XIII which is a subgenus of Formula I. The reaction can be carried out at ambient temperature by adding sodium hydride to a solution of a compound of Formula X in N,N-dimethylformamide and then adding the halide. Many halides of Formula XII are commercially available; others can be readily prepared using known synthetic methods. The product or a pharmaceutically acceptable salt thereof can be isolated using conventional methods.

Compounds of the invention where $R_1$ contains a sulfamide group can be prepared according to Reaction Scheme V wherein R, $R_2$, $R_4$, $R_5$ and n are as defined above and m is 1–20.

In step (1) of Reaction Scheme V an aminoalkyl substituted 1H-imidazo[4,5-c]quinolin-4-amine of Formula VIII is reacted with sulfuryl chloride to generate in situ a sulfamoyl chloride of Formula XIV. The reaction can be carried out by adding a solution of sulfuryl chloride in dichloromethane to a solution of a compound of Formula VIII in dichloromethane in the presence of one equivalent of 4-(dimethylamino)pyridine. The reaction is preferably carried out at a reduced temperature (−78° C.). Optionally, after the addition is complete the reaction mixture can be allowed to warm to ambient temperature.

In step (2) of Reaction Scheme V an amine of Formula $R_5R_4NH$ is reacted with the sulfamoyl chloride of Formula XIV to provide a 1H-imidazo[4,5-c]quinolinyl sulfamide of Formula XV which is a subgenus of Formula I. The reaction can be carried out by adding a solution containing 2 equivalents of the amine and 2 equivalents of triethylamine in dichloromethane to the reaction mixture from step (1). The addition is preferably carried out at a reduced temperature (−78° C.). After the addition is complete the reaction mixture can be allowed to warm to ambient temperature. The product or a pharmaceutically acceptable salt thereof can be isolated using conventional methods.

Reaction Scheme V

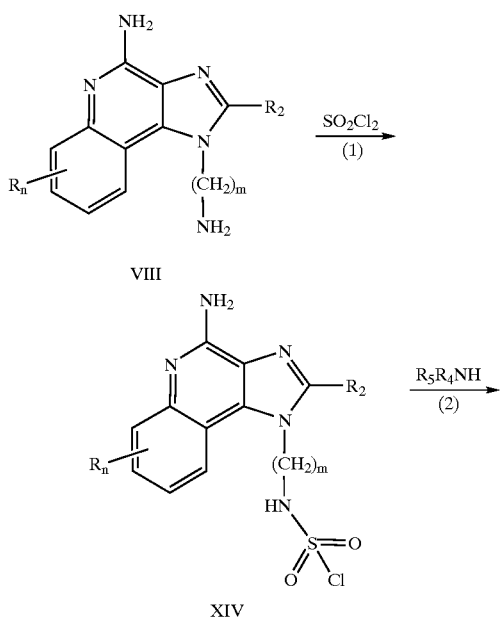

Tetrahydroimidazoquinolines of the invention can be prepared according to Reaction Scheme VI where $R_2$, $R_3$, $R_4$, and $R_5$ are as defined above and m is 1–20.

In step (I) of Reaction Scheme VI an aminoalkyl substituted 1H-imidazo[4,5-c]quinolin-4-amine of Formula XVI is reduced to provide an aminoalkyl substituted 6,7,8,9-tetrahydro-1H-imidazo[4,5-c]quinolin-4-amine of Formula XVII. Preferably the reduction is carried out by suspending or dissolving the compound of Formula XVI in trifluoroacetic acid, adding a catalytic amount of platinum (IV) oxide, and then subjecting the mixture to hydrogen pressure. The reaction can conveniently be carried out on a Parr apparatus. The product or a salt thereof can be isolated using conventional methods.

In step (2a) of Reaction Scheme VI an aminoalkyl substituted 6,7,8,9-tetrahydro-1H-imidazo[4,5-c]quinolin-4-amine of Formula XVII is reacted to provide a compound of Formula XVIII which is a subgenus of Formula I. When $R_3$ is hydrogen, the reaction can be carried out in one step according to the methods described in Reaction Schemes II and III above using a tetrahydroimidazoquinoline of Formula XVII in place of the imidazoquinoline of Formula VIII. When $R_3$ is other than hydrogen, the reaction can be carried out in two steps with step one being carried out according to the methods of Reaction Schemes II and III and step two being carried out according to the method of Reaction IV using the tetrahydroimidazoquinoline analog of the imidazoquinoline. The product or a pharmaceutically acceptable salt thereof can be isolated using conventional methods.

In step (2b) of Reaction Scheme VI an aminoalkyl substituted 6,7,8,9-tetrahydro-1H-imidazo[4,5-c]quinolin-4-amine of Formula XVII is reacted to provide a compound of Formula XIX which is a subgenus of Formula I. The reaction can be carried out according to the method described in Reaction Scheme V using a tetrahydroimidazoquinoline of Formula XVII in place of the imidazoquinoline of Formula VIII. The product or a pharmaceutically acceptable salt thereof can be isolated using conventional methods.

Reaction Scheme VI

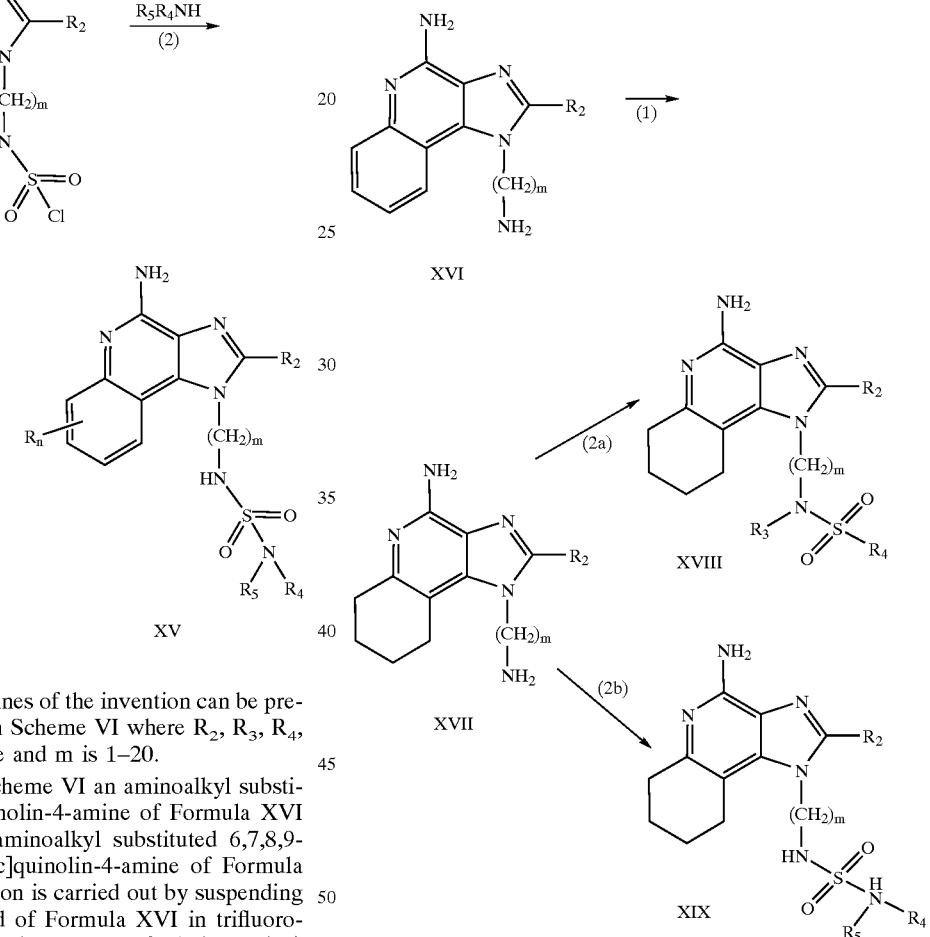

Tetrahydroimidazoquinolines of the invention can also be prepared according to Reaction Scheme VII where R, $R_2$, $R_3$, $R_4$, $R_5$ and n are as defined above and m is 1–20.

In step (1) of Reaction Scheme VII a 6,7,8,9-tetrahydro-1H-imidazo[4,5-c]quinolinyl tert-butylcarbamate of Formula XX is hydrolyzed to provide an aminoalkyl substituted 6,7,8,9-tetrahydro-1H-imidazo[4,5-c]quinolin-4-amine of Formula XXI. The reaction can be carried out dissolving the compound of Formula XX in a mixture of trifluoroacetic acid and acetonitrile and stirring at ambient temperature. Alternatively, the compound of Formula XX can be combined with dilute hydrochloric acid and heated on a steam bath. Tetrahydro-1H-imidazo[4,5-c]quinolinyl tert-butylcarbamates of Formula XX can be prepared using the synthetic route disclosed in U.S. Pat. No. 5,352,784 (Nikolaides). The product or a salt thereof can be isolated using conventional methods.

Steps (2a) and (2b) can be carried out in the same manner as in Reaction Scheme VI.

groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl and adamantyl.

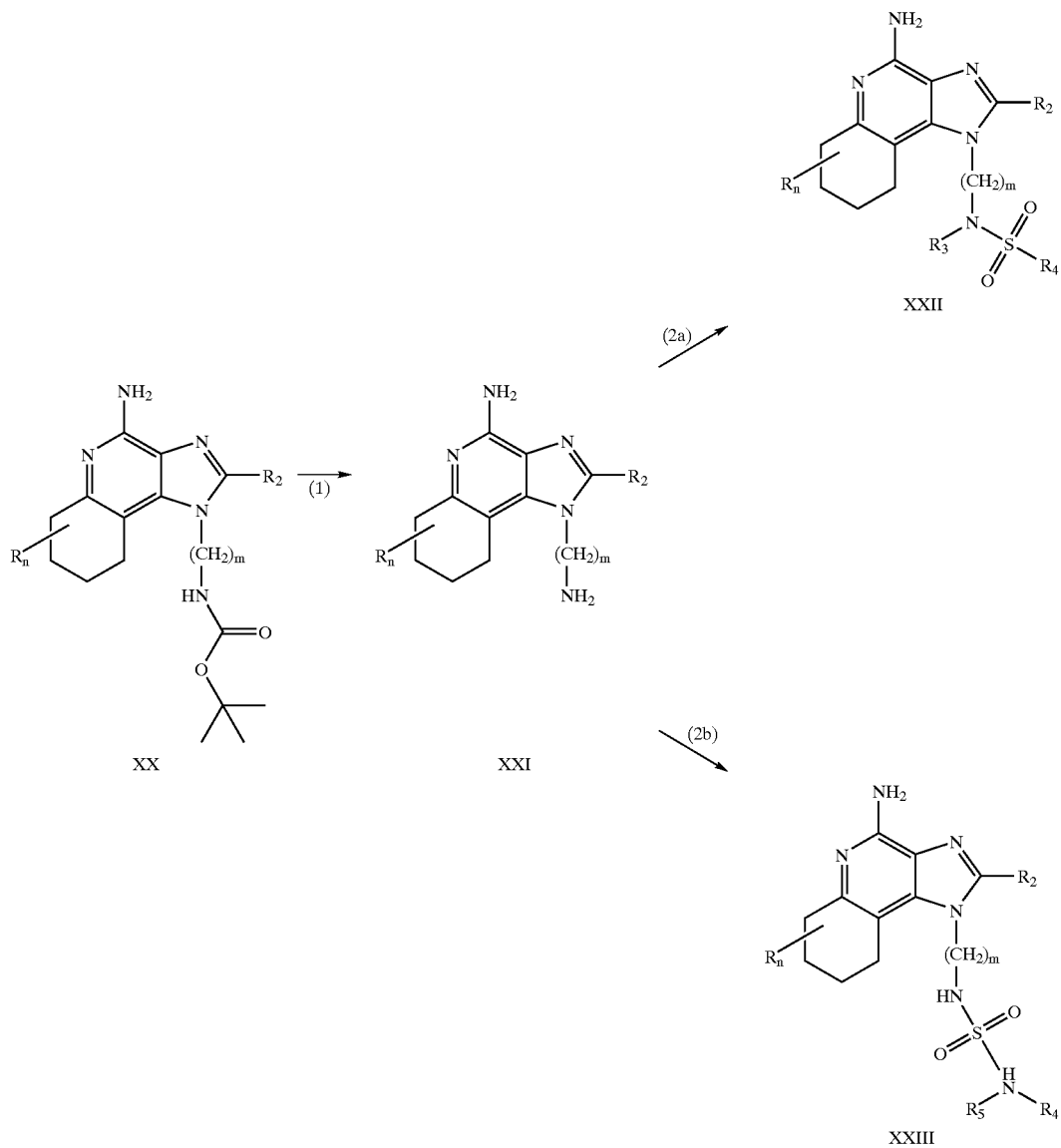

Some compounds of Formula I can be readily prepared from other compounds of Formula I. For example, compounds wherein the $R_4$ substituent contains a chloroalkyl group can be reacted with an amine to provide an $R_4$ substituent substituted by a secondary or teriary amino group; compounds wherein the $R_4$ substituent contains a nitro group can be reduced to provide a compound wherein the $R_4$ substituent contains a primary amine.

As used herein, the terms "alkyl", "alkenyl", "alkynyl" and the prefix "-alk" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl The term "haloalkyl" is inclusive of groups that are substituted by one or more halogen atoms, including groups wherein all of the available hydrogen atoms are replaced by halogen atoms. This is also true of groups that include the prefix "haloalk-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, tetrazolyl, imidazo, pyrazolo, thiazolo, oxazolo, and the like.

"Heterocyclyl" includes non-aromatic rings or ring systems that contain at least one ring hetero atom (e.g., O, S, N). Exemplary heterocyclic groups include pyrrolidinyl, tetrahydrofuranyl, morpholinyl, thiomorpholinyl, piperidinyl, piperazinyl, thiazolidinyl, imidazolidinyl, and the like.

Unless otherwise specified, the terms "substituted cycloalkyl", "substituted aryl", "substituted heteroaryl" and "substituted heterocyclyl" indicate that the rings or ring systems in question are further substituted by one or more substituents independently selected from the group consisting of alkyl, alkoxy, alkylthio, hydroxy, halogen, haloalkyl, haloalkylcarbonyl, haloalkoxy (e.g., trifluoromethoxy), nitro, alkylcarbonyl, alkenylcarbonyl, arylcarbonyl, heteroarylcarbonyl, aryl, arylalkyl, heteroaryl, heteroarylalkyl, heterocyclyl, heterocycloalkyl, nitrile, alkoxycarbonyl, alkanoyloxy, alkanoylthio, and in the case of cycloalkyl and heterocyclyl, oxo.

In structural formulas representing compounds of the invention certain bonds are represented by dashed lines. These lines mean that the bonds represented by the dashed line can be present or absent. Accordingly, compounds of Formula I can be either imidazoquinoline compounds or tetrahydroimidazoquinoline compounds.

The invention is inclusive of the compounds described herein in any of their pharmaceutically acceptable forms, including isomers such as diastereomers and enantiomers, salts, solvates, polymorphs, and the like.

Pharmnaceutical Compositions and Biological Activity

Pharmaceutical compositions of the invention contain a therapeutically effective amount of a compound of Formula I in combination with a pharmaceutically acceptable carrier.

As used herein, the term "a therapeutically effective amount" means an amount of the compound sufficient to induce a therapeutic effect, such as cytokine induction, antitumor activity and/or antiviral activity. Although the exact amount of active compound used in a pharmaceutical composition of the invention will vary according to factors known to those of skill in the art, such as the physical and chemical nature of the compound as well as the nature of the carrier and the intended dosing regimen, it is anticipated that the compositions of the invention will contain sufficient active ingredient to provide a dose of about 100 ng/kg to about 50 mg/kg, preferably about 10 µg/kg to about 5 mg/kg of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines that may be induced by the administration of compounds according to the invention generally include interferon-α (IFN-α) and tumor necrosis factor-α (TNF-α) as well as certain interleukins (IL). Cytokines whose biosynthesis may be induced by compounds of the invention include IFN-α, TNF-α, IL-1, 6, 10 and 12, and a variety of other cytokines. Among other effects, cytokines inhibit virus production and tumor cell growth, making the compounds useful in the treatment of viral diseases and tumors.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of Formula Ia to inhibit the Th2 immune response, the compounds are expected to be useful in the treatment of atopic diseases, e.g., atopic dermatitis, asthma, allergy, and allergic rhinitis; and systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such as, but not limited to, viral diseases including genital warts; common warts; plantar warts; Hepatitis B; Hepatitis C; Herpes Simplex Virus Type I and Type II; molluscum contagiosum; HIV; CMV; VZV; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma, melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, leishmaniasis; and bacterial infections, e.g., tuberculosis, mycobacterium avium. Additional diseases or conditions that can be treated using the compounds of the invention include eczema; eosinophilia; essential thrombocythaemia; leprosy; multiple sclerosis; Ommen's syndrome; discoid lupus; Bowen's disease; Bowenoid papulosis; and to enhance or stimulate the healing of wounds, including chronic wounds.

Accordingly, the invention provides a method of inducing cytokine biosynthesis in an animal comprising administering an effective amount of a compound of Formula I to the animal. An amount of a compound effective to induce cytokine biosynthesis is an amount sufficient to cause one or more cell types, such as monocytes, macrophages, dendritic cells and B-cells to produce an amount of one or more cytokines such as, for example, IFN-<, TNF-<, IL-1,6,10 and 12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal, and a method of treating a neoplastic disease in an animal, comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

EXAMPLE 1

$N^1$-[4-(4-Amino-2-butyl-1H-imidazo[4,5-c]quinolin-1-yl)butyl]-5-(dimethylamino)-1-naphthalenesulfonamide

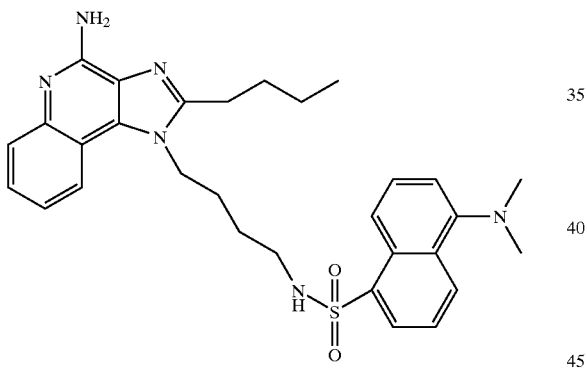

5-Dimethylamino-1-naphthalenesulfonyl chloride (1.82 g, 6.74 mmol) was added to a mixture of N,N-diisopropylethylamine (1.23 mL, 7.06 mmol), dichloromethane (15 mL) and 1-(4-aminobutyl)-2-butyl-1H-imidazo[4,5-c]quinolin-4-amine (2.0 g, 6.42 mmol). The reaction mixture was allowed to stir at ambient temperature overnight. Methanol was added to the reaction mixture until a clear solution was obtained. Silica gel was added to the reaction mixture and then the solvents were removed. The silica gel was placed in a column and then eluted with chloroform in a stepwise gradient to 9:1 chloroform:methanol. The resulting product was recrystallized from N,N-dimethylformamide and deionized water to provide 2.5 g of $N^1$-[4-(4-amino-2-butyl-1H-imidazo[4,5-c]quinolin-1-yl)butyl]-5-(dimethylamino)-1-naphthalenesulfonamide as a yellow crystalline solid, m.p. 223–224° C. Analysis: Calculated for $C_{30}H_{36}N_6O_2S$: %C, 66.15; %H, 6.66; %N, 15.43; Found: %C, 66.36; %H, 6.34; %N, 15.23.

EXAMPLE 2

$N^1$-[4-(4-Amino-1H-imidazo[4,5-c]quinolin-1-yl)butyl]-5-(dimethylamino)-1-naphthalenesulfonamide

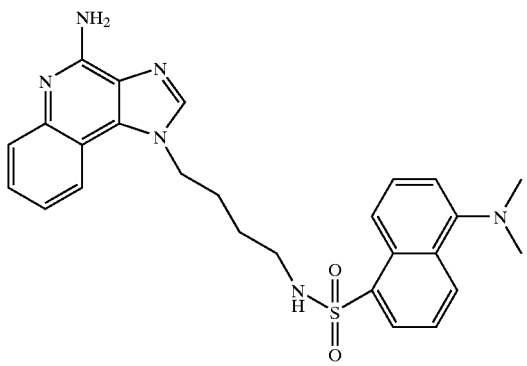

A suspension of 1-(4-aminobutyl)-1H-imidazo[4,5-c]quinolin-4-amine (0.5 g, 2.0 mmol) in pyridine (250 mL) was warmed to 60° C. to dissolve the amine. The solution was allowed to cool to about 30° C. and then 5-dimethylamino-1-naphthalenesulfonyl chloride (0.5 g, 1.8 mmol) was slowly added. After 1 hour 0.3 g of 5-dimethylamino-1-naphthalenesulfonyl chloride was added. The reaction mixture was warmed to 60° C. and maintained at that temperature overnight. The reaction mixture was concentrated under vacuum. The residue was recrystallized from propyl acetate to provide $N^1$-[4-(4-amino-1H-imidazo[4,5-c]quinolin-1-yl)butyl]-5-(dimethylamino)-1-naphthalenesulfonamide as a solid, m.p. 200–201° C.

EXAMPLE 3

$N^2$-[4-(4-Amino-2-butyl-1H-imidazo[4,5-c]quinolin-1-yl)butyl]-2-thiophenesulfonamide

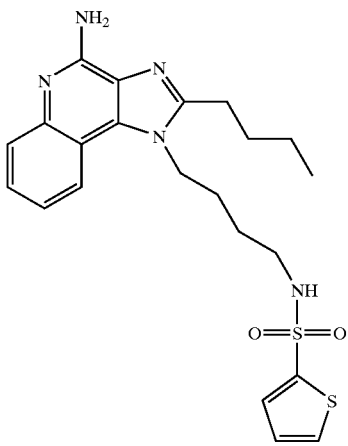

2-Thiophenesulfonyl chloride (0.3 g in 10 ml dichloromethane, 1.6 mmol) was added dropwise to a stirring solution of 1-(4-aminobutyl)-2-butyl-1H-imidazo[4,5-c]quinoline-4-amine (0.5 g, 1.6 mmol), dichloromethane (40 ml), and pyridine (0.8 ml). The reaction was maintained at room temperature for a few hours and then an additional portion of 2-thiophenesulfonyl chloride (0.1 g, 0.6 mmol) was added. The reaction was maintained overnight and then concentrated in vacuo. The resulting residue was purified by flash column chromatography (silica gel, 9:1 dichloromethanemethanol) and the fractions containing product were washed with saturated aqueous sodium bicarbonate. The organic layer was dried (MgSO$_4$), filtered, and concentrated to provide 0.2 g of $N^2$-[4-(4-amino-2-butyl-1H-imidazo[4,5-c]quinolin-1-yl)butyl]-2-thiophenesulfonamide as an off white powder, m.p. 137.5–141.5° C. $^1$H NMR (300 MHz, DMSO-d$_6$) δ 8.00 (d, J=8.0 Hz, 1H), 7.89 (dd, J=5.0, 1.3 Hz, 1H), 7.83 (broad s, 1H), 7.61 (dd, J=8.3, 1.1 Hz, 1H), 7.54 (dd, J=3.7, 1.3 Hz, 1H), 7.42 (t, J=7.2 Hz, 1H), 7.25 (m, 1H), 7.15 (m, 1H), 6.44 (broad s, 2H), 4.47 (t, J=7.4 Hz, 2H), 2.87 (m, 4H), 1.80 (m, 4H), 1.58–1.38 (m, 4H), 0.96 (t, J=7.4 Hz, 3H); IR (KBr) 3467, 3361, 3167, 3091, 2957, 2933, 2870, 1644, 1617, 1585, 1533, 1478, 1405, 1336, 1154, 1095, 1014, 854, 761, 733 cm$^{-1}$; MS (EI) m/e 457.1606 (457.1606 calcd for C$_{22}$H$_{27}$N$_5$O$_2$S$_2$); Anal calcd for C$_{22}$H$_{27}$N$_5$O$_2$S$_2$: C, 57.74; H, 5.95; N, 15.30. Found: C, 57.50; H, 5.98; N, 15.15.

EXAMPLE 4

N-[4-(4-Amino-2-butyl-1H-imidazo[4,5-c]quinolin-1-yl)butyl]phenylmethanesulfonamide

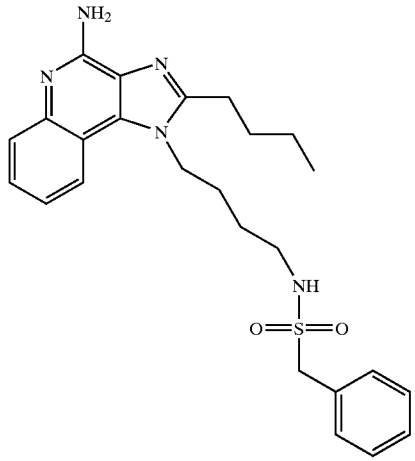

α-Toluenesulfonyl chloride (0.5 g in 10 ml dichloromethane, 2.7 mmol) was added dropwise to a stirring solution of 1-(4-aminobutyl)-2-butyl-1H-imidazo[4,5-c]quinoline-4-amine (0.75 g, 2.4 mmol), dichloromethane (115 ml), and pyridine (1 ml). The reaction was maintained at room temperature for 4 hours and then concentrated in vacuo. The residue was purified by flash column chromatography (silica gel, 9:1 dichloromethanemethanol, Rf 0.16). The fractions containing product were combined and washed with saturated aqueous bicarbonate. The organic layer was dried (MgSO4), filtered, and concentrated. A final recrystallization from dichloromethanediethyl ether provided 0.65 g of N-[4-(4-amino-2-butyl-1H-imidazo[4,5-c]quinolin-1-yl)butyl]phenylmethanesulfonamide as a white crystalline solid, m.p. 197.0–199.5° C. $^1$H NMR (300 MHz, DMSO-d$_6$) δ 8.02 (d, J=7.6 Hz, 1H), 7.62 (dd, J=8.3, 1.1 Hz, 1H), 7.42 (dt, J=7.5, 1.1 Hz, 1H), 7.35–7.23 (m, 7H), 7.12 (t, J=5.4 Hz, 1H), 6.46 (broad s, 2H), 4.49 (t, J=7.5 Hz, 2H), 4.29 (s, 2H), 2.91 (m, 4H), 1.83–1.42 (m, 8H), 0.96 (t, J=7.4 Hz 3H); IR (KBr) 3460, 3293, 3226, 3158, 2955, 2931, 2867, 1632, 1586, 1534, 1482, 1437, 1389, 1331, 1152, 1094, 752, 700 cm$^{-1}$; MS (EI) m/e 465.2204 (465.2198 calcd for C$_{25}$H$_{31}$N$_5$O$_2$S); Anal calcd for C$_{25}$H$_{31}$N$_5$O$_2$S: C, 64.49; H, 6.71; N, 15.04. Found: C, 64.15; H, 6.71; N, 15.00.

EXAMPLE 5

$N^1$-[4-(4-Amino-2-butyl-1H-imidazo[4,5-c]quinolin-1-yl)butyl]-1-benzenesulfonamide

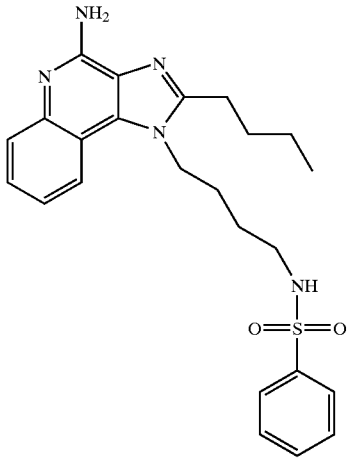

Benzenesulfonyl chloride (0.45 ml in 10 ml dichloromethane, 3.5 mmol) was added dropwise to a stirring solution of 1-(4-aminobutyl)-2-butyl-1H-imidazo[4,5-c]quinoline-4-amine (1.0 g, 3.2 mmol), dichloromethane (140 ml), and pyridine (0.8 ml). The reaction was maintained at room temperature for four hours and then concentrated in vacuo. The residue was purified by flash column chromatography (silica gel, 9:1 dichloro\methanemethanol, R$_f$ 0.28) followed by recrystallization from dichloro\methanediethyl ether to provide 1.14 g of $N^1$-[4-(4-amino-2-butyl-1H-imidazo[4,5-c]quinolin-1-yl)butyl]-1-benzenesulfonamide as a white powder, m.p. 75.5–79.0° C. $^1$H NMR (500 MHz, DMSO-d$_6$) δ 7.99 (d, J=7.7 Hz, 1H), 7.76 (d, J=7.2, 2H), 7.63–7.53 (m, 5H), 7.42 (m, 1H), 7.25 (m, 1H), 6.43 (broad s, 2H), 4.45 (t, J=7.6 Hz, 2H), 2.87 (t, J=7.7 Hz, 2H), 2.78 (m, 2H), 1.79 (m, 4H), 1.55–1.40 (m, 4H), 0.95 (t, J=7.4 Hz, 3H); MS (EI) m/e 451.2036 (451.2042 calcd for C$_{24}$H$_{29}$N$_5$O$_2$S); Anal calcd for C$_{24}$H$_{29}$N$_5$O$_2$S: C, 63.83; H, 6.47; N, 15.51. Found: C, 63.89; H, 6.42; N, 15.30.

EXAMPLE 6

N-[4-(4-Amino-2-butyl-1H-imidazo[4,5-c]quinolin-1-yl)butyl]methanesulfonamide

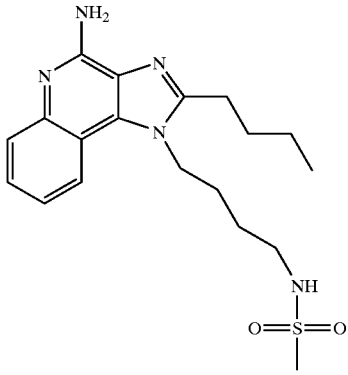

Methanesulfonic anhydride (0.6 g, 3.4 mmol) was added dropwise to a stirring solution of 1-(4-aminobutyl)-2-butyl- 1H-imidazo[4,5-c]quinoline-4-amine (1.0 g, 3.2 mmol) and acetonitrile (200 ml). A precipitate formed within a few minutes. The solvent was removed in vacuo and the residue was partitioned between dichloromethane and saturated aqueous sodium bicarbonate. The fractions were separated and the organic fraction was dried ($MgSO_4$), filtered and concentrated to yield the crude product as a white solid. Recrystallization from methyl acetate provided N-[4-(4-amino-2-butyl-1H-imidazo[4,5-c]quinolin-1-yl)butyl] methanesulfonamide as a white crystalline solid, m.p. 195.1–196.0° C. $^1$H NMR (300 MHz, DMSO-$d_6$) δ 8.04 (d, J=7.4 Hz, 1H), 7.61 (dd, J=8.3, 1.2 Hz, 1H), 7.50 (dt, J=7.5, 1.1 Hz, 1H), 7.26 (dt, J=7.5, 1.2 Hz, 1H), 6.99 (t, J'5.7 Hz, 1H), 6.44 (broad s, 2H), 4.52 (t, J=7.5 Hz, 2H), 3.02–2.86 (m, 7H), 1.82 (m, 4H), 1.62 (m, 2H), 1.46 (q, J=7.4 Hz, 2H), 0.96 (t, J=7.4 Hz, 3H); IR (KBr) 3348, 3299, 3152, 2952, 2931, 2869, 1642, 1584, 1530, 1480, 1323, 1155, 1142, 1094, 982, 765 cm$^{-1}$; MS (EI) m/e 389.1889 (389.1885 calcd for $C_{19}H_{27}N_5O_2S$); Anal calcd for $C_{19}H_{27}N_5O_2S$: C, 58.59; H, 6.99; N, 17.98. Found: C, 58.26; H, 6.64; N, 17.69.

EXAMPLE 7

$N^1$-[4-(4-Amino-2-butyl-1H-imidazo[4,5-c]quinolin-1-yl)butyl]-3-nitro-1-benzenesulfonamide Hydrochloride

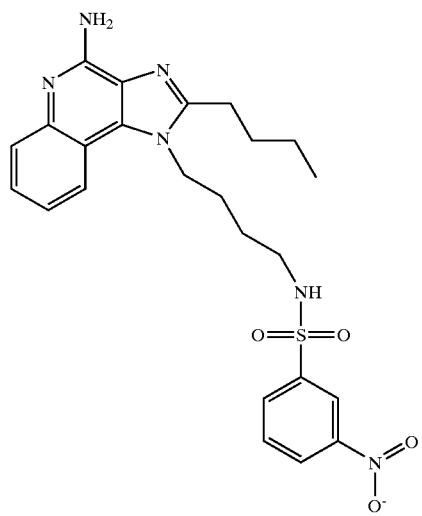

According to the general method of Example 5, 3-nitrobenzenesulfonyl chloride and 1-(4-aminobutyl)-2-butyl-1H-imidazo[4,5-c]quinoline-4-amine were combined. $N^1$-[4-(4-Amino-2-butyl-1H-imidazo[4,5-c]quinolin-1-yl)butyl]-3-nitro-1-benzenesulfonamide was isolated as the hydrochloride salt (white solid), m.p. 176.0–178.2° C. $^1$H NMR (300 MHz, DMSO-$d_6$) δ 8.70 (very broad s, 2H), 8.49–8.42 (m, 2H), 8.21–8.17 (m, 2H), 8.06 (t, J=5.7 Hz, 1H), 7.88–7.81 (m, 2H), 7.71 (t, J=7.7 Hz, 1H), 7.57 (t, J=7.7 Hz, 1H), 4.56 (t, J=7.3 Hz, 2H), 2.94 (t, J=7.7 Hz, 2H), 2.86 (m, 2H), 1.81 (m, 4H), 1.60–1.42 (m, 4H), 0.96 (t, J=7.3 Hz, 3H); IR (KBr) 3096, 2954, 2869, 2771, 1671, 1607, 1528, 1351, 1335, 1163, 1128, 1083, 879, 758, 735, 672, 661 cm$^{-1}$; MS (EI) m/e 496.1897 (496.1893 calcd for $C_{24}H_{28}N_6O_4S$). Anal calcd for $C_{24}H_{28}N_6O_4S$*HCl*$H_2O$: C, 52.31; H, 5.67; N, 15.25. Found: C, 52.26; H, 5.46; N, 15.09.

EXAMPLE 8

$N^1$-[4-(4-Amino-2-butyl-1H-imidazo[4,5-c]quinolin-1-yl)butyl]-3-amino-1-benzenesulfonamide Hydrochloride

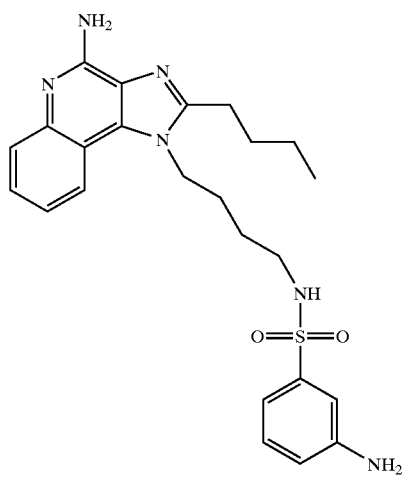

A solution of $N^1$-[4-(4-amino-2-butyl-1H-imidazo[4,5-c]quinolin-1-yl)butyl]-3-nitro-1-benzenesulfonamide hydrochloride (0.4 g) in methanol (250 ml) was charged with a catalytic amount of 10% palladium on carbon (0.085 g). The reaction was placed under an atmosphere of hydrogen (50 psi; 3.44×10$^5$ Pa) and shaken on a Parr apparatus for 2 hours. The reaction mixture was filtered and the solvent removed in vacuo. The solid product was recrystallized from 2-propanol to provide 0.18 g of $N^1$-[4-(4-amino-2-butyl-1H-imidazo[4,5-c]quinolin-1-yl)butyl]-3-amino-1-benzenesulfonamide hydrochloride as an off white crystalline solid, m.p. 110.2° C. (decomposition). $^1$H NMR (300 MHz, DMSO-$d_6$) δ 8.70 (very broad s, 2H), 8.22 (d, J=8.2 Hz, 1H), 7.83 (d, J=7.8 Hz, 1H), 7.72 (t, J=7.6 Hz, 1H), 7.59 (t, J=7.7 Hz, 1H), 7.43 (t, J=5.9 Hz, 1H), 7.15 (t, J=7.9 Hz, 1H), 6.95 (t, J=1.9 Hz, 1H), 6.84 (d, J=7.7 Hz, 1H), 6.73 (dd, J=8.0, 1.5 Hz, 1H), 5.63 (broad s, 2H), 4.56 (t, J=7.5 Hz, 2H), 2.96 (t, J=7.7 Hz, 2H), 2.77 (q, J=6.3 Hz, 2H), 1.83 (m, 4H), 1.60–1.40 (m, 4H), 0.97 (t, J=7.3 Hz, 3H); IR (KBr) 3313, 3135, 2957, 2870, 2782, 1671, 1599, 1485, 1454, 1313, 1155, 1084, 754, 686 cm$^{-1}$; MS (EI) m/e 466.2150 (466.2151 calcd for $C_{24}H_{30}N_6O_2S$). Anal calcd for $C_{24}H_{30}N_6O_2S$*HCl*0.25$H_2O$: C, 56.79; H, 6.26; N, 16.56; Cl, 6.98. Found: C, 56.87; H, 6.22; N, 16.19; Cl, 7.22.

EXAMPLE 9
N¹-[4-(4-Amino-2-butyl-1H-imidazo[4,5-c]quinolin-1-yl)butyl]-4-nitro-1-benzenesulfonamide Hydrochloride

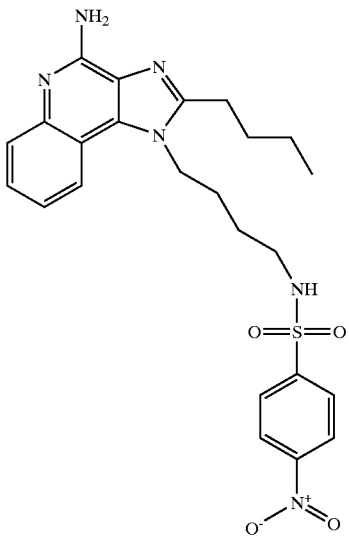

According to the general method of Example 5, 4-nitrobenzenesulfonyl chloride and 1-(4-aminobutyl)-2-butyl-1H-imidazo[4,5-c]quinoline-4-amine were combined. N¹-[4-(4-Amino-2-butyl-1H-imidazo[4,5-c]quinolin-1-yl)butyl]-4-nitro-1-benzenesulfonamide was isolated as the hydrochloride salt (white solid), m.p. 96.0° C. (decomposition). $^1$H NMR (300 MHz, DMSO-$d_6$) δ 8.70 (very broad s, 2H), 8.38–8.34 (m, 2H), 8.19 (d, J=8.2 Hz, 1H), 8.09 (t, J=5.6 Hz, 1H), 8.03–7.99 (m, 2H), 7.80 (d, J=7.4 Hz, 1H), 7.68 (t, J=7.4 Hz, 1H), 7.54 (t, J=7.2 Hz, 1H), 4.55 (t, J=7.4 Hz, 2H), 2.94 (t, J=7.7 Hz, 2H), 2.86 (q, J=6.2 Hz, 2H), 1.80 (m, 4H), 1.58 (m, 2H), 1.45 (q, J=7.5 Hz, 2H), 0.96 (t, J=7.3 Hz, 3H); IR (KBr) 3283, 3100, 2957, 2870, 2782, 1670, 1606, 1528, 1347, 1311, 1162, 1092, 854, 746, 737, 686 cm$^{-1}$; MS (EI) m/e 496.1902 (496.1893 calcd for $C_{24}H_{28}N_6O_4S$). Anal calcd for $C_{24}H_{28}N_6O_4S$*HCl*0.85H$_2$O: C, 52.57; H, 5.64; N, 15.33. Found: C, 52.57; H, 5.46; N, 15.33.

EXAMPLE 10
N¹-[4-(4-Amino-2-butyl-1H-imidazo[4,5-c]quinolin-1-yl)butyl]-4-amino-1-benzenesulfonamide Hydrochloride

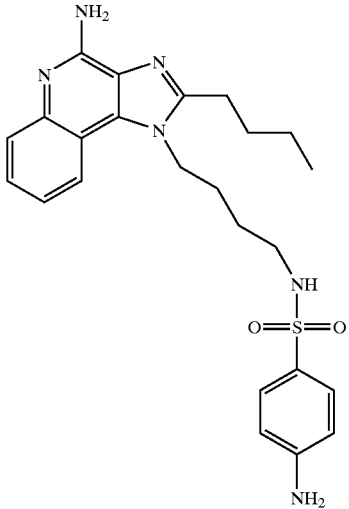

A solution of N¹-[4-(4-amino-2-butyl-1H-imidazo[4,5-c]quinolin-1-yl)butyl]-4-nitro-1-benzenesulfonamide hydrochloride (0.38 g) in methanol (250 ml) was charged with a catalytic amount of 10% palladium on carbon (0.085 g). The reaction was placed under an atmosphere of hydrogen (50 psi; 3.44×10⁵ Pa)) and shaken on a Parr apparatus for 2 hours. The reaction mixture was filtered and the solvent removed in vacuo. The solid product was recrystallized from 2-propanol to provide 0.34 g of N¹-[4-(4-amino-2-butyl-1H-imidazo[4,5-c]quinolin-1-yl)butyl]-4-amino-1-benzenesulfonamide hydrochloride as an off white powder, m.p. 203.1–205.0° C. $^1$H NMR (300 MHz, DMSO-$d_6$) δ 8.65 (very broad s, 2H), 8.21(d, J=8.0 Hz, 1H), 7.82 (m, 1H), 7.71 (t, J=7.7 Hz, 1H), 7.58 (t, J=7.7 Hz, 1H), 7.38 (d, J=8.7 Hz, 2H), 7.13 (t, J=5.9 Hz, 1H), 6.60 (d, J=8.7 Hz, 2H), 5.92 (broad s, 2H), 4.55 (t, J=7.6 Hz, 2H), 2.96 (t, J=7.6 Hz, 2H), 2.70 (q, J=6.4 Hz, 2H), 1.81 (m, 4H), 1.58–1.43 (m, 4H), 0.96 (t, J=7.4 Hz, 3H); IR (KBr) 3430, 3316, 3215, 3046, 2955, 2868, 2679, 1671, 1594, 1334, 1157, 1091, 851, 776, 759 cm$^{-1}$; MS (EI) m/e 466.2145 (466.2151 calcd for $C_{24}H_{30}N_6O_2S$). Anal calcd for $C_{24}H_{30}N_6O_2S$*HCl: C, 57.30; H, 6.21; N, 16.71. Found: C, 57.36; H, 6.31; N, 16.21.

EXAMPLE 11
N⁵-[4-(4-Amino-2-butyl-1H-imidazo[4,5-c]quinolin-1-yl)butyl]-5-isoquinolinesulfonamide

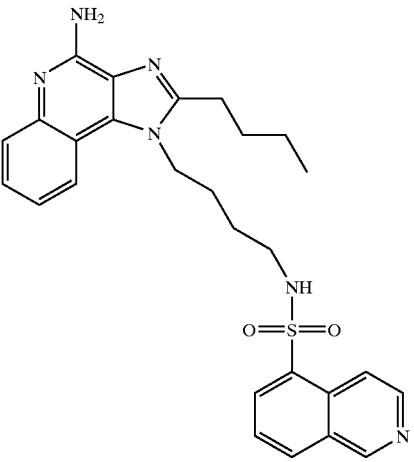

A suspension of isoquinoline-5-sulfonyl chloride hydrochloride (0.83 g in 50 ml of pyridine, 3.1 mmol) was added dropwise to a stirring solution of 1-(4-aminobutyl)-2-butyl-1H-imidazo[4,5-c]quinoline-4-amine (1.0 g, 3.2 mmol) and dichloromethane (175 ml). The solution turned a bright yellow color and was maintained at room temperature for 4 hours. An additional 0.18 g of isoquinoline-5-sulfonyl chloride hydrochloride was added and the reaction was maintained an additional 60 hours. The yellow solution was concentrated in vacuo, dissolved in dichloromethane, and washed sequentially with saturated aqueous sodium bicarbonate and water. The organic fraction was dried (MgSO$_4$), filtered, and concentrated in vacuo. The residue was purified by flash column chromatography (silica gel, 9:1 dichloromethanemethanol) to provide 0.7 g of N⁵-[4-(4-amino-2-butyl-1H-imidazo[4,5-c]quinolin-1-yl)butyl]-5-isoquinolinesulfonamide as a white crystalline solid, m.p. 96.0° C. (decomposition). $^1$H NMR (300 MHz, DMSO-$d_6$) δ 9.44 (d, J=0.7 Hz, 1H), 8.64 (d, J=6.1 Hz, 1H), 8.41–8.35 (m, 2H), 8.30 (dd, J=7.4, 1.2 Hz, 1H), 8.11 (t, J=5.6 Hz, 1H), 7.92 (d, J=7.6 Hz, 1H), 7.75 (t, J=7.7 Hz, 1H), 7.61 (dd, J=8.3, 1.2 Hz, 1H), 7.41 (dt, J=7.7, 1.2 Hz, 1H), 7.22 (dt, J=7.6, 1.2 Hz, 1H), 6.47 (broad s, 2H), 4.38 (t, J=7.5 Hz, 2H), 2.86–2.74 (m, 4H), 1.78–1.63 (m, 4H), 1.50–1.34 (m, 4H), 0.94 (t, J=7.4 Hz, 3H); MS (EI) m/e 502.2151 (502.2151 calcd for $C_{27}H_{30}N_6O_2S$). Anal calcd for $C_{27}H_{30}N_6O_2S$: C, 64.52; H, 6.02; N, 16.72. Found: C, 64.03; H, 6.03; N, 16.55.

EXAMPLE 12

N-[4-(4-Amino-2-(4-methoxybenzyl)-1H-imidazo[4,5-c]quinolin-1-yl]butyl]methanesulfonamide

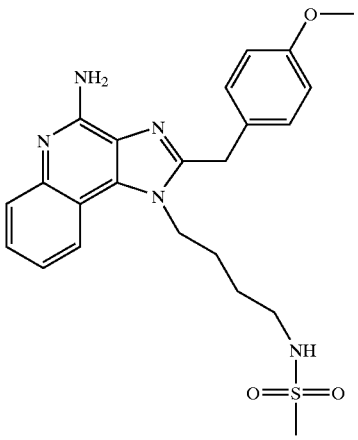

Methanesulfonic anhydride (0.19 g, 1.1 mmol) was added to a stirring solution of 1-(4-aminobutyl)-2-(4-methoxybenzyl)-1H-imidazo[4,5-c]quinolin-4-amine (0.4 g, 1.07 mmol), dichloromethane (75 ml) and acetonitrile (100 ml). The reaction was maintained at room temperature for 60 hours. The solvent was removed in vacuo and the residue was purified by flash column chromatography (silica gel, 9:1 dichloromethanemethanol). The fractions containing product were combined, washed with saturated aqueous sodium bicarbonate, dried (MgSO$_4$), filtered, and concentrated to provide 0.3 g of N-[4-(4-amino-2-(4-methoxybenzyl)-1H-imidazo[4,5-c]quinolin-1-yl]butyl]methanesulfonamide as a white solid, m.p. 78.1–79.5° C. $^1$H NMR (300 MHz, DMSO-d$_6$) δ 7.99 (d, J=7.6 Hz, 1H), 7.62 (dd, J=8.3, 1.2 Hz, 1H), 7.42 (m, 1H), 7.27–7.21 (m, 3H), 6.98 (t, J=5.7 Hz, 1H), 6.89 (d, J=8.7 Hz, 2H), 6.58 (broad s, 2H), 4.45 (broad s, 2H), 4.33 (s, 2H), 3.72 (s, 3H), 2.87 (m, 5H), 1.55 (broad s, 2H); MS (CI) m/e 454 (M+H).

EXAMPLE 13

N$^1$-[4-(4-Amino-1H-imidazo[4,5-c]quinolin-1-y)butyl]-1-butanesulfonamide

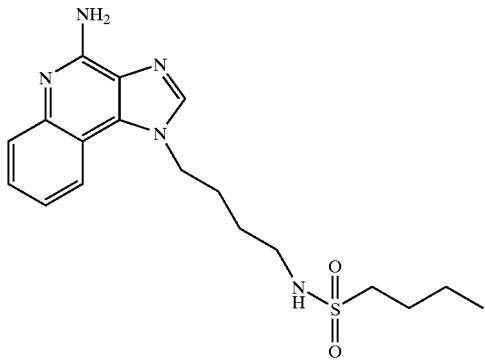

A solution of 1-(4-aminobutyl)-1H-imidazo[4,5-c]quinolin-4-amine (9.3 mg, 36 μmol) in 10 mL of dichloromethane in a screw-capped test tube was cooled down to −5° C. Butanesulfonyl chloride (45 μmol) was added as a 0.3 M solution in dichloromethane, with argon bubbling through the mixture during addition and for an additional 15 seconds. The mixture was allowed to stand at −5° C. overnight. Aminomethyl polystyrene resin (ca. 90 mg, 0.62 meq/g, 100–200 mesh, Bachem) was added and the mixture was warmed to reflux and shaken at about 600 rpm for 3 hours. The mixture was filtered through a Poly-Prep column (Bio-Rad #731–1550) to remove resin. Solvent was removed in vacuo and the residue was purified by semi-preparative hplc on a Gilson system (Rainin Microsorb C18 column, 21.4× 250 mm, 8 micron particle size, 60A pore, 10 mL/min., gradient elution from 2–95% B in 25 min., hold at 95% B for 5 min., where A=0.1% trifluoroacetic acid/water and B=0.1% trifluoroacetic acid/acetonitrile, peak detection at 254 nm for triggering fraction collection). The semi-prep hplc fractions were analyzed by LC-APCI/MS and the appropriate fractions were combined and lyophilized. The solid was dissolved in ca. 3 mL of 2:1 dichloromethane-methanol and shaken with ca. 80 mg (300 μmol) of diisopropylaminomethyl-polystyrene resin (Argonaut PS-DIEA, 3.86 mmol/g) for ~2 h to liberate the free amine, and then filtered and dried in vacuo to give the product as a solid. MS (APCI) m/e 376.16 (M+H).

EXAMPLE 14

N$^1$-{4-[4-Amino-2-(2-methoxyethyl)-6,7,8,9-tetrahydro-1H-imidazo[4,5-c]quinolin-1-yl]butyl}-4-fluoro-1-benzenesulfonamide

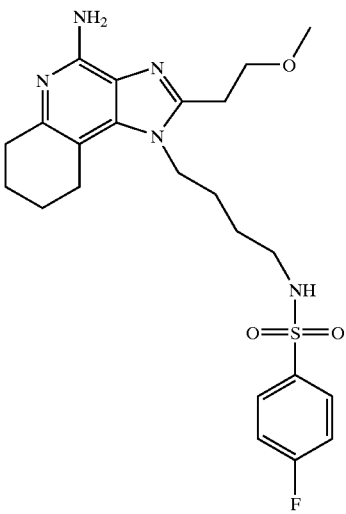

According to the general method of Example 5, 1-(4-aminobutyl)-2-(2-methoxyethyl)-6,7,8,9-tetrahydro-1H-imidazo[4,5-c]quinolin-4-amine and 4-fluorobenzenesulfonyl chloride were combined. Recrystallization from 4:1 n-propyl acetate\methanol provided N$^1$-{4-[4-amino-2-(2-methoxyethyl)-6,7,8,9-tetrahydro-1H-imidazo[4,5-c]quinolin-1-yl]butyl}-4-fluoro-1-benzenesulfonamide as a white crystalline solid, m.p. 191.0–193.0° C. $^1$H NMR (300 MHz, DMSO-d$_6$) δ 7.86–7.81 (m, 2H), 7.67 (broad s, 1H), 7.45–7.39 (m, 2H), 5.65 (broad s, 2H), 4.15 (m, 2H), 3.76 (t, J=6.7 Hz, 2H), 3.27 (s, 3H), 3.00 (t, J=6.7 Hz, 2H), 2.90 (broad s, 2H), 2.78 (m, 2H), 2.65 (broad s, 2H), 1.75 (broad s, 4H), 1.61 (m, 2H), 1.43 (m, 2H); MS (CI) m/e 476 (M+H). Analysis: Calculated for C$_{23}$H$_{30}$FN$_5$O$_3$S: %C, 58.09; %H, 6.36; %N, 14.73; Found: %C, 58.37; %H, 6.35; %N, 14.60.

EXAMPLE 15

N-[4-(4-Amino-2-phenyl-1H-imidazo[4,5-c]quinolin-1-yl)butyl]-4-fluoro-1-benzenesulfonamide

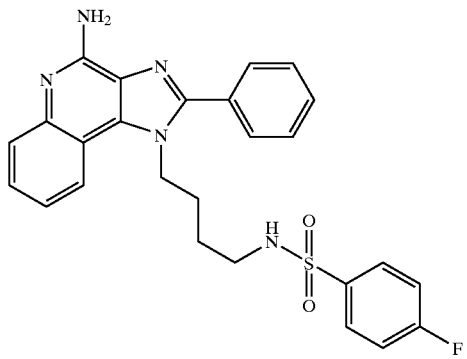

Part A

A solution of benzoyl chloride (5.3 g, 37.7 mmol) in dichloromethane (100 mL) was slowly added to a solution of tert-butyl N-{4-[(3-aminoquinolin-4-yl)amino]butyl}carbamate (12.5 g, 37.7 mmol) in dichloromethane (250 mL) at ambient temperature. The reaction mixture was maintained at ambient temperature overnight. The resulting precipitate was isolated by filtration and dried to provide 11.0 g of tert-butyl N-(4-{[3-(benzoylamino)quinolin-4-yl]amino}butyl)carbamate hydrochloride as a white solid.

Part B

Triethylamine (7.26 g, 71.7 mmol) was added to a solution of the material from Part A in ethanol (200 mL) and heated at reflux for 2 days. The reaction mixture was concentrated to provide an orange syrup. HPLC mass spec analysis showed that the syrup contained the desired product and starting material. The syrup was taken up in dichloromethane (100 mL) and then cooled in an ice bath. Triethylamine (5 mL) and benzoyl chloride (1.9 mL) were added. The reaction mixture was maintained at ambient temperature for 2 days at which time analysis by HPLC indicated that the reaction was not complete. The reaction mixture was concentrated under vacuum. The residue was taken up in isopropyl alcohol (150 mL). Triethylamine (5 mL) was added and the reaction mixture was heated at reflux overnight. The reaction mixture was concentrated under vacuum. The residue was purified by flash chromatography (silica gel; eluting with 10% methanol in dichloromethane). The fractions containing product were combined and concentrated under vacuum. The residue was recrystallized from acetonitrile to provide 6.7 g of tert-butyl N-[4-(2-phenyl-1H-imidazo[4,5-c]quinolin-1-yl)butyl]carbamate as a solid, m.p. 158–159° C.

Part C

3-Chloroperoxybenzoic acid (1.05 eq of 65%) was slowly added in small portions to a solution of tert-butyl N-[4-(2-phenyl-1H-imidazo[4,5-c]quinolin-1-yl)butyl]carbamate (6.56 g, 15.75 mmol) in dichloromethane (120 mL). After 3 hours the reaction was quenched with 1% aqueous sodium bicarbonate (200 mL). The layers were separated. The aqueous layer was extracted with dichloromethane (2×50 mL). The organic fractions were combined, dried over magnesium sulfate and then concentrated under vacuum to provide a pale orange syrup. The syrup was triturated with diethyl ether to provide 6.8 g of 1-[4-(tert-butylcarbamyl)butyl]-2-phenyl-1H-imidazo[4,5-c]quinoline-5N-oxide as a pale tan solid, m.p. 178–181° C.

Part D

A solution of 1-[4-(tert-butylcarbamyl)butyl]-2-phenyl-1H-imidazo[4,5-c]quinoline-5N-oxide (6.8 g, 15.75 mmol) in dichloromethane (100 mL) was chilled in an ice bath. Concentrated ammonium hydroxide (30 mL) was added. Tosyl chloride (3.0 g, 15.75 mmol) was added in small portions over a period of 30 minutes. The reaction mixture was allowed to warm to ambient temperature overnight. The reaction was quenched with water (350 mL). The layers were separated. The aqueous layer was extracted with dichloromethane. The organic fractions were combined, dried over magnesium sulfate and then concentrated under vacuum to provide a tan solid. This material was purified by flash chromatography (silica gel eluting with 10% methanol in dichloromethane) to provide 4.8 g of product. The bulk of the material was carried on to the next step. A small portion was recrystallized from toluene to provide tert-butyl N-[4-(4-amino-2-phenyl-1H-imidazo[4,5-c]quinolin-1-yl)butyl]carbamate as a solid, m.p. 182–183° C. Analysis: Calculated for $C_{25}H_{29}N_5O_2$: %C, 69.58; %H, 6.77; %N, 16.22; Found: %C, 69.86; %H, 6.95; %N, 15.80.

Part E

The material from Part D was dissolved in methanol (15 mL) and 1 N hydrochloric acid (100 mL) and then heated at reflux for 2 hours. The reaction mixture was concentrated under vacuum to a volume of about 50 mL. Addition of concentrated ammonium hydroxide to pH 12 did not produce a precipitate. The pH was adjusted to 7 with 1 N hydrochloric acid. The mixture was extracted with dichloromethane and then with ethyl acetate. The aqueous layer was concentrated to dryness. The residue was dissolved in water (50 mL) and then extracted continuously with refluxing chloroform for 36 hours. The chloroform extract was concentrated under vacuum to provide a light tan solid. This material was recrystallized from acetonitrile to provide 2.5 g of 1-(4-aminobutyl)-2-phenyl-1H-imidazo[4,5-c]quinolin-4-amine as an off white solid, m.p. 175–177° C. Analysis: Calculated for $C_{20}H_{21}N_5$: %C, 72.48; %H, 6.39; %N, 21.13; Found: %C, 72.72; %H, 6.32; %N, 20.71.

Part F 1-(4-Aminobutyl)-2-phenyl-1H-imidazo[4,5-c]quinolin-4-amine (0.331 g, 1.0 mmol) was dissolved in anhydrous acetonitrile (35 mL) and the solution was cooled to 4° C. A solution of 4-fluorobenzenesulfonyl chloride (0.194 g, 1.0 mmol) in anhydrous dichloromethane (10 mL) was slowly added. The reaction was allowed to slowly warm to ambient temperature over the weekend. The reaction was quenched by the addition of aqueous saturated sodium bicarbonate solution. The layers were separated and the organic layer was concentrated to provide a pale yellow solid. This material was recrystallized from isopropyl alcohol and then further purified by flash chromatography (silica gel eluting with 10% methanol in dichloromethane). The pure fractions were combined and concentrated. The residue was recrystallized from isopropyl alcohol to provide 0.2 g of N-[4-(4-amino-2-phenyl-1H-imidazo[4,5-c]quinolin-1-yl)butyl]-4-fluoro-1-benzenesulfonamide as a pale yellow solid, m.p. 214–216° C. Analysis: Calculated for $C_{26}H_{24}FN_5O_2S$: %C, 63.79; %H, 4.94; %N, 14.30; Found: %C, 63.19; %H, 4.85; %N, 13.90. Mass spec M+1=490.2.

EXAMPLE 16

N-[4-(4-Amino-2-phenyl-1H-imidazo[4,5-c]quinolin-1-yl)butyl]methanesulfonamide

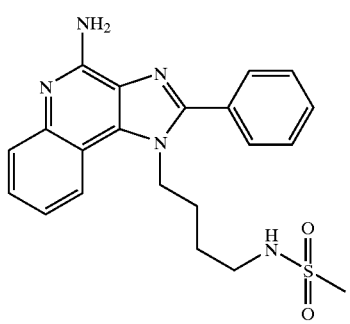

Using the general method of Example 15 Part F, 1-(4-aminobutyl)-2-phenyl-1H-imidazo[4,5-c]quinolin-4-amine (0.331 g, 1.0 mmol) was reacted with methanesulfonic anhydride to provide 0.14 g of N-[4-(4-Amino-2-phenyl-1H-imidazo[4,5-c]quinolin-1-yl)butyl]methanesulfonamide as a white solid, m.p. 234–235° C. Mass spec M+1=410.2.

EXAMPLES 17–33

The compounds shown in the Table below were prepared using the synthetic method described in Reaction Scheme II above.

1-(2-Aminoethyl)-2-butyl-1H-imidazo[4,5-c]quinolin-4-amine (25 mg) was placed in a 2 dram (7.4 mL) vial. Diisopropylethylamine (11 µL, 1.2 eq), dichloromethane (1 mL) and the sulfonyl chloride (11.1 eq) were added in order. The vial was placed on a shaker for about 2 hours and then on a sonicator for about 0.5 hours. The reaction mixture was allowed to stand at ambient temperature overnight and analyzed by LC/MS to confirmn the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of the Free Base | Observed Mass |
| --- | --- | --- |
| 17 | | 390.2 |
| 18 | | 460.2 |
| 19 | | 430.1 |

-continued

| Example # | Structure of the Free Base | Observed Mass |
|---|---|---|
| 20 | (4-amino-2-butyl-1H-imidazo[4,5-c]quinolin-1-yl)ethyl benzenesulfonamide | 424.1 |
| 21 | (4-amino-2-butyl-1H-imidazo[4,5-c]quinolin-1-yl)ethyl 4-bromobenzenesulfonamide | 504.0 |
| 22 | (4-amino-2-butyl-1H-imidazo[4,5-c]quinolin-1-yl)ethyl 3,4-dichlorobenzenesulfonamide | 492.0 |
| 23 | (4-amino-2-butyl-1H-imidazo[4,5-c]quinolin-1-yl)ethyl 4-methylbenzenesulfonamide | 438.1 |

-continued

| Example # | Structure of the Free Base | Observed Mass |
|---|---|---|
| 24 | | 534.0 |
| 25 | | 480.2 |
| 26 | | 466.2 |
| 27 | | 454.1 |

-continued

| Example # | Structure of the Free Base | Observed Mass |
|---|---|---|
| 28 | (4-amino-2-butyl-1H-imidazo[4,5-c]quinolin-1-yl)ethyl benzylsulfonamide | 438.1 |
| 29 | (4-amino-2-butyl-1H-imidazo[4,5-c]quinolin-1-yl)ethyl (E)-2-phenylethenesulfonamide | 450.1 |
| 30 | (4-amino-2-butyl-1H-imidazo[4,5-c]quinolin-1-yl)ethyl quinoline-8-sulfonamide | 475.1 |
| 31 | (4-amino-2-butyl-1H-imidazo[4,5-c]quinolin-1-yl)ethyl naphthalene-1-sulfonamide | 474.2 |

-continued

| Example # | Structure of the Free Base | Observed Mass |
|---|---|---|
| 32 | | 474.1 |
| 33 | | 517.2 |

EXAMPLE 34

N-[2-(4-Amino-2-butyl-1H-imidazo[4,5-c]quinolin-1-yl)-ethyl]methanesulfonamide Trifluoroacetate

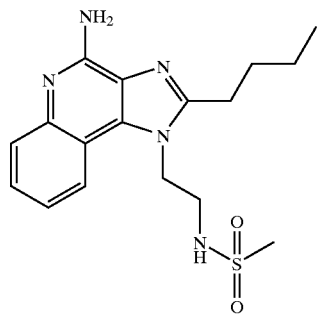

This compound was prepared using the method of Examples 17–33 above except that 1.1 eq of methanesulfonic anhydride was used in place of the sulfonyl chloride. (Observed Mass=362.2)

EXAMPLE 35

N-[2-(4-Amino-2-butyl-1H-imidazo[4,5-c]quinolin-1-yl)ethyl]trifluoromethanesulfonamide Trifluoroacetate

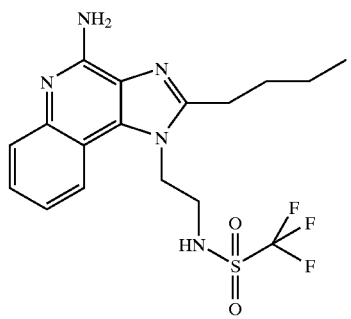

This compound was prepared using the method of Examples 17–33 above except that 1.1 eq of trifluoromethanesulfonic anhydride was used in place of the sulfonyl chloride. (Observed Mass=416.1)

EXAMPLES 36–48

The compounds shown in the Table below were prepared using the synthetic method described in Reaction Scheme II above.

1-(4-Aminobutyl)-2-butyl-1H-imidazo[4,5-c]quinolin-4-amine (25 mg) was placed in a 2 dram (7.4 mL) vial. Diisopropylethylamine (14 μL, 1.0 eq), dichloromethane (1 mL) and the sulfonyl chloride (1.0 eq) were added in order. The vial was placed on a shaker for about 30 minutes at which time almost everything was in solution. Some time later a precipitate formed. A small amount of methanol was added and the precipitate dissolved. The reaction mixture was left on the shaker for an additional hour and then it was put on a sonicator for about 0.5 hours. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of Free Base | Observed Mass |
|---|---|---|
| 36 | | 390.1 |
| 37 | | 482.1 |
| 38 | | 418.1 |

| Example # | Structure of Free Base | Observed Mass |
|---|---|---|
| 39 | (structure) | 452.1 |
| 40 | (structure) | 466.1 |

EXAMPLES 41–52

The compounds shown in the Table below were prepared using the synthetic method described in Reaction Scheme II above.

1-(4-Aminobutyl)-2-butyl-1H-imidazo[4,5-c]quinolin-4-amine (25 mg) was placed in a 2 dram (7.4 mL) vial. Diisopropylethylamine (14 μL, 1.0 eq), dichloromethane (1 mL) and the sulfonyl chloride (1.0 eq) were added in order. The vial was placed on a sonicator at ambient temperature for about 60 minutes. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of Free Base | Observed Mass |
|---|---|---|
| 41 | (structure) | 502.1 |

-continued

| Example # | Structure of Free Base | Observed Mass |
|---|---|---|
| 42 | | 502.1 |
| 43 | | 503.2 |
| 44 | | 458.1 |
| 45 | | 494.2 |

-continued

| Example # | Structure of Free Base | Observed Mass |
|---|---|---|
| 46 | 4-amino-2-butyl-1-[4-(4-iodobenzenesulfonamido)butyl]-1H-imidazo[4,5-c]quinoline | 578.2 |
| 47 | 4-amino-2-butyl-1-[4-(4-tert-butylbenzenesulfonamido)butyl]-1H-imidazo[4,5-c]quinoline | 508.3 |
| 48 | 4-amino-2-butyl-1-[4-(3,4-dichlorobenzenesulfonamido)butyl]-1H-imidazo[4,5-c]quinoline | 520.1 |
| 49 | 4-amino-2-butyl-1-[4-(benzylsulfonamido)butyl]-1H-imidazo[4,5-c]quinoline | 466.2 |

-continued

| Example # | Structure of Free Base | Observed Mass |
|---|---|---|
| 50 | (4-amino-2-butyl-1H-imidazo[4,5-c]quinolin-1-yl)butyl-N-styrylsulfonamide (E-styryl) | 478.2 |
| 51 | (4-amino-2-butyl-1H-imidazo[4,5-c]quinolin-1-yl)butyl-N-propylsulfonamide | 418.2 |
| 52 | (4-amino-2-butyl-1H-imidazo[4,5-c]quinolin-1-yl)butyl-N-(5-bromo-2-methoxyphenyl)sulfonamide | 560.1 |

EXAMPLE 53

N-[4-(4-Amino-2-butyl-1H-imidazo[4,5-c]quinolin-1-yl)butyl]trifluoromethanesulfonamide Trifluoroacetate

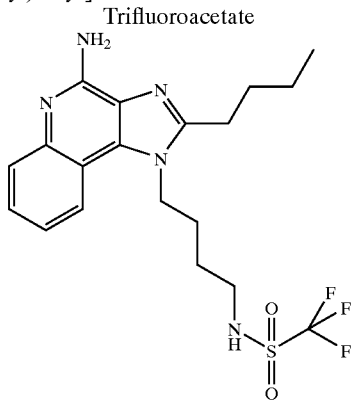

This compound was prepared using the method of Examples 41–52 above except that 1.0 eq of trifluoromethanesulfonic anhydride was used in place of the sulfonyl chloride. (Observed Mass=444.1)

EXAMPLES 54–71

The compounds shown in the Table below were prepared using the synthetic method described in Reaction Scheme IV above.

Part A

A catalytic amount of platinum (IV) oxide was added to a solution of 1-(4-aminobutyl)-1H-imidazo[4,5-c]quinolin-4-amine (2.75 g, 10.8 mmol) in trifluoroacetic acid (150 mL). The reaction mixture was placed under a hydrogen atmosphere at 50 psi ($3.44 \times 10^5$ Pa). After 1 week analysis by mass spectroscopy indicated the presence of both starting material and the tetrahydro product. Fresh catalyst was added to the reaction mixture and hydrogenation was continued at 50 psi ($3.44 \times 10^5$ Pa). After 2 weeks the reaction mixture was filtered to remove the catalyst. The filtrate was concentrated under vacuum. The residue was dissolved in 1N hydrochloric acid (120 mL) and the solution was stirred at ambient temperature for 1 hour. The solution was made basic (pH 10) by the addition of 50% sodium hydroxide and then extracted with dichloromethane (5×100 mL). The extracts were combined and concentrated under vacuum to provide 2.08 g of 1-(4-aminobutyl)-6,7,8,9-tetrahydro-1H-imidazo[4,5-c]quinolin-4-amine as a white solid.

Part B 1-(4-Aminobutyl)-6,7,8,9-tetrahydro-1H-imidazo[4,5-c]quinolin-4-amine (25 mg) was placed in a 2 dram (7.4 mL) vial. Diisopropylethylamine (11 μL, 1.2 eq), dichloromethane (1 mL) and the sulfonyl chloride (1.1 eq) were added in order. The vial was placed on a shaker for about 6 hours. The reaction mixture was allowed to stand at ambient temperature overnight and was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of Free Base | Observed Mass |
|---|---|---|
| 54 | | 366.2 |
| 55 | | 366.1 |

-continued

| Example # | Structure of Free Base | Observed Mass |
|---|---|---|
| 56 | | 436.2 |
| 57 | | 406.1 |
| 58 | | 400.1 |
| 59 | | 434.0 |

-continued

| Example # | Structure of Free Base | Observed Mass |
|---|---|---|
| 60 | | 468.0 |
| 61 | | 526.0 |
| 62 | | 456.1 |
| 63 | | 442 |

-continued
| Example # | Structure of Free Base | Observed Mass |
|---|---|---|
| 64 | 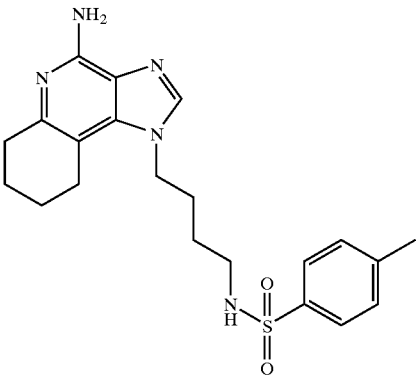 | 414 |
| 65 | 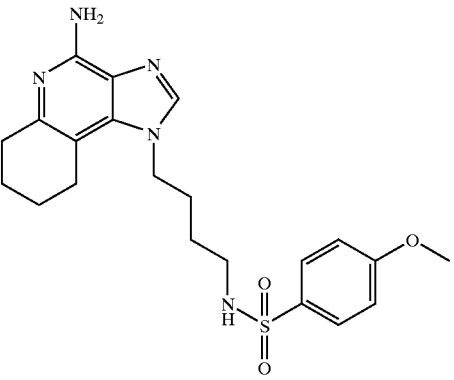 | 430 |
| 66 | 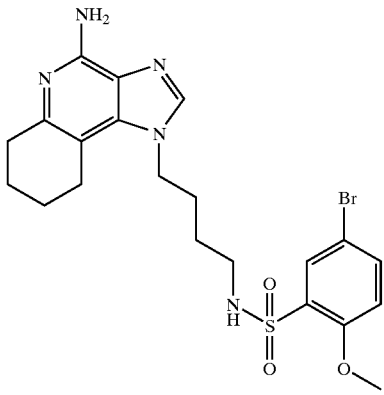 | 508.0 |
| 67 | 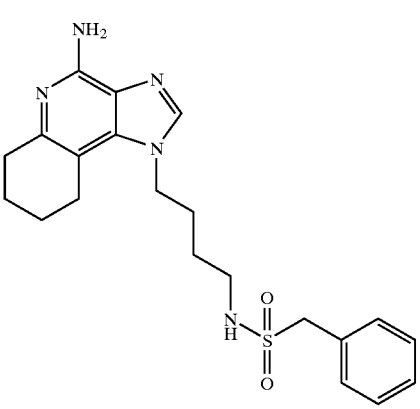 | 414.1 |

-continued

| Example # | Structure of Free Base | Observed Mass |
|---|---|---|
| 68 | | 426.1 |
| 69 | | 451.1 |
| 70 | | 450.1 |
| 71 | | 493.1 |

EXAMPLE 72

N-[4-(4-Amino-6,7,8,9-tetrahydro-1H-imidazo[4,5-c]quinolin-1-yl)butyl]methanesulfonamide Trifluoroacetate

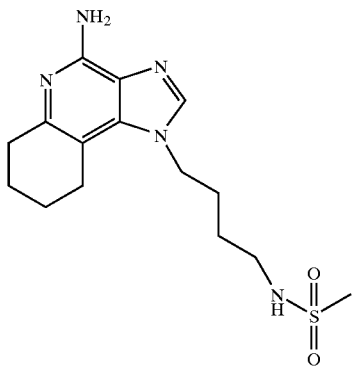

This compound was prepared using the method of Examples 54–71 above except that 1.1 eq of methanesulfonic anhydride was used in place of the sulfonyl chloride. (Observed Mass=338.2)

EXAMPLES 73–201

The compounds in the table below were prepared according the synthetic method of Reaction Scheme II above using the following general method.

The 1H-imidazo[4,5-c]quinolin-4-amine (50 mg) was placed in a 2 dram (7.4 mL) vial. Diisopropylethylamine (1.2 eq) in dichloromethane (~1 mL) was added. A solution containing the sulfonyl chloride (1.1 eq) in dichloromethane (~1 mL) was added. The vial was placed on a shaker for about 2–16 (usually 2) hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfonamide.

| Example # | Structure of the Free Base | APCI-MS m/e |
|---|---|---|
| 73 | | 526.2 |
| 74 | | 432.2 |

-continued

| Example # | Structure of the Free Base | APCI-MS m/e |
|---|---|---|
| 75 | | 600.3 |
| 76 | | 578.2 |
| 77 | | 530.1 |
| 78 | | 530, 532.0 |

-continued
| Example # | Structure of the Free Base | APCI-MS m/e |
|---|---|---|
| 79 | 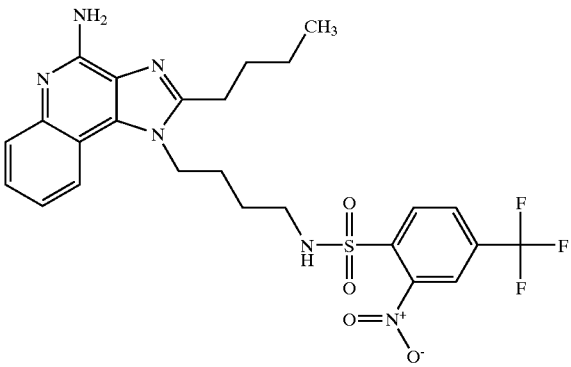 | 565.0 |
| 80 | 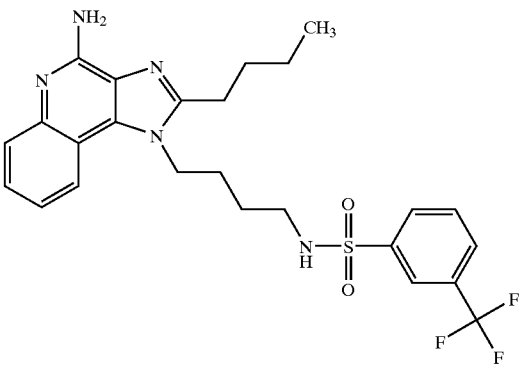 | 520.1 |
| 81 | 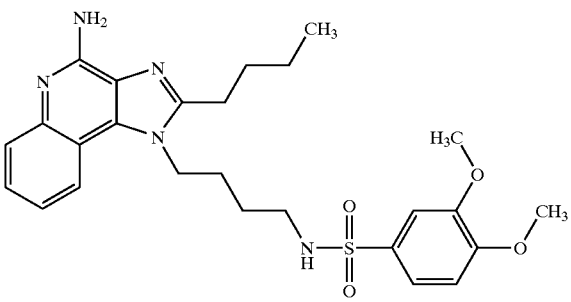 | 512.1 |
| 82 | 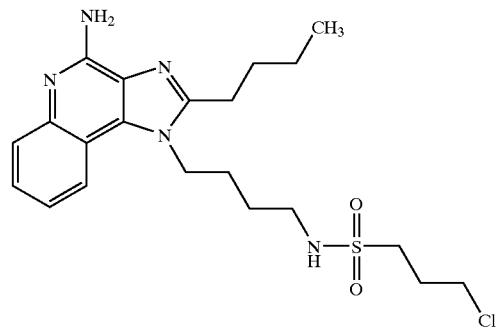 | 452.1 |

-continued

| Example # | Structure of the Free Base | APCI-MS m/e |
|---|---|---|
| 83 | | 497.1 |
| 84 | | 496.1 |
| 85 | | 536.1 |
| 86 | | 531.0, 533.0 |

| Example # | Structure of the Free Base | APCI-MS m/e |
|---|---|---|
| 87 | | 470.1 |
| 88 | | 497.1 |
| 89 | | 526.2 |
| 90 | | 542.0 |

-continued
| Example # | Structure of the Free Base | APCI-MS m/e |
|---|---|---|
| 91 | 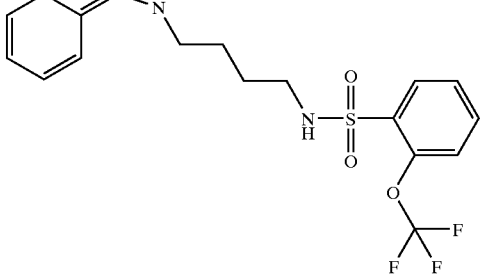 | 536.1 |
| 92 | 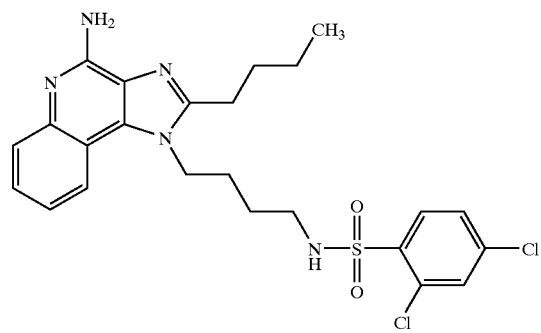 | 520.0, 522.0 |
| 93 | 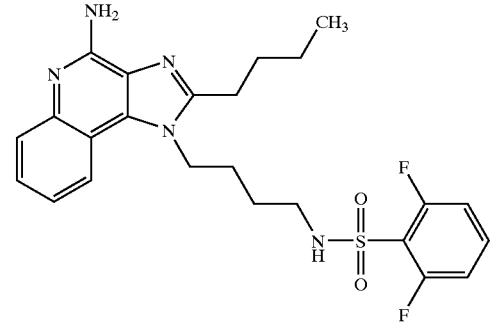 | 488.1 |
| 94 | 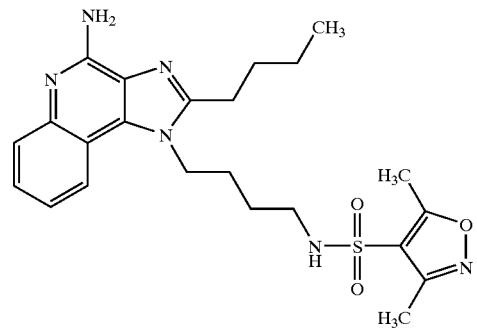 | 471.1 |

-continued

| Example # | Structure of the Free Base | APCI-MS m/e |
|---|---|---|
| 95 | | 470.1 |
| 96 | | 528.1 |
| 97 | | 511.1 |
| 98 | | 508.1 |

-continued

| Example # | Structure of the Free Base | APCI-MS m/e |
|---|---|---|
| 99 | | 537.9 |
| 100 | | 516.0, 518.0 |
| 101 | | 492.0, 494.0 |
| 102 | | 603.1 |

-continued

| Example # | Structure of the Free Base | APCI-MS m/e |
|---|---|---|
| 103 | | 520.1 |
| 104 | | 482.1 |
| 105 | | 560.0, 562 |
| 106 | | 484.1 |

-continued

| Example # | Structure of the Free Base | APCI-MS m/e |
|---|---|---|
| 107 | | 522.1 |
| 108 | | 364.1 |
| 109 | | 432.0 |
| 110 | | 519.1 |
| 111 | | 392.2 |

-continued

| Example # | Structure of the Free Base | APCI-MS m/e |
|---|---|---|
| 112 | | 460.1 |
| 113 | | 468.2 |
| 114 | | 547.3 |
| 115 | | 406.1 |

-continued

| Example # | Structure of the Free Base | APCI-MS m/e |
|---|---|---|
| 116 | | 420.1 |
| 117 | | 434.1 |
| 118 | | 454.1 |
| 119 | | 468.1 |

| Example # | Structure of the Free Base | APCI-MS m/e |
|---|---|---|
| 120 | | 472.1 |
| 121 | | 472.1 |
| 122 | | 472.1 |
| 123 | | 473.1 |

-continued

| Example # | Structure of the Free Base | APCI-MS m/e |
|---|---|---|
| 124 | | 484.1 |
| 125 | | 484.1 |
| 126 | | 488.1 |
| 127 | | 488.1 |

-continued
| Example # | Structure of the Free Base | APCI-MS m/e |
|---|---|---|
| 128 | 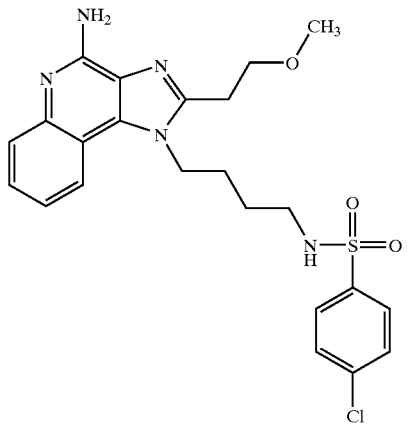 | 488.0 |
| 129 | 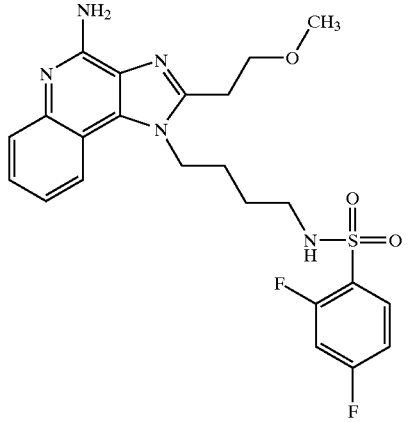 | 490.1 |
| 130 | 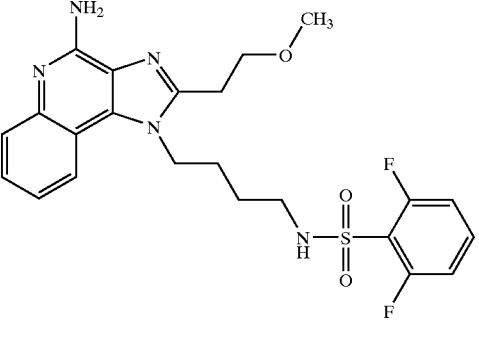 | 490.1 |
| 131 | 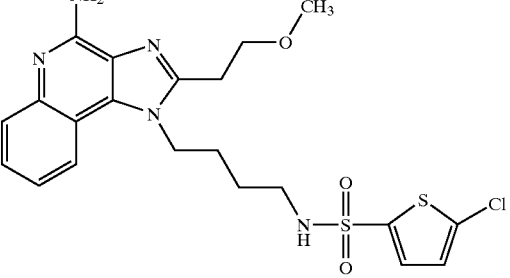 | 494.0 |

-continued

| Example # | Structure of the Free Base | APCI-MS m/e |
|---|---|---|
| 132 | | 496.2 |
| 133 | | 496.1 |
| 134 | | 496.2 |

-continued

| Example # | Structure of the Free Base | APCI-MS m/e |
|---|---|---|
| 135 | | 499.1 |
| 136 | | 499.1 |
| 137 | | 508.1 |

-continued
| Example # | Structure of the Free Base | APCI-MS m/e |
|---|---|---|
| 138 | 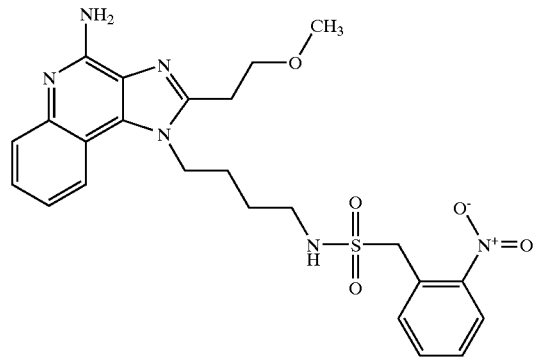 | 513.1 |
| 139 | 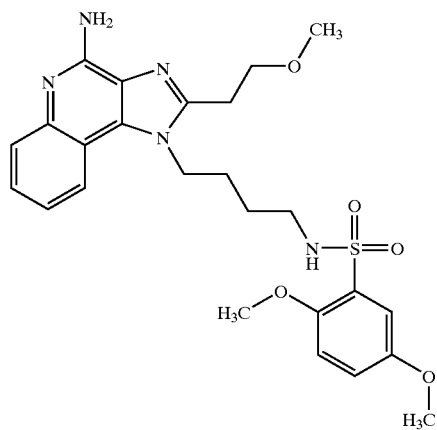 | 514.1 |
| 140 | 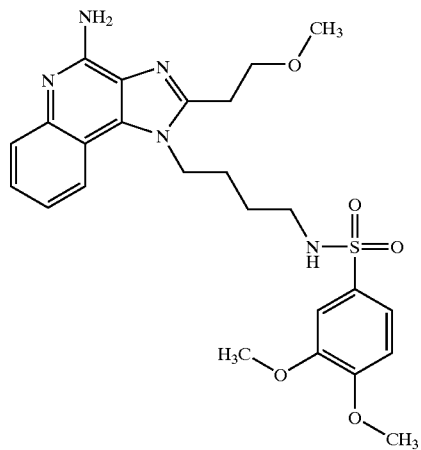 | 514.1 |

-continued
| Example # | Structure of the Free Base | APCI-MS m/e |
|---|---|---|
| 141 | 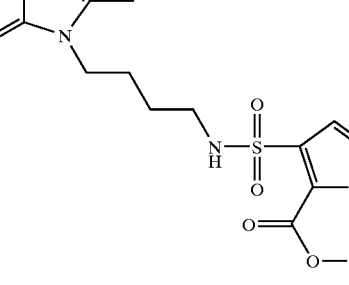 | 518.0 |
| 142 | 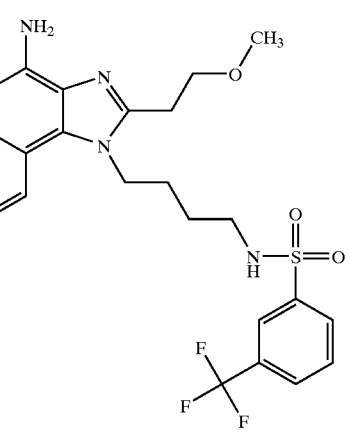 | 522.1 |
| 143 | 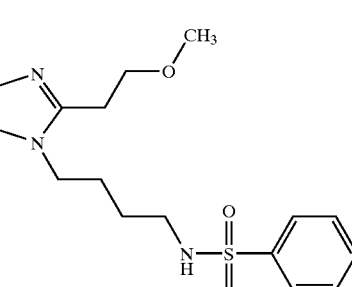 | 522.0, 524.0 |
| 144 | 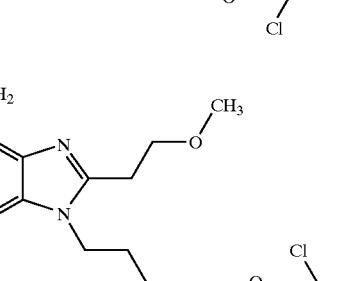 | 522.0, 524.0 |

-continued

| Example # | Structure of the Free Base | APCI-MS m/e |
|---|---|---|
| 145 | | 522.0, 524.0 |
| 146 | | 522.0, 524.0 |
| 147 | | 522.0, 524.0 |
| 148 | | 528.2 |

-continued
| Example # | Structure of the Free Base | APCI-MS m/e |
|---|---|---|
| 149 | 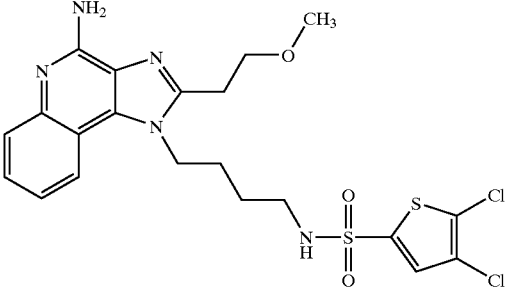 | 528.0, 530.0 |
| 150 | 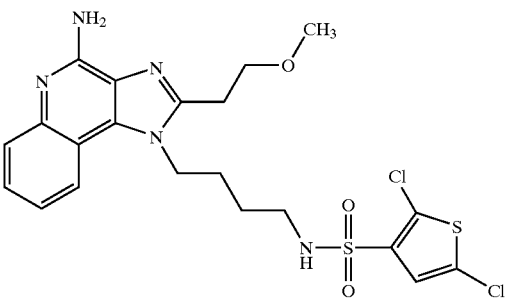 | 528.0, 530.0 |
| 151 | 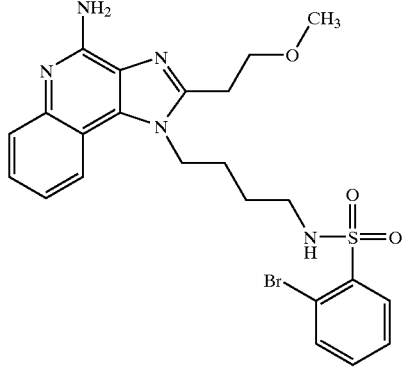 | 532, 534.0 |
| 152 | 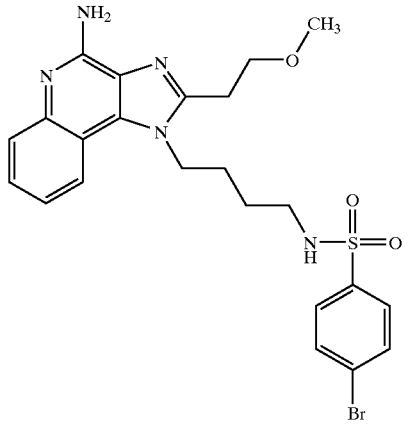 | 532, 534.0 |

-continued

| Example # | Structure of the Free Base | APCI-MS m/e |
|---|---|---|
| 153 | | 538.1 |
| 154 | | 538.1 |
| 155 | | 538, 540.0 |
| 156 | | 580.0 |

-continued

| Example # | Structure of the Free Base | APCI-MS m/e |
|---|---|---|
| 157 | | 605.1 |
| 158 | | 454.2 |
| 159 | | 468.2 |
| 160 | | 479.2 |

-continued

| Example # | Structure of the Free Base | APCI-MS m/e |
|---|---|---|
| 161 | | 532.2 |
| 162 | | 479.1 |
| 163 | | 486.1 |
| 164 | | 490.2 |

-continued

| Example # | Structure of the Free Base | APCI-MS m/e |
|---|---|---|
| 165 | | 498.1 |
| 166 | | 498.1 |
| 167 | | 502.1 |
| 168 | | 502.1 |

-continued

| Example # | Structure of the Free Base | APCI-MS m/e |
|---|---|---|
| 169 | | 504.2 |
| 170 | | 504.1 |
| 171 | | 505.2 |
| 172 | | 506.1 |

-continued
| Example # | Structure of the Free Base | APCI-MS m/e |
|---|---|---|
| 173 | 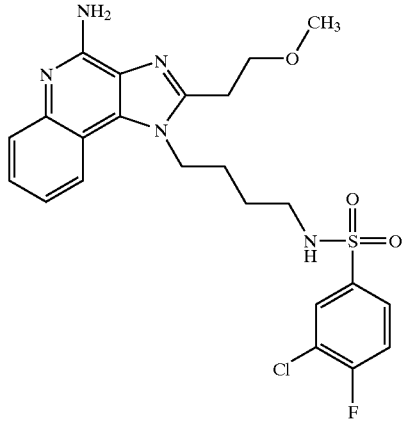 | 506.2 |
| 174 | 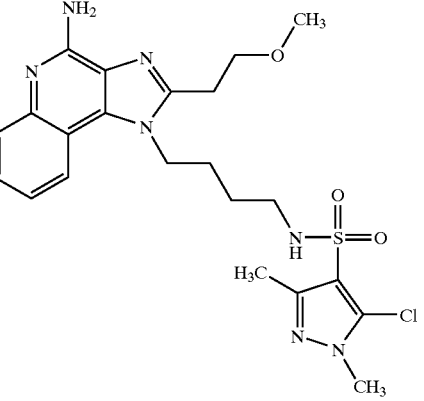 | 506.2 |
| 175 | 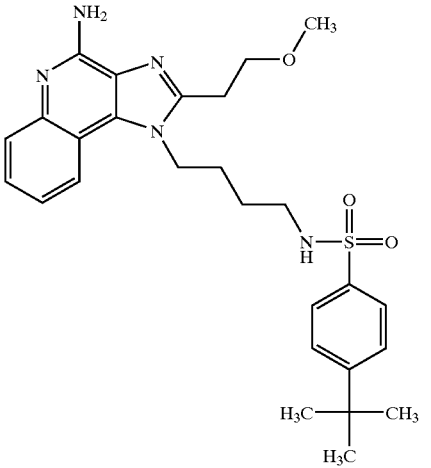 | 510.3 |

-continued

| Example # | Structure of the Free Base | APCI-MS m/e |
|---|---|---|
| 176 | | 510.2 |
| 177 | | 513.2 |
| 178 | | 513.2 |
| 179 | | 513.2 |

-continued
| Example # | Structure of the Free Base | APCI-MS m/e |
|---|---|---|
| 180 | 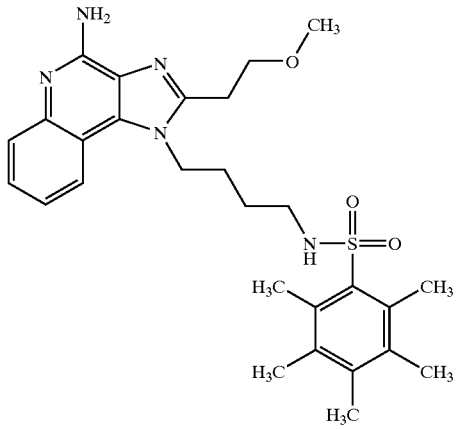 | 524.2 |
| 181 | 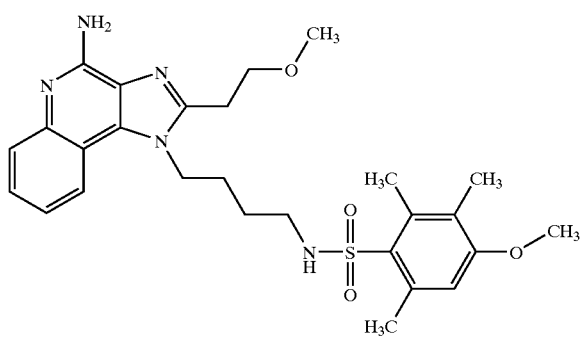 | 526.2 |
| 182 | 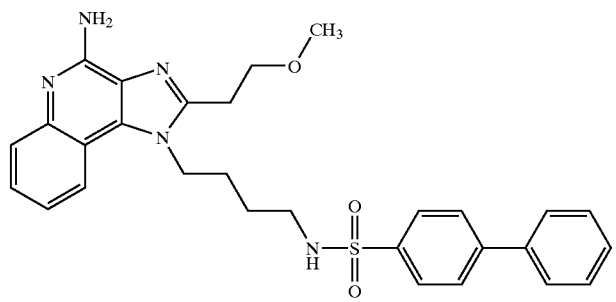 | 530.2 |
| 183 | 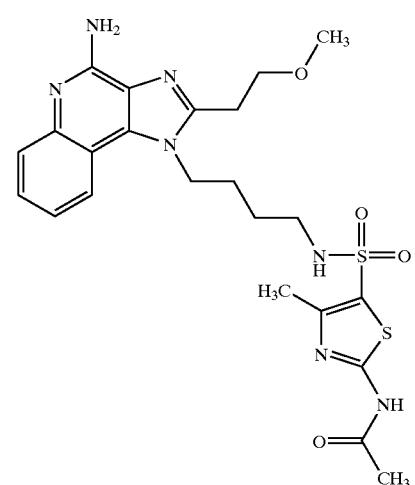 | 532.2 |

-continued

| Example # | Structure of the Free Base | APCI-MS m/e |
|---|---|---|
| 184 | | 534.1 |
| 185 | | 533.1 |
| 186 | | 536.1, 538.1 |
| 187 | | 544.1 |

-continued

| Example # | Structure of the Free Base | APCI-MS m/e |
|---|---|---|
| 188 | | 546.3 |
| 189 | | 556, 558.1 |
| 190 | | 556, 558.1 |
| 191 | | 556, 558.1 |

-continued

| Example # | Structure of the Free Base | APCI-MS m/e |
|---|---|---|
| 192 | | 562, 564.1 |
| 193 | | 567.2 |
| 194 | | 580.3 |
| 195 | | 593.2 |

-continued
| Example # | Structure of the Free Base | APCI-MS m/e |
|---|---|---|
| 196 | 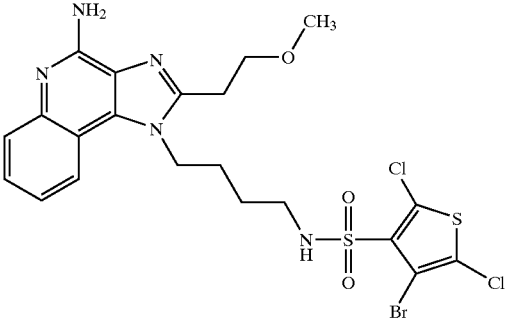 | 606.0, 608.0, 609.9 |
| 197 | 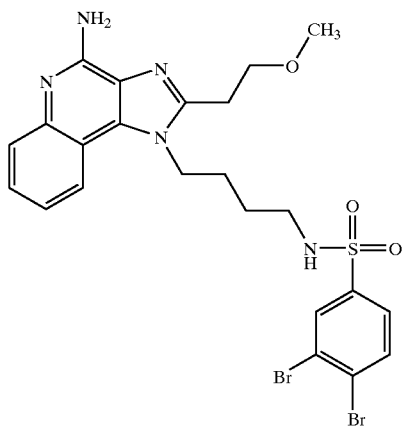 | 610.0, 612.0, 614.0 |
| 198 | 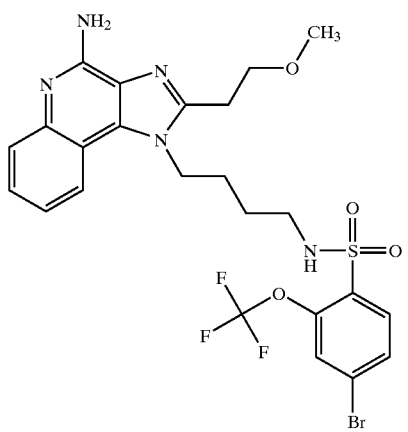 | 616, 618.1 |
| 199 | 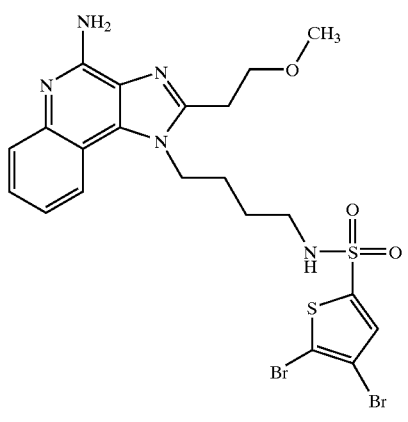 | 616.0, 617.9, 620.0 |

-continued

| Example # | Structure of the Free Base | APCI-MS m/e |
|---|---|---|
| 200 | | 528.3 |
| 201 | | 522.2 |

EXAMPLES 202–213

The examples in the table below were prepared according to the synthetic method of Reaction Scheme VI above.

Part A

The tetrahydroquinoline amine starting materials were prepared as follows.

A catalytic amount of platinum (IV) oxide was added to a solution of 1-(4-aminobutyl)-2-butyl-1H-imidazo[4,5-c]quinolin-4-amine (2.2 g, 7.06 mmol) in trifluoroacetic acid (200 mL). The reaction mixture was hydrogenated at 50 psi (3.44×10$^5$ Pa) on a Parr apparatus for 6 days. The reaction mixture was filtered to remove the catalyst and the filtrate was concentrated under vacuum. The residue was combined with 1 N hydrochloric acid (100 mL) and heated on a steam bath for 2 hours. The mixture was cooled, made basic with ammonium hydroxide and then extracted with dichloromethane. The extract was concentrated under vacuum to provide of 1-(4-aminobutyl)-2-butyl-6,7,8,9-tetrahydro-1H-imidazo[4,5-c]quinolin-4-amine as a solid, m.p. 63–67° C.

A catalytic amount of platinum (IV) oxide was added to a solution of 1-(4-aminobutyl)-2-methoxyethyl-1H-imidazo[4,5-c]quinolin-4-amine (7.7 g, 24.5 mmol) in trifluoroacetic acid (250 mL). The reaction mixture was hydrogenated at 50 psi (3.44×10$^5$ Pa) on a Parr apparatus. The progress of the reaction was monitored by LC/MS. Additional catalyst was added 7, 11, and 17 days after the start of the reaction. After 25 days the reaction was complete. The reaction mixture was filtered through a layer of Celite® filter aid to remove the catalyst and the filtrate was concentrated under vacuum. The residue was combined with 1 N hydrochloric acid (100 mL) and stirred overnight. The mixture was made basic (pH=11) with ammonium hydroxide and then extracted with dichloromethane (3×300 mL). The extracts were combined and concentrated under vide 3.5 g of 1-(4-aminobutyl)-6,7,8,9-tetrahydro-2-methoxyethyl-1H-quinolin-4-amine as a solid.

Part B

The trahydroimidazoquinoline amines from Part A were reacted with the appropriate sulfonyl chloride using the method of Examples 73–201 above to provide the desired sulfonamide.

| Example # | Structure of the Free Base | APCI-MS m/e |
|---|---|---|
| 202 | 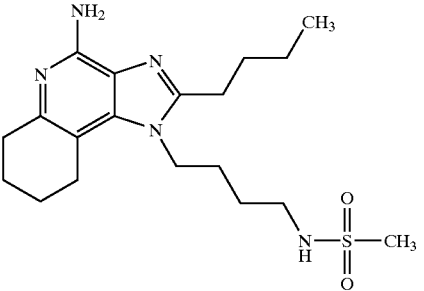 | 394.20 |
| 203 | 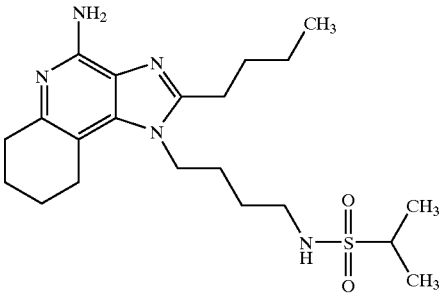 | 422.1 |
| 204 | 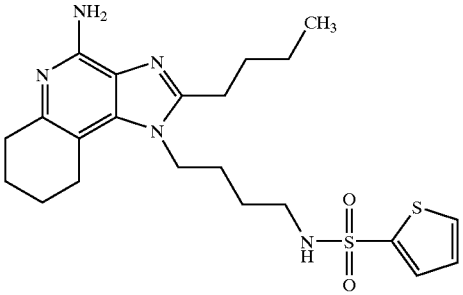 | 462.1 |
| 205 | 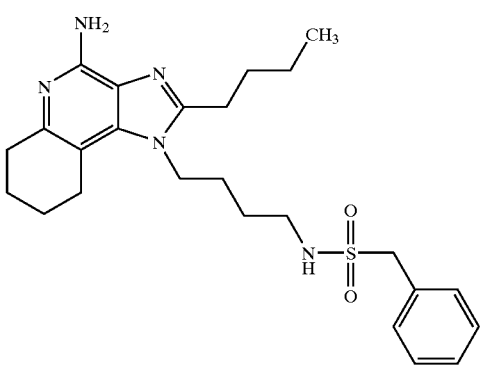 | 470.1 |

-continued

| Example # | Structure of the Free Base | APCI-MS m/e |
|---|---|---|
| 206 | | 549.2 |
| 207 | | 410.2 |
| 208 | | 424.2 |
| 209 | | 438.2 |

-continued

| Example # | Structure of the Free Base | APCI-MS m/e |
|---|---|---|
| 210 | | 458.1 |
| 211 | | 472.2 |
| 212 | | 532.2 |
| 213 | | 551.2 |

EXAMPLE 214

N-[4-(4-Amino-6,7,8,9-tetrahydro-2-(2-methoxyethyl)-1H-imidazo[4,5-c]quinolin-1-yl)butyl]methanesulfonamide Trifluoroacetat

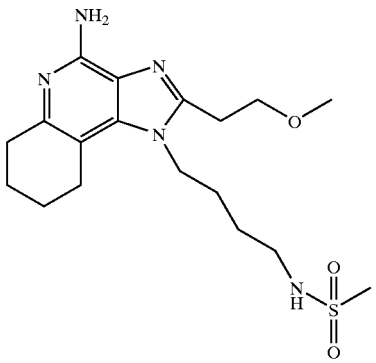

This compound was prepare using the method of Examples 202–213 above except that methanesulfonic anhydride was used in place of the sulfonyl chloride.

EXAMPLE 215

N-[4-(4-Amino-2-(2-methoxyethyl)-1H-imidazo[4,5-c]quinolin-1-yl)butyl]-methyl-3,5-dimethylisooxazolo-4-sulfonamide Trifluoroacetate

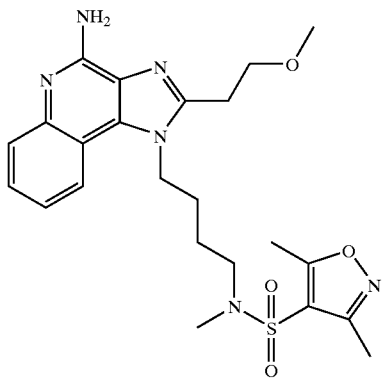

Part A

Using the general method of Example DC001, 1-(4-aminobutyl)-2-(2-methoxyethyl)-1H-imidazo[4,5-c]quinolin-4-amine was reacted with 3,5-dimethyloxazole-4-sulfonyl chloride to provide N-[4-(4-amino -2-(2-methoxyethyl)-1H-imidazo[4,5-c]quinolin-1-yl)butyl]-3,5-dimethylisooxazolo-4-sulfonamide trifluoroacetate.

Part B

Sodium hydride (5.8 mg) was added to a solution of the material from Part A (25.4 mg) in dimethylformamide. Iodomethane (3.2 µL) was added and the reaction mixture was shaken at ambient temperature for 2 hours. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized. The lyophilized material was purified a second time by semi-preparative HPLC using the same conditions except that the gradient elution from 5–95% B was run for 60 minutes instead of 10 minutes. The semi-prep HPLC fractions were analyzed by LC-APCI/MS and the appropriate fractions were combined and lyophilized to provide the trifluoroacetate salt of the desired amide.

EXAMPLE 216

N-[4-(4-Amino-2-(2-methoxyethyl)-1H-imidazo[4,5-c]quinolin-1-yl)butyl]-methyltrifluoromethanesulfonamide Trifluoroacetate

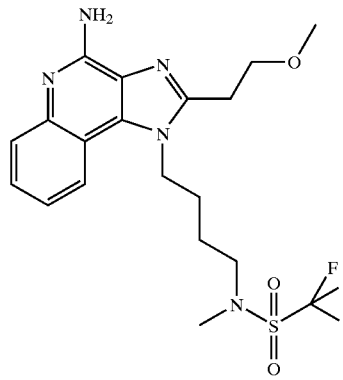

This compound was prepared using the general method of Example 215 above, except that trifluoromethanesulfonic anhydride was used in place of the sulfonyl chloride in Part A.

EXAMPLES 217–221

The examples in the table below were prepare using the following general method. The 1H-imidazo[4,5-c]quinolin-4-amine or the 6,7,8,9-tetrahydro-1H-imidazo[4,5-c]quinolin-4-amine (50 mg) was placed in a 2 dram (7.4 mL) vial. Dichloromethane (2 mL) and diisopropylethylamine (1.2 eq) were added. Dimethylsulfamoyl chloride (1.1 eq) was added. The vial was placed on a shaker for about 2–4 hours at ambient temperature. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by APCI/MS and the appropriate fractions were combined and lyophilized to provide the triflroacetate salt of the desired sulfamide.

| Example # | Structure of the Free Base | APCI-MS m/e |
|---|---|---|
| 217 | 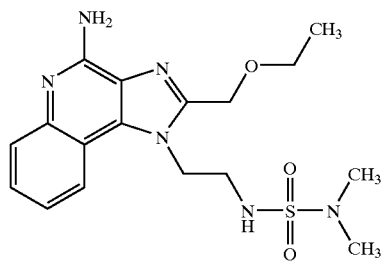 | 393.1 |
| 218 | 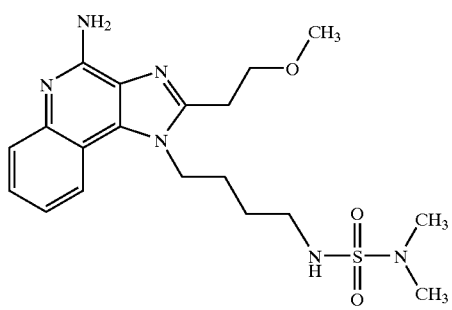 | 421.2 |
| 219 | 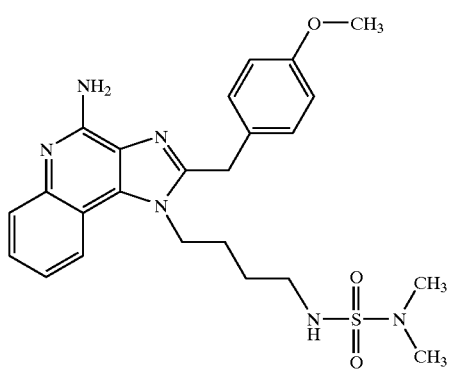 | 483.3 |
| 220 | 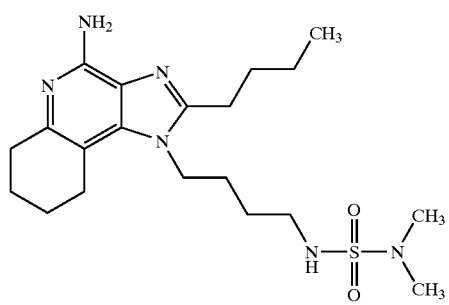 | 423.2 |

-continued

| Example # | Structure of the Free Base | APCI-MS m/e |
|---|---|---|
| 221 | (structure: 4-amino-6,7,8,9-tetrahydro-2-(2-methoxyethyl)-1-[4-(N,N-dimethylsulfamoylamino)butyl]-1H-imidazo[4,5-c]quinoline) | 425.1 |

EXAMPLES 222–228

The examples in the table below were prepared according to the synthetic method shown in Reaction Scheme V above.

1-(4-Aminobutyl)-2-(2-methoxyethyl)-1H-imidazo[4,5-c]quinolin-4-amine (50 mg) was placed in a 2 dram (7.4 mL) vial. 4-(Dimethylamino)pyridine (19 mg, 1.0 eq) and dichloromethane (800 µL) were added. The vial was sealed and cooled to −78° C. in a dry ice/acetone bath. Sulfuryl chloride (186 µL of 1 M in dichloromethane) was added. The vial was put on a shaker for about 30 minutes and then cooled back down to −78° C. A separate vial was charged with the amine of formula R₄R₅NH (2.0 eq), triethylamine (2.0 eq) and dichloromethane (1 mL) and cooled to −78° C. The amine/triethylamine solution was added to the first vial. The vial was placed on a shaker at ambient temperature for about 1 hour. The reaction mixture was analyzed by LC/MS to confirm the formation of the desired product. The solvent was removed and the residue was purified by semi-preparative HPLC (Capcell Pak C18 column, 35 mm×20 mm, 5 micron particle size, 20 mL/min., gradient elution from 5–95% B in 10 min., hold at 95% B for 2 min., where A=0.1% trifluoroacetic acid/water and B=0.1% trifluoroacetic acid/acetonitrile, peak detection at 254 nm for triggering fraction collection). The semi-prep HPLC fractions were analyzed by LC-APCI/MS and the appropriate fractions were combined and lyophilized to provide the trifluoroacetate salt of the desired sulfamide.

| Example # | Structure of the Free Base | APCI-MS m/e |
|---|---|---|
| 222 | (structure with isobutylamino sulfamide) | 449.2 |
| 223 | (structure with cyclohexylamino sulfamide) | 475.3 |

-continued
| Example # | Structure of the Free Base | APCI-MS m/e |
|---|---|---|
| 224 | 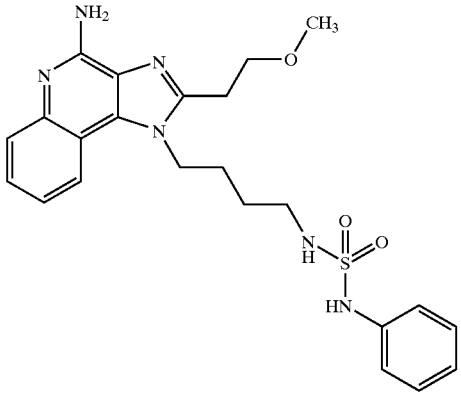 | 469.1 |
| 225 | 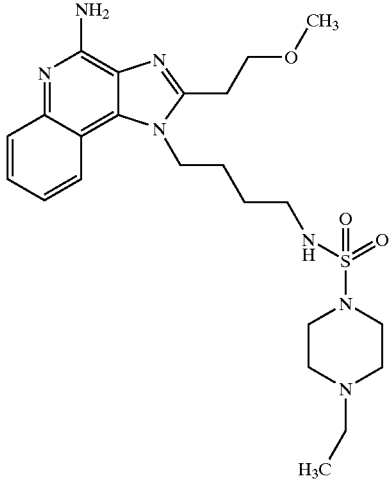 | 490.2 |
| 226 | 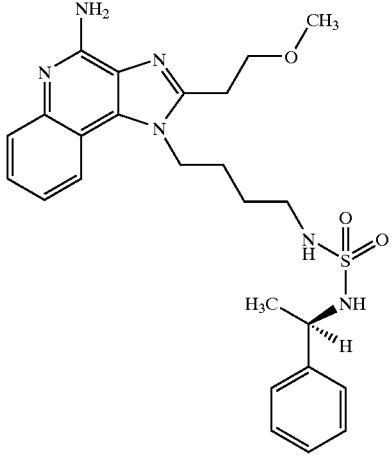 | 497.1 |

| Example # | Structure of the Free Base | APCI-MS m/e |
|---|---|---|
| 227 | (structure) | 533.2 |
| 228 | (structure) | 479.1 |

EXAMPLES 229–231

The examples in the table below were prepared using the method of Examples 222–228 above except that the amine of formula $R_4R_5NH$ was reacted with the sulfuryl chloride to provide the sulfamoyl chloride intermediate which was then reacted with 2.0 eq of 1-(4-aminobutyl)-2-(2-methoxyethyl)-1H-imidazo[4,5-c]quinolin-4-amine.

| Example # | Structure of the Free Base | APCI-MS m/e |
|---|---|---|
| 229 | (structure) | 447.1 |

| Example # | Structure of the Free Base | APCI-MS m/e |
|---|---|---|
| 230 | 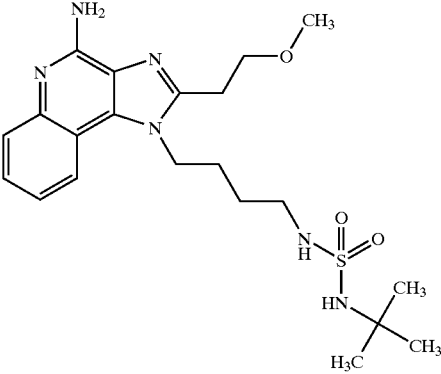 | 449.2 |
| 231 | 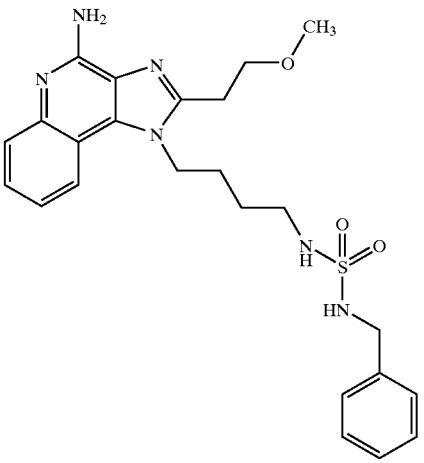 | 483.2 |

EXAMPLE 232

N-[4-(4-Amino-2-ethyl-1H-imidazo[4,5-c]quinolin-1-yl)butyl]benzenesulfonamide

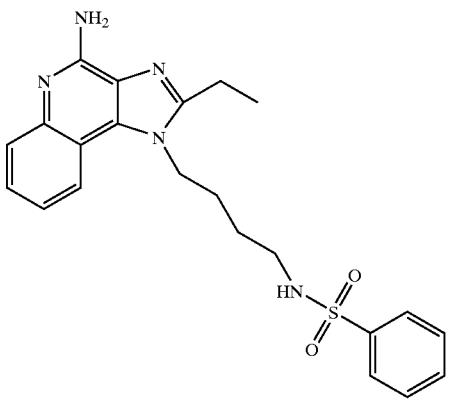

Triethylamine (1.18 mL, 8.5 mmol) was added to a mixture of 1-(4-aminobutyl)-2-ethyl-1H-imidazo[4,5-c]quinolin-4-amine (2.00 g, 7.1 mmol) and chloroform (200 mL). The resulting solution was chilled in an acetone/ice bath for 10 minutes. Benzenesulfonyl chloride (0.90 mL, 8.5 mmol) was slowly added over a period of 5 minutes. After 45 minutes 0.2 equivalents of triethylamine was added. After 6 hours the reaction mixture was washed with brine (2×250 mL) and with water (1×100 mL), dried over magnesium sulfate and then concentrated under reduced pressure. The residue was recrystallized from N,N-dimethylformamide. The recrystallized material and the filtrate were both slurried with methanol. The resulting solids were isolated by filtration, combined, and then dried in an Abderhalden drying apparatus overnight to provide 0.80 g of N-[4-(4-amino-2-ethyl-1H-imidazo[4,5-c]quinolin-1-yl)butyl] benzenesulfonamide as a white solid, m.p. 180.6–182.0° C. Analysis: Calculated for $C_{22}H_{25}N_5O_2S \cdot 0.25\ H_2O$: %C, 61.73; %H, 6.00; %N, 16.36; Found: %C, 61.79; %H, 6.04; %N, 16.43.

EXAMPLE 233

N-[4-(4-Amino-2-propyl-1H-imidazo[4,5-c]quinolin-1-yl)butyl]benzenesulfonamide

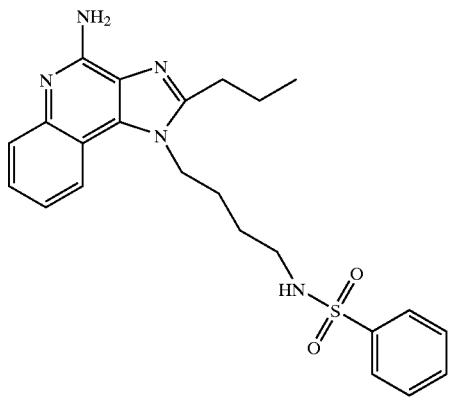

Part A

Tert-butyl 4-(2-propyl-1H-imidazo[4,5-c]quinolin-1-yl)butylcarbamate (5.00 g, 13.1 mmol) was combined with hydrochloric acid (50 mL of 4.0 M in dioxane) and stirred for 1.5 hours. The reaction mixture was diluted with dichloromethane (~200 mL). Saturated sodium bicarbonate solution was added until a pH of 8 was obtained. A precipitate formed in the aqueous phase. The layers were separated. The precipitate in the aqueous layer was isolated by filtration, slurried with water and then isolated by filtration to provide 3.6 g of 4-(2-propyl-1H-imidazo[4,5-c]quinolin-1-yl)butan-1-amine.

Part B

The material from Part A was combined with chloroform (600 mL) and warmed to 40° C. Triethylamine (3.48 mL, 25 mmol) was added and a solution was obtained. Benzenesulfonyl chloride (1.60 mL, 12.5 mmol) was added. The reaction mixture was stirred at 40° C. overnight. The reaction mixture was cooled to ambient temperature and then concentrated under reduced pressure. The residue was taken up in dichloromethane (~100 mL), washed with water (3×125 mL), dried over magnesium sulfate and then concentrated under reduced pressure to provide 3.96 g of N-[4-(2-propyl-1H-imidazo[4,5-c]quinolin-1-yl)butyl]benzenesulfonamide as a yellow crystalline solid, m.p. 155.9–157.1° C.

Part C

3-Chloroperoxybenzoic acid (896 mg of 77%) was added over a period of 5 minutes to a solution of N-[4-(2-propyl-1H-imidazo[4,5-c]quinolin-1-yl)butyl]benzenesulfonamide (1.0 g, 2.4 mmol) in chloroform (100 mL). After 2.5 hours an additional 0.1 equivalent of 3-chloroperoxybenzoic acid was added. After 3 hours the reaction was stored at a reduced temperature overnight. The reaction mixture was washed with saturated sodium bicarbonate solution (3×150 mL) and then concentrated under reduced pressure to provide 1.44 g of crude product. This material was recrystallized from methyl acetate to provide 0.67 g of 1-{4-[(phenylsulfonyl)amino]butyl}-2-propyl-1H-imidazo[4,5-c]quinolin-5N-oxide as a brown solid, m.p. 203.8–205.2° C.

Part D

Ammonium hydroxide (3.5 mL of 27%) was added to a mixture of the material from Part C and dichloromethane (15 mL). After 10 minutes tosyl chloride (0.35 g) was slowly added over a period of 5 minutes. After 45 minutes the reaction mixture was stored at a reduced temperature over the weekend. An additional 35 mg of tosyl chloride was added and the reaction mixture was stirred for 1 hour. The organic phase was separated and then washed with saturated sodium bicarbonate solution (3×80 mL). A precipitate formed in the aqueous phase. This material was isolated by filtration and then recrystallized from methyl acetate. The resulting solid and the filtrate were combined, dissolved in dichloromethane containing a small amount of methanol, and then purified by column chromatography (silica gel eluting with 10% methanol in dichloromethane). The resulting material was purified by column chromatography (silica gel eluting with 0–7.5% methanol in dichloromethane). This material was recrystallized 3 times from methyl acetate to provide 42 mg of N-[4-(4-amino-2-propyl-1H-imidazo[4,5-c]quinolin-1-yl)butyl]benzenesulfonamide as a white solid, m.p. 158.8–160.8° C. Analysis: Calculated for $C_{23}H_{27}N_5O_2S \cdot 0.25\ C_3H_6O_2$: %C, 62.15; %H, 6.22; %N, 15.59; Found: %C, 62.41; %H, 5.91; %N, 15.41.

EXAMPLE 234

N-[4-(4-Amino-2-hexyl-1H-imidazo[4,5-c]quinolin-1-yl)butyl]benzenesulfonamide

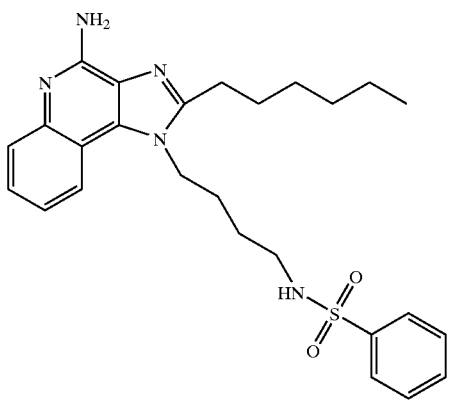

Part A

Using the general method of Example 233 Part A, tert-butyl 4-(2-hexyl-1H-imidazo[4,5-c]quinolin-1-yl)butylcarbamate (33.85 g) was hydrolyzed to provide 3.43 g of 4-(2-hexyl-1H-imidazo[4,5-c]quinolin-1-yl)butan-1-amine as an off white solid, m.p. 172.2–174.2° C.

Part B

Using the general method of Example 233 Part B except that the reaction was run at ambient temperature, 4-(2-hexyl-1H-imidazo[4,5-c]quinolin-1-yl)butan-1-amine (1.20 g, 3.7 mmol) was reacted with benzenesulfonyl chloride (429 μL, 3.7 mmol) to provide 0.75 g of N-[4-(2-hexyl-1H-imidazo[4,5-c]quinolin-1-yl)butyl]benzenesulfonamide as a light yellow solid, m.p. 137.0–138.1° C.

Part C

Using the general method of Example 233 Part C, N-[4-(2-hexyl-1H-imidazo[4,5-c]quinolin-1-yl)butyl]benzenesulfonamide (0.95 g, 2.0 mmol) was oxidized to provide 1.21 g of crude 1-{4-[(phenylsulfonyl)amino]butyl}-2-hexyl-1H-imidazo[4,5-c]quinolin-5N-oxide.

Part D

Using the general method of Example 233 Part D, the material from Part C was aminated to provide 118 mg of N-[4-(4-amino-2-hexyl-1H-imidazo[4,5-c]quinolin-1-yl)butyl]benzenesulfonamide as an off white crystalline solid, m.p. 84.8–85.4° C. Analysis: Calculated for $C_{26}H_{33}N_5O_2S \cdot 0.5\ H_2O$: %C, 63.91; %H, 7.01; %N, 14.33; Found: %C, 63.63; %H, 6.93; %N, 14.80.

EXAMPLE 235

N-[4-(4-Amino-2-propyl-1H-imidazo[4,5-c]quinolin-1-yl)butyl]methanesulfonamide

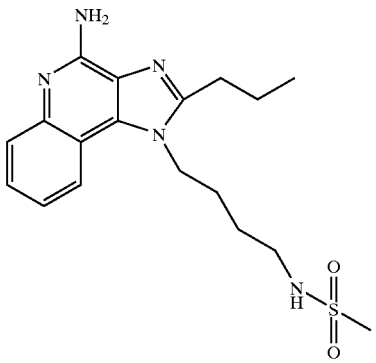

Part A

Using the general method of Example 233 Part B except that the reaction was run at ambient temperature, 4-(2-propyl-1H-imidazo[4,5-c]quinolin-1-yl)butan-1-amine (2.00 g, 7.1 mmol) was reacted with methanesulfonyl chloride (1.65 mL, 21.3 mmol) to provide 1.23 g of N-[4-(2-propyl-1H-imidazo[4,5-c]quinolin-1-yl)butyl]methanesulfonamide as a light yellow solid, m.p. 133.2–134.6° C.

Part B

Using the general method of Example 233 Part C, N-[4-(2-propyl-1H-imidazo[4,5-c]quinolin-1-yl)butyl]methanesulfonamide was oxidized to provide 1.44 g of crude 1-{4-[(methylsulfonyl)amino]butyl}-2-propyl-1H-imidazo[4,5-c]quinolin-5N-oxide asa light yellow solid.

Part C

Using the general method of Example 233 Part D, the material from Part B was aminated to provide 0.21 g of N-[4-(4-amino-2-propyl-1H-imidazo[4,5-c]quinolin-1-yl)butyl]methanesulfonamide as an off white crystalline solid, m.p. 186.5–187.9° C. Analysis: Calculated for $C_{18}H_{25}N_5O_2S \cdot 0.25\ H_2O$: %C, 56.89; %H, 6.76; %N, 18.43; Found: %C, 56.95; %H, 6.89; %N, 18.13.

EXAMPLE 236

N-[4-(4-Amino-2-ethyl-1H-imidazo[4,5-c]quinolin-1-yl)butyl]methanesulfonamide

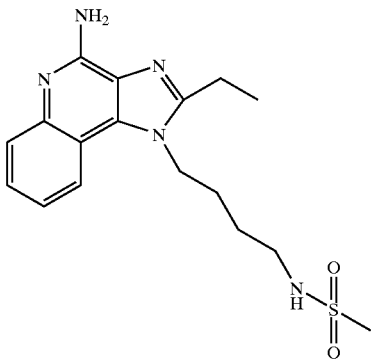

Part A

Using the general method of Example 233 Part A, tert-butyl 4-(2-ethyl-1H-imidazo[4,5-c]quinolin-1-yl)butylcarbamate (20.69 g) was hydrolyzed to provide 14.94 g of 4-(2-ethyl-1H-imidazo[4,5-c]quinolin-1-yl)butan-1-amine as an off white solid, m.p. 84.8–88.7° C.

Part B

Using the general method of Example 233 Part B, 4-(2-ethyl-1H-imidazo[4,5-c]quinolin-1-yl)butan-1-amine (4.00 g, 14.9 mmol) was reacted with methanesulfonyl chloride to provide 1.78 g of N-[4-(2-ethyl-1H-imidazo[4,5-c]quinolin-1-yl)butyl]methanesulfonamide as a light yellow solid.

Part C

Using the general method of Example 233 Part C, the material from Part B was oxidized to provide ~2.00 g of crude 1-{4-[(methylsulfonyl)amino]butyl}-2-ethyl-1H-imidazo[4,5-c]quinolin-5N-oxide.

Part D

Using the general method of Example 233 Part D, the material from Part C was aminated to provide 0.42 g of N-[4-(4-amino-2-ethyl-1H-imidazo[4,5-c]quinolin-1-yl)butyl]methanesulfonamide as a white solid, m.p. 203.3–204.4° C. Analysis: Calculated for $C_{17}H_{23}N_5O_2S$: %C, 56.49; %H, 6.41; %N, 19.37; Found: %C, 56.21; %H, 6.36; %N, 19.09.

EXAMPLE 237

N-[4-(4-Amino-2-methyl-1H-imidazo[4,5-c]quinolin-1-yl)butyl]benzenesulfonamide

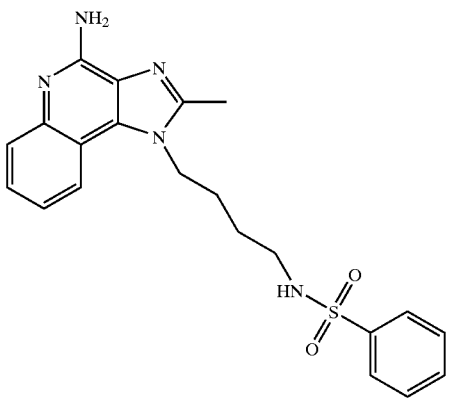

Using the general method of Example 232, 1-(4-aminobutyl)-2-methyl-1H-imidazo[4,5-c]quinolin-4-amine (0.50 g, 1.9 mmol) was reacted with benzenesulfonyl chloride (0.24 mL, 1.9 mmol) to provide 0.38 g of N-[4-(4-amino-2-methyl-1H-imidazo[4,5-c]quinolin-1-yl)butyl]benzenesulfonamide as brown granules, m.p. 215.4–216.0° C. Analysis: Calculated for $C_{21}H_{23}N_5O_2S$: %C, 61.59; %H, 5.66; %N, 17.10; Found %C, 61.24; %H, 5.65; %N, 16.95.

EXAMPLE 238

N-[4-(4-Amino-2-methyl-1H-imidazo[4,5-c]quinolin-1-yl)butyl]methanesulfonamide

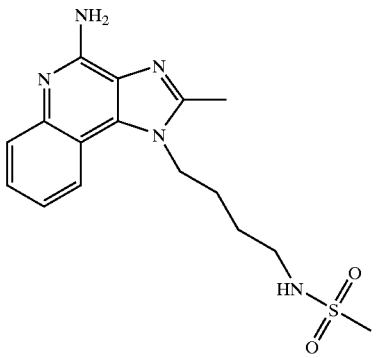

Using the general method of Example 232, 1-(4-aminobutyl)-2-methyl-1H-imidazo[4,5-c]quinolin-4-amine (1.00 g, 3.7 mmol) was reacted with methanesulfonyl chloride (0.46 mL, 5.9 mmol) to provide 0.16 g of N-[4-(4-amino-2-methyl-1H-imidazo[4,5-c]quinolin-1-yl)butyl] methanesulfonamide as an off white solid, m.p. 229.4–230.5° C. Analysis: Calculated for $C_{16}H_{21}N_5O_2S\cdot0.25\ H_2O$: %C, 54.60; %H, 6.16; %N, 19.90; Found: %C, 54.80; %H, 6.24; %N, 19.58.

EXAMPLE 239

N-[3-(4-Amino-2-butyl-1H-imidazo[4,5-c]quinolin-1-yl)propyl]methanesulfonamide

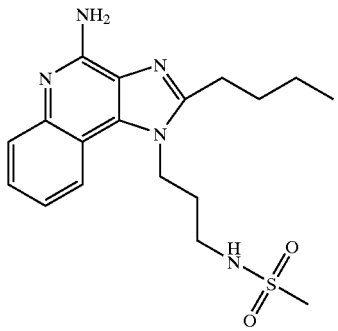

Part A

Tert-butyl 3-(2-butyl-1H-imidazo[4,5-c]quinolin-1-yl)propylcarbamate (~80 g) was dissolved in 1,4-dioxane (400 mL) with gentle heating. Hydrochloric acid (55 mL of 4.0 M in 1,4-dioxane) was added in a single portion and the reaction was heated to reflux. The reaction was monitored by HPLC. Additional acid (150–200 mL) was added and the reaction mixture was refluxed until the reaction was complete. The reaction mixture was cooled to ambient temperature. A solid was isolated by filtration to give ~72 g of 3-(2-butyl-1H-imidazo[4,5-c]quinolin-1-yl)propylamine hydrochloride. This material was combined with that from a previous experiment and then dissolved in water (400 mL). The solution was neutralized with solid potassium carbonate. At pH 7 a solid precipitated. The solid was isolated by filtration and then dissolved in water (1500 mL). The pH was adjusted to pH 10 with solid potassium carbonate. The solution was extracted with chloroform until HPLC analysis showed that no amine remained in the aqueous layer. The organic layers were combined and then concentrated under reduced pressure to provide 45 g of 3-(2-butyl-1H-imidazo[4,5-c]quinolin-1-yl)propylamine.

Part B

Triethylamine (1.1 g, 10.6 mmol) was added with stirring to a solution of 3-(2-butyl-1H-imidazo[4,5-c]quinolin-1-yl)propylamine (2.00 g, 7.08 mmol) in dichloromethane (~150 mL). Methanesulfonyl chloride (892 mg, 7.79 mmol) was added and the reaction was stirred under nitrogen overnight. The reaction mixture was washed with aqueous 1% sodium bicarbonate solution (3×50 mL). The aqueous washes were extracted with dichloromethane (2×20 mL). The organics were combined, dried over magnesium sulfate and then concentrated under reduced pressure to provide 1.89 g of N-[3-(2-butyl-1H-imidazo[4,5-c]quinolin-1-yl)propyl]methanesulfonamide as a light brown solid.

Part C

Using the general method of Example 233 Part C, the material from Part B was oxidized to provide 1.24 g of N-[3-(2-butyl-5-oxido-1H-imidazo[4,5-c]quinolin-1-yl)propyl]methanesulfonamide.

Part D

Using the general method of Example 233 Part D, the material from Part C was animated to provide 690 mg of N-[3-(4-amino-2-butyl-1H-imidazo[4,5-c]quinolin-1-yl)propyl]methanesulfonamide as a light tan solid, m.p. 239.2–240.8° C. Analysis: Calculated for $C_{18}H_{25}N_5O_2S$: %C, 57.58; %H, 6.71; %N, 18.65; Found: %C, 57.37; %H, 6.78; %N, 18.42.

EXAMPLE 240

N-[3-(4-Amino-2-butyl-1H-imidazo[4,5-c]quinolin-1-yl)propyl]benzenesulfonamide

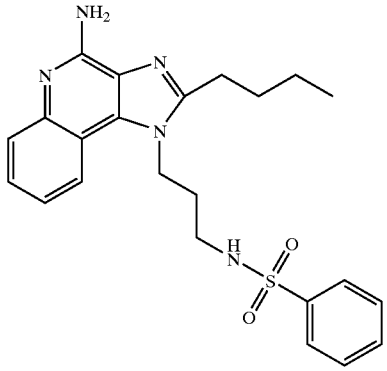

Part A

Using the general method of Example 239 Part B, 3-(2-butyl-1H-imidazo[4,5-c]quinolin-1-yl)propylamine (2.00 g, 7.08 mmol) was reacted with benzenesulfonyl chloride (1.38 g, 7.79 mmol) to provide 2.83 g of N-[3-(2-butyl-1H-imidazo[4,5-c]quinolin-1-yl)propyl]benzenesulfonamide as a light red foam.

Part B

Using the general method of Example 233 Part C, the material from Part A was oxidized to provide 3.28 g of N-[3-(2-butyl-5-oxido-1H-imidazo[4,5-c]quinolin-1-yl)propyl]benzenesulfonamide.

Part C

Using the general method of Example 233 Part D, the material from Part B was animated to provide 1.08 g of N-[3-(4-amino-2-butyl-1H-imidazo[4,5-c]quinolin-1-yl)propyl]benzenesulfonamide as a light tan solid, m.p. 210.5–212.0° C. Analysis: Calculated for $C_{23}H_{27}N_5O_2S$: %C, 63.13; %H. 6.22; %N, 16.01; Found: %C, 62.89; %H, 6.16; %N, 15.74.

EXAMPLE 241
N-[4-(4-Amino-2-hexyl-1H-imidazo[4,5-c]quinolin-1-yl)butyl]methanesulfonamide

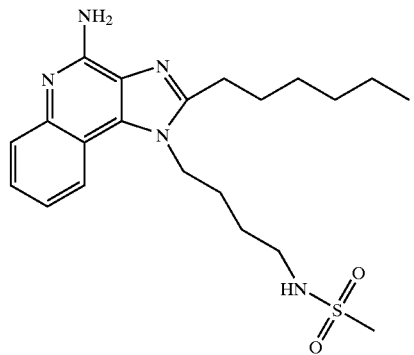

Part A
Using the general method of Example 232, 4-(2-hexyl-1H-imidazo[4,5-c]quinolin-1-yl)butan-1-amine (1.00 g, 3.1 mmol) was reacted with methanesulfonyl choride (0.48 mL, 6.2 mmol) to provide 1.15 g of N-[4-(2-hexyl-1H-imidazo[4,5-c]quinolin-1-yl)butyl]methanesulfonamide as a white solid.

Part B
Using the general method of Example 233 Part C, N-[4-(2-hexyl-1H-imidazo[4,5-c]quinolin-1-yl)butyl]methanesulfonamide (1.47 g, 3.7 mmol) was oxidized to provide 3.78 g of crude 1-{4-[(methylsulfonyl)amino]butyl}-2-hexyl-1H-imidazo[4,5-c]quinolin-5N-oxide as a yellow residue.

Part C
Using the general method of Example 233 Part D, the material from Part B was animated to provide 0.28 g of N-[4-(4-amino-2-hexyl-1H-imidazo[4,5-c]quinolin-1-yl)butyl]methanesulfonamide as an off white solid, m.p. 170.2–171.1° C. Analysis: Calculated for $C_{21}H_{31}N_5O_2S$: %C, 60.40; %H, 7.48; %N, 16.77; Found: %C, 59.97; %H, 7.26; %N, 16.33.

EXAMPLE 242
N-{8-[4-Amino-2-(2-methoxyethyl)-1H-imidazo[4,5-c]quinolin-1-yl]octyl}benzenesulfonamide

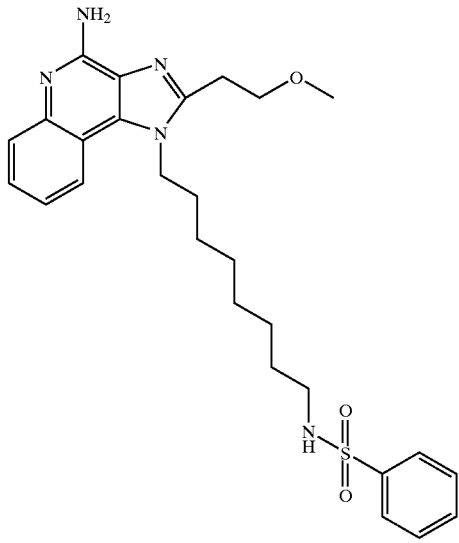

Under a nitrogen atmosphere a solution of 1-(8-aminooctyl)-2-(2-methoxyethyl)-1H-imidazo[4,5-c]quinolin-4-amine (1.0 g, 2.7 mmol) in didhloromethane (50 mL) was cooled to 0° C. Triethylamine (415 μL, 2.98 mmol) was added followed by benzenesulfonyl chloride (345 μL, 2.71 mmol). The reaction mixture was allowed to warm slowly to ambient temperature and then it was maintained overnight. The reaction mixture was washed with water, dried over magnesium sulfate and then concentrated under reduced pressure. The residue was purified by column chromatography (50 g of silica gel eluting with 7.5% methanol in dichloromethane). The purified material was recrystallized from propyl acetate, triturated with hexanes, and then dried in a vacuum oven to provide 590 mg of N-{8-[4-amino-2-(2-methoxyetyl)-1H-imidazo[4,5-c]quinolin-1-yl]octyl}benzenesulfonamide as a yellow powder, m.p. 146–149° C. Analysis: Calculated for $C_{27}H_{35}N_5O_3S$: %C, 63.63; %H, 6.92; %N, 13.74; Found: %C, 62.96; %H, 7.03; %N, 13.09. Karl Fisher showed 0.16% or 0.045 mole water.

$^1$H NMR (300 MHz, DMSO-$d_6$) δ 801 (d, J=7.8 Hz, 1H), 7.78 (m, 2H), 7.65–7.55 (m, 5H), 7.45 (m, 1H), 7.28 (m, 1H), 6.71 (s, 2H), 4.50 (m, 2H), 3.83 (m, 2H), 3.5 (broad s, 3H), 3.18 (m, 2H), 2.71 (m, 2H), 1.77 (m, 2H), 1.38–1.17 (m, 10H); $^{13}$C NMR (75 MHz, DMSO-$d_6$) 151.7, 151.3, 144.0, 141.0, 132.8, 132.6, 129.5, 127.0, 126.8, 125.9, 121.9, 120.4, 114.9, 70.5, 58.5, 45.3, 42.8, 30.0, 29.2, 28.8, 28.7, 27.5, 26.2, 26.1; MS m/z 510 (M+H).

EXAMPLE 243
N-{8-[4-Amino-2-(2-methoxyethyl)-1H-imidazo[4,5-c]quinolin-1-yl]octyl}methanesulfonamide

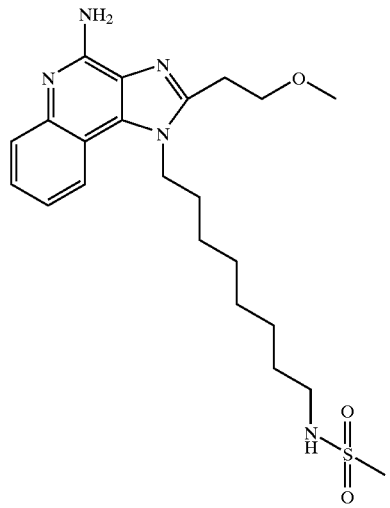

Using the general method of Example 242, 1-(8-aminooctyl)-2-(2-methoxyethyl)-1H-imidazo[4,5-c]quinolin-4-amine (800 mg, 2.17 mmol) was reacted with methanesulfonyl chloride (172 μL, 2.17 mmol) to provide 720 mg of N-{8-[4-amino-2-(2-methoxyethyl)-1H-imidazo[4,5-c]quinolin-1-yl]octyl}methanesulfonamide as a yellow powder, m.p. 109–110° C. Analysis: Calculated for $C_{22}H_{33}N_5O_3S$: %C, 59.04; %H, 7.43; %N, 15.65; Found: %C, 58.78; %H, 7.38; %N, 15.48.

$^1$H NMR (300 MHz, DMSO-$d_6$) δ 8.01 (d, J=8.3 Hz, 1H), 7.62 (d, J=8.3 Hz, 1H), 7.42 (m, 1H), 7.26 (m, 1H), 6.91 (m, 1H), 6.51 (s, 2H), 4.51 (t, J=7.3 Hz, 2H), 3.83 (t, J=6.8 Hz), 2H), 3.34 (s, 3H), 3.18 (t, J=6.8 Hz, 2H), 2.89 (m, 2H), 2.86 (s, 3H), 1.80 (m, 2), 1.27 (m, 10H);

$^{13}$C NMR (125 MHz, DMSO-$d_6$) 152.0, 151.0, 145.0, 132.6, 132.6, 126.7, 126.6, 121.56, 120.3, 115.1, 70.5, 58.5, 45.3, 42.8, 30.0, 29.7, 28.9, 28.8, 27.5, 26.4, 26.2; MS m/z 448 (M+1).

EXAMPLE 244

N-[8-(4-Amino-2-butyl-1H-imidazo[4,5-c]quinolin-1-yl)octyl]methanesulfonamide

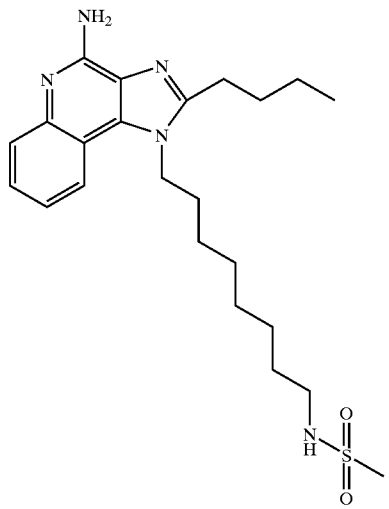

Using the general method of Example 242, 1-(8-aminooctyl)-2-butyl-1H-imidazo[4,5-c]quinolin-4-amine (1.2 g, 3.26 mmol) was reacted with methanesulfonyl chloride (260 μL, 3.26 mmol) to provide 0.70 g of N-[8-(4-amino-2-butyl-1H-imidazo[4,5-c]quinolin-1-yl)octyl]methanesulfonamide as a tan powder, m.p. 121–124° C. Analysis: Calculated for $C_{23}H_{35}N_5O_3S$: %C, 61.99: %H, 7.92; %N, 15.72; Found: %C, 62.01; %H, 7.97; %N, 15.75.

$^1$H NMR (300 MHz, DMSO-$d_6$) δ 8.01 (d, J=8.3 Hz, 1H), 7.61 (dd, J=8.3, 1.0 Hz, 1H), 7.41 (dt, J=8.3 1.5 Hz, 1H), 7.25 (dt, J=8.3, 1.5 Hz, 1H), 6.91 (t, J=4.9 Hz, 1H), 6.47 (s, 2H), 4.48 (t, J=7.3 Hz, 2H), 2.90 (m, 4H), 2.86 (s, 3H), 1.80 (m, 4H), 1.44 (m, 6H), 1.27 (m, 6H), 0.96 (t, J=7.3 Hz, 3H); $^{13}$C NMR (500 MHz, DMSO-$d_6$) 153.3, 152.1, 145.1, 132.5, 126.8. 126.7, 126.6, 121.5, 120.2, 115.2, 45.1, 42.8, 39.6, 30.1, 30.0, 29.8, 28.9, 28.8, 26.5, 26.4, 26.2, 22.3, 14.1; MS m/z 446 (M+1).

EXAMPLE 245

N-[3-(4-Amino-2-butyl-1H-imidazo[4,5-c]quinolin-1-yl)propyl]-5-(dimethylamino)naphthalene-1-sulfonamide

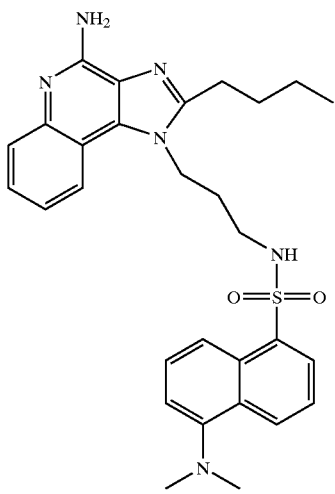

Under a nitrogen atmosphere triethylamine (765 mg, 7.56 mmol) was added to a solution of 1-(3-aminopropyl)-2-butyl-1H-imidazo[4,5-c]quinolin-4-amine (1.5 g, 5.04 mmol) in 1-methyl-2-pyrrolidinone (75 mL). A solution of 5-dimethylamino-1-naphthalenesulfonyl chloride (1.5 g, 5.55 mmol) in 1-methyl-2-pyrrolidinone was added. The reaction was monitored by HPLC. The reaction mixture was combined with water (500 mL) and the pH was adjusted to 10 with solid potassium carbonate. The resulting yellow precipitate was isolated by filtration, rinsed with water and then purified by column chromatography (silica gel eluting with 1–5% methanol in chloroform). The purified material was recrystallized from acetonitrile to provide 1.76 g of N-[3-(4-amino-2-butyl-1H-imidazo[4,5-c]quinolin-1-yl)propyl]-5-(dimethylamino)naphthalene-1-sulfonamide as a solid, m.p. 216.5–217.5° C. Analysis: Calculated for $C_{29}H_{34}N_6O_2S$: %C, 65.64; %H, 6.46; %N, 15.84; Found: %C, 65.52; %H, 6.44; %N, 15.90.

EXAMPLE 246

N-[3-(4-Amino-2-butyl-1H-imidazo[4,5-c]quinolin-1-yl)propyl]-4-methylbenzenesulfonamide

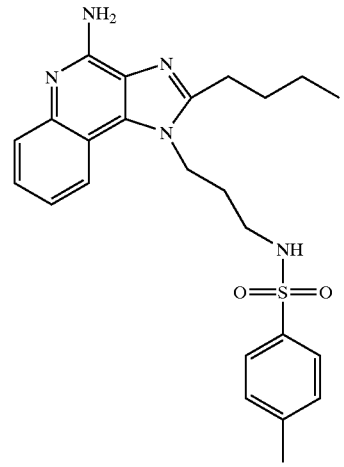

Using the general method of Example 245 1-(3-aminopropyl)-2-butyl-1H-imidazo[4,5-c]quinolin-4-amine (1.5 g, 5.04 mmol) was reacted with p-toluenesulfonyl chloride (1.08 g, 5.55 mmol) to provide 1.57 g of N-[3-(4-amino-2-butyl-1H-imidazo[4,5-c]quinolin-1-yl)propyl]-4-methylbenzenesulfonamide as an off white powder, m.p. 197.0–198.5° C. Analysis: Calculated for $C_{24}H_{29}N_5O_2S$: %C, 63.83; %H, 6.47; %N, 15.51; Found: %C, 63.68; %H, 6.40; %N, 15.51.

EXAMPLE 247

N-{3-[4-Amino-2-(2-methoxyethyl)-1H-imidazo[4,5-c]quinolin-1-yl]propyl}methanesulfonamide

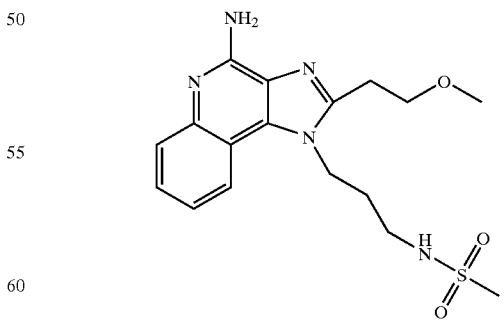

Using the general method of Example 242, 1-(3-aminopropyl)-2-(2-methoxyethyl)-1H-imidazo[4,5-c]quinolin-4-amine (1.53 g, 5.11 mmol) was reacted with methanesulfonyl chloride to provide 800 mg of N-{3-[4-amino-2-(2-methoxyethyl)-1H-imidazo[4,5-c]quinolin-1- yl]propyl}methanesulfonamide as light yellow needles, m.p. 193–194° C. Analysis: Calculated for C₁₇H₂₃N₅O₃S: %C, 54.09; %H, 6.14; %N, 18.55; Found: %C, 54.09; %H, 5.93; %N, 18.49.

EXAMPLE 248

N-[8-(4-Amino-2-butyl-1H-imidazo[4,5-c]quinolin-1-yl)octyl]benzenesulfonamide

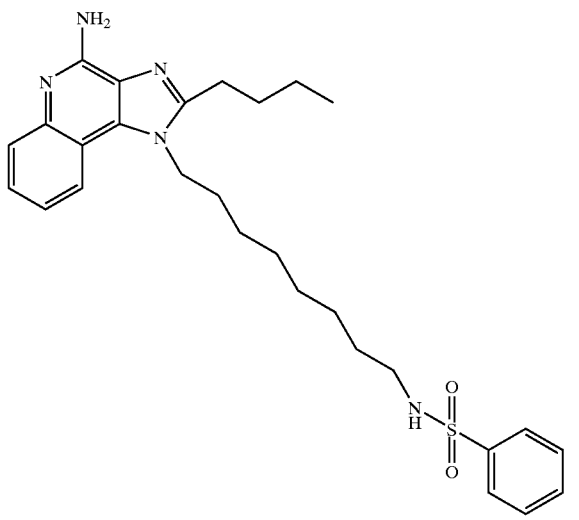

Using the general method of Example 242, 1-(8-aminooctyl)-2-butyl-1H-imidazo[4,5-c]quinolin-4-amine (1.0 g, 2.72 mmol) was reacted with benzenesulfonyl chloride (350 µL, 2.72 mmol) to provide 1.38 g of N-[8-(4-amino-2-butyl-1H-imidazo[4,5-c]quinolin-1-yl)octyl]benzenesulfonamide as an off white powder, m.p. 143–144° C. Analsysis: Calculated for C₂₈H₃₇N₅O₂S: %C, 66.24; %H, 7.35; %N, 13.79; Found: %C, 66.08; %H, 7.25; %N, 13.72. Karl Fisher titration found 0.23% water.

¹H NMR (300 MHz, DMSO-d₆) δ 7.98 (d, J=7.8 Hz, 1H), 7.77 (m, 2H), 7.62–7.53 (m, 5H), 7.41 (m, 1H), 7.25 (m, 1H), 6.47 (s, 2H), 4.47 (m, 2H), 2.90 (m, 2H), 2.70 (q, J=6.3 Hz, 2H), 1.78 (m, 4H), 1.49–1.17 (m, 12H), 0.95 (t, J=7.3, 3H); ¹³C NMR (125 MHz, DMSO-d₆) 153.3, 152.0, 145.0, 141.0, 132.5, 129.5, 126.82, 126.76, 126.7, 126.6, 121.5, 120.3, 120.2, 115.1, 45.1, 42.8, 30.0, 29.2, 28.8, 28.7, 26.5, 26.2, 26.1, 22.3, 14.2, 14.1; MS m/z 507 (M+1).

EXAMPLE 249

N-{3-[4-Amino-2-(2-methoxyethyl)-1H-imidazo[4,5-c]quinolin-1-yl]propyl}benzenesulfonamide

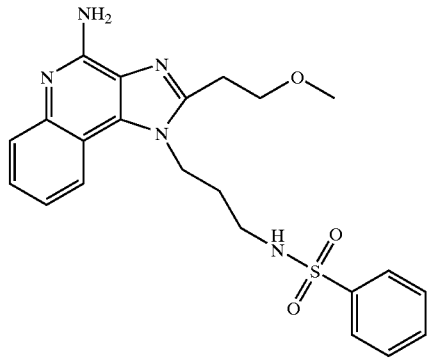

Using the general method of Example 242, 1-(3-aminopropyl)-2-(2-methoxyethyl)-1H-imidazo[4,5-c]quinolin-4-amine (1.53 g, 5.11 mmol) was reacted with benzenesulfonyl chloride (993 mg, 5.62 mmol) to provide 1.37 g of N-{3-[4-amino-2-(2-methoxyethyl)-1H-imidazo[4,5-c]quinolin-1-yl]propyl}benzenesulfonamide as a white powder, m.p. 149–151° C. Analysis: Calculated for C₂₂H₂₅N₅O₃S: %C, 60.12; %H, 5.73; %N, 15.93; Found: %C, 60.40; %H, 5.82; %N, 15.85.

EXAMPLE 250

N-[4-(4-Amino-2-pentyl-1H-imidazo[4,5-c]quinolin-1-yl)butyl]methanesulfonamide

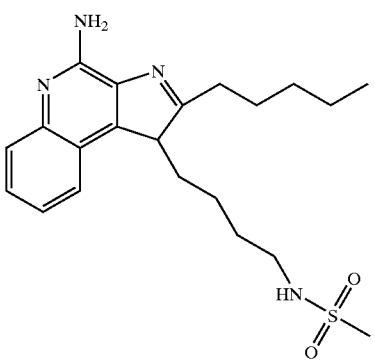

Using the general method of Example 245, 1-(4-aminobutyl)-2-pentyl-1H-imidazo[4,5-c]quinolin-4-amine (1.50 g, 4.6 mmol) was reacted with methanesulfonyl chloride (0.57 mL, 7.4 mmol) to provide 636 mg of N-[4-(4-amino-2-pentyl-1H-imidazo[4,5-c]quinolin-1-yl)butyl]methanesulfonamide as an off white solid, m.p. 136.8–138.1° C. Analysis: Calculated for C₂₀H₂₉N₅O₂S: %C, 59.53; %H, 7.24; %N, 17.35; Found: %C, 59.50; %H, 7.31; %N, 16.80.

EXAMPLE 251

N-[4-(4-Amino-2-pentyl-1H-imidazo[4,5-c]quinolin-1-yl)butyl]benzenesulfonamide

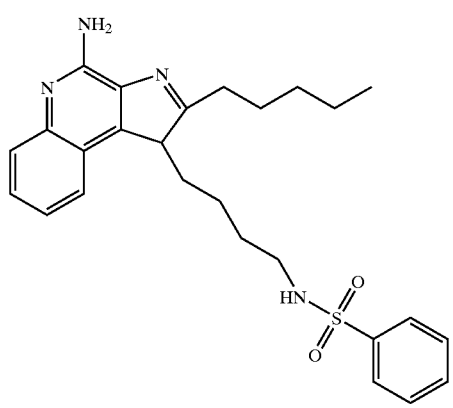

Using the general method of Example 232, 1-(4-aminobutyl)-2-pentyl-1H-imidazo[4,5-c]quinolin-4-amine (1.00 g, 3.1 mmol) was reacted with benzenesulfonyl chloride (0.51 mL, 4.0 mmol) to provide 0.35 g of N-[4-(4-amino-2-pentyl-1H-imidazo[4,5-c]quinolin-1-yl)butyl]benzenesulfonamide as a yellow crystalline solid. Analysis: Calculated for C₂₅H₃₁N₅O₂S.0.5 H₂O: %C, 63.27; %H, 6.80; %N, 14.76; Found: %C, 62.99; %H, 6.61; %N, 14.42.

EXAMPLE 252

N-[8-(4-Amino-1H-imidazo[4,5-c]quinolin-1-yl)octyl]methanesulfonamide

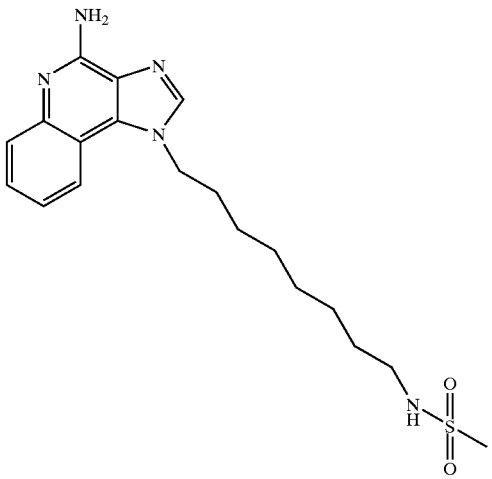

Using the general method of Example 242, 1-(8-aminooctyl)-1H-imidazo[4,5-c]quinolin-4-amine (3.85 mmol) was reacted with methanesulfonyl chloride (310 μL, 3.85 nmmol) to provide 0.43 g of N-{8-[4-amino-1H-imidazo[4,5-c]quinolin-1-yl]octyl}methanesulfonamide as an off white powder, m.p. 153–155° C. Analysis: Calculated for $C_{19}H_{27}N_5O_2S$: %C, 58.59; %H, 6.99; %N, 17.98; %S, 8.23; Found: %C, 58.40; %H, 6.99; %N, 17.71; %S, 8.14.

$^1$H NMR (300 MHz, DMSO-$d_6$) δ 8.20 (s, 1H), 8.03 (d, J=7.8 Hz, 1H), 7.63 (d, J=8.3 Hz, 1H), 7.45 (m, 1H), 7.27 (m, 1H), 6.91 (m, 1H), 6.63 (d, 2H), 4.59 (m, 2H), 2.89 (m, 2H), 2.86 (s, 3H), 1.86 (m, 2H), 1.41–1.25 (m, 10H); $^{13}$C NMR (125 MHz, DMSO-$d_6$) 152.5, 145.2, 143.2, 132.0, 128.5, 127.1, 126.5, 121.6, 120.8, 115.2, 46.9, 42.8, 39.6, 30.0, 29.7, 28.81, 28.78, 26.4, 26.1; MS m/z 390 (M+1).

EXAMPLE 253

N-{3-[4-Amino-2-(2-methoxyethyl)-1H-imidazo[4,5-c]quinolin-1-yl]propyl}-4-methylbenzenesulfonamide

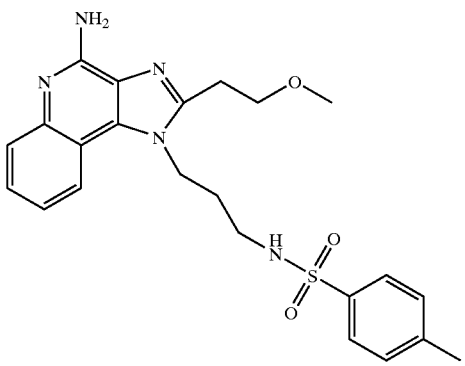

Using the general method of Example 242, 1-(3-aminopropyl)-2-(2-methoxyethyl)-1H-imidazo[4,5-c]quinolin-4-amine (1.53 g, 5.11 mmol) was reacted with p-toluenesulfonyl chloride (1.07 g, 5.62 mmol) to provide 750 mg of N-{3-[4-amino-2-(2-methoxyethyl)-1H-imidazo[4,5-c]quinolin-1-yl]propyl}-4-methylbenzenesulfonamide as a solid, m.p. 189–191° C. Analysis: Calculated for $C_{23}H_{27}N_5O_3S.0.50 H_2O$: %C, 59.72; %H, 6.10; %N, 15.14; Found: %C, 59.73; %H, 5.95; %N, 15.08.

EXAMPLE 254

N-[4-(4-Amino-2-pentyl-6,7,8,9-tetrahydro-1H-imidazo[4,5-c]quinolin-1-yl)butyl]methanesulfonamide

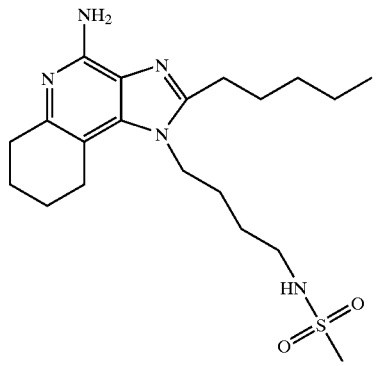

A solution of 1-(4-aminobutyl)-2-pentyl-6,7,8,9-tetrahydro-1H-imidazo[4,5-c]quinolin-4-amine (1.50 g, 3.7 mmol) in chloroform (150 mL) was chilled in an acetone/ice bath. Methanesulfonic anhydride (0.79 g, 3.7 mmol) was slowly added. After 1.75 hr, 0.018 g of anhydride was added. At 2.5 hrs 0.079 g of anhydride was added. After 3 hrs, the reaction mixture was washed with aqueous 1% sodium carbonate solution (3×150 mL). The organic layer was dried over magnesium sulfate and then concentrated under reduced pressure to provide 2.2 g of a light yellow residue. The residue was combined with aqueous 1% sodium carbonate solution (200 mL) and the pH was adjusted to 13 by the addition of solid sodium carbonate and 50% sodium hydroxide. The organic phase was separated, washed with aqueous 1% sodium carbonate solution (3×200 mL), dried over magnesium sulfate and then concentrated under reduced pressure to provide 2.18 g of a brown residue. This material was slurried with methyl acetate. The resulting solid was isolated to provide 1.25 g of N-[4-(4-amino-2-pentyl-6,7,8,9-tetrahydro-1H-imidazo[4,5-c]quinolin-1-yl)butyl]methanesulfonamide as a white solid, m.p. 167.0–167.8° C. Analysis: Calculated for $C_{20}H_{33}N_5O_2S$: %C, 58.94; %H, 8.16; %N, 17.18; Found: %C, 58.79; %H, 7.92; %N, 17.02.

EXAMPLE 255

N-{3-[4-amino-2-(ethoxymethyl)-1H-imidazo[4,5-c]quinolin-1-yl]propyl}methanesulfonamide

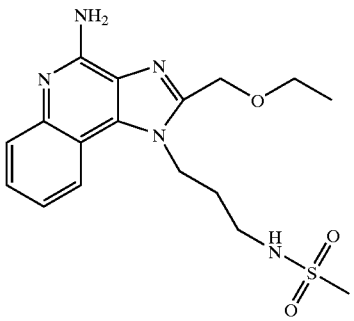

A mixture of 1-(3-aminopropyl)-2-(ethoxymethyl)-1H-imidazo[4,5-c]quinolin-4-amine (2.0 g, 6.7 mmol), triethylamine (1.5 mL, 15 mmol) and acetonitrile (75 mL) was heated until a solution was obtained. Methanesulfonic anhydride (1.28 g, 7.4 mmol) was added in a single portion. After 5 minutes a small amount of anhydride was added. The reaction mixture was allowed to stir overnight. The reaction mixture was quenched with aqueous 1% sodium carbonate solution. The aqueous layer was extracted with chloroform. The organics were dried over magnesium sulfate, filtered and then concentrated under reduced pressure. The residue was dried under high vacuum for 3 hours to provide 2.73 g of a glassy solid. This material was recrystallized from methanol to provide 1.38 g of N-{3-[4-amino-2-(ethoxymethyl)-1H-imidazo[4,5-c]quinolin-1-yl]propyl}methanesulfonamide, m.p. 208.2–209.6° C. Analysis: Calculated for $C_{17}H_{23}N_5O_3S$: %C, 54.09; %H, 6.14; %N, 18.55; Found: %C, 53.97; %H, 6.29; %N, 18.32.

EXAMPLE 256

N-{3-[4-Amino-2-(2-methoxyethyl)-1H-imidazo[4,5-c]quinolin-1-yl]-2,2-dimethylpropyl}methanesulfonamide

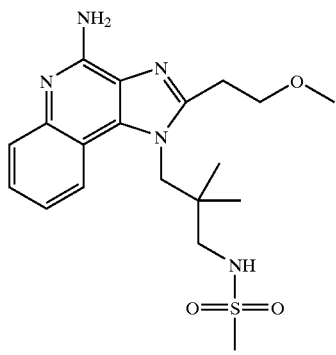

Using the general method of Example 242, 1-(3-amino-2,2-dimethylpropyl)-2-(2-methoxyethyl)-1H-imidazo[4,5-c]quinolin-4-amine (0.22 g, 0.672 mmol) was reacted with methanesulfonyl chloride (125 μL) to provide 270 mg of N-{3-[4-amino-2-(2-methoxyethyl)-1H-imidazo[4,5-c]quinolin-1-yl]-2,2-dimethylpropyl}methanesulfonamide as a cream colored powder, m.p. 204.0–206.0° C. Analysis: Calculated for $C_{19}H_{27}N_5O_3S \cdot 0.50 H_2O$: %C, 55.05; %H, 6.81; %N, 16.89; %S, 7.74; Found: %C, 55.10; %H, 6.58; %N, 17.23; %S, 7.51. % $H_2O$ calculated: 2.17; found: 2.28 (Karl Fisher).

$^1$H NMR (300 MHz, DMSO-$d_6$) δ 8.36 (d, J=8.3 Hz, 1H), 7.59 (d, J=8.3 Hz, 1H), 7.38 (m, 2H), 7.20 (m, 1H), 6.49 (s, 2H), 4.81 (br s, 1H), 4.39 (br s, 1H), 3.82 (m, 2H), 3.27 (s, 3H), 3.19 (br s, 2H), 3.02 (d, J=6.8 Hz, 2H), 2.94 (s, 3H), 0.82 (br s , 6H); $^{13}$C NMR (125 MHz, DMSO-$d_6$) δ 152.5, 152.0, 145.3, 133.9, 126.8, 126.7, 126.6, 121.5, 120.7, 115.8, 71.0, 58.5, 51.8, 51.5, 39.7, 39.0, 28.3, 24.4, 23.1; MS m/z 406 (M+H).

EXAMPLE 257

N-{3-[4-Amino-2-(2-methoxyethyl)-1H-imidazo[4,5-c]quinolin-1-yl]propyl}-5-(dimethylamino)naphthalene-1-sulfonamide

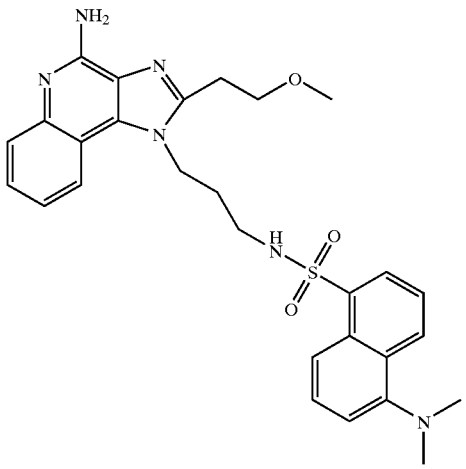

Using the general method of Example 245 except that chloroform was used as the solvent, 1-(3-aminopropyl)-2-(methoxyethyl)-1H-imidazo[4,5-c]quinolin-4-amine (1.53 g, 5.11 mmol) was reacted with 5-dimethylamino-1-naphthalenesulfonyl chloride (5.87 mmol) to provide 1.45 g of N-{3-[4-amino-2-(2-methoxyethyl)-1H-imidazo[4,5-c]quinolin-1-yl]propyl}-5-(dimethylamino)naphthalene-1-sulfonamide as a yellow solid, m.p. 210–215° C. Analysis: Calculated for $C_{28}H_{32}N_6O_3S \cdot 1.50 H_2O$: %C, 60.09; %N, 15.02; Found: %C, 59.89; %H, 6.22; %N, 14.86.

EXAMPLE 258

N-[3-(4-Amino-2-methyl-1H-imidazo[4,5-c]quinolin-1-yl)propyl]methanesulfonamide

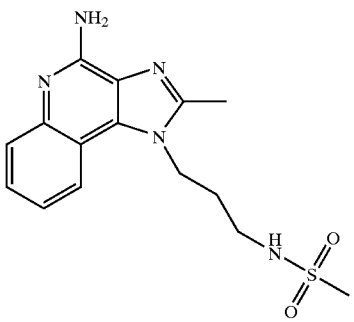

Using the general method of Example 255, 1-(3-aminopropyl)-2-methyl-1H-imidazo[4,5-c]quinolin-4-amine (2.0 g, 7.8 mmol) was reacted with methanesulfonic anhydride (1.49 g, 8.6 mmol) to provide 1.2 g of N-[3-(4-amino-2-methyl-1H-imidazo[4,5-c]quinolin-1-yl)propyl]methanesulfonamide as a solid, m.p. 236.0–238.0° C. Analysis: Calculated for $C_{15}H_{19}N_5O_2S \cdot 0.25 H_2O$: %C, 53.32; %H, 5.82; %N, 20.72; Found: %C, 53.35; %H, 5.72; %N, 20.57.

EXAMPLE 259

N-{3-[4-Amino-2-(2-methoxyethyl)-6,7,8,9-tetrahydro-1H-imidazo[4,5-c]quinolin-1-yl]propyl}methanesulfonamide

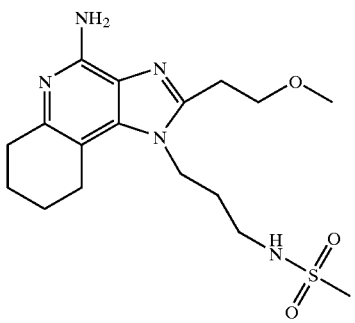

Using the general method of Example 255, 1-(3-aminopropyl)-2-(2-methoxyethyl)-6,7,8,9-tetrahydro-1H-imidazo[4,5-c]quinolin-4-amine (2.0 g, 6.6 mmol) was reacted with methanesulfonic anhydride (1.26 g, 7.3 mmol) to provide 630 mg of N-{3-[4-amino-2-(2-methoxyethyl)-6,7,8,9-tetrahydro-1H-imidazo[4,5-c]quinolin-1-yl]propyl}methanesulfonamide as a solid, m.p. 150.0–152.0° C. Analysis: Calculated for $C_{17}H_{27}N_5O_3S$: %C, 53.52; %H, 7.13; %N, 18.36; Found: %C, 53.27; %H, 7.12; %N, 18.37.

EXAMPLE 260

N-{3-[4-Amino-2-(ethoxymethyl)-6,7,8,9-tetrahydro-1H-imidazo[4,5-c]quinolin-1-yl]propyl}methanesulfonamide

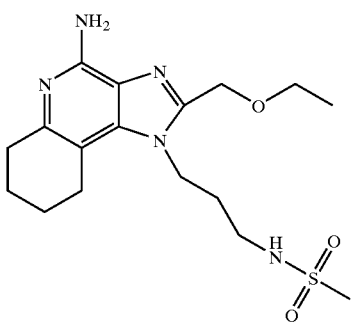

Using the general method of Example 255, except that chloroform was used in place of aceotnitrile, 1-(3-aminopropyl)-2-(2-ethoxymethyl)-6,7,8,9-tetrahydro-1H-imidazo[4,5-c]quinolin-4-amine (2.6 g, 8.35 mmol) was reacted with methanesulfonic anhydride (3+g) to provide 850 mg of N-{3-[4-amino-2-(2-ethoxymethyl)-6,7,8,9-tetrahydro-1H-imidazo[4,5-c]quinolin-1-yl]propyl}methanesulfonamide as a solid, m.p. 212.0–214.0° C. Analysis: Calculated for $C_{17}H_{27}N_5O_3S$: %C, 53.52; %H, 7.13; %N, 18.36; Found: %C, 53.25; %H, 7.16; %N, 18.09.

EXAMPLE 261

N-{3-[4-Amino-2-(3-phenoxypropyl)-1H-imidazo[4,5-c]quinolin-1-yl]propyl}methanesulfonamide

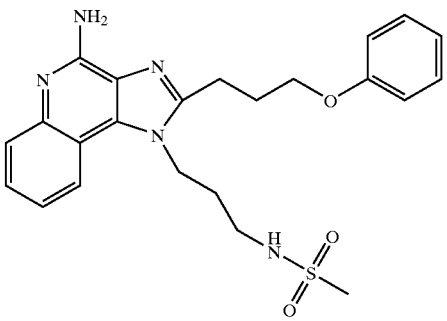

Using the general method of Example 242, except that chloroform was used in place of dichloromethane, 1-(3-aminopropyl)-2-(3-phenoxypropyl)-1H-imidazo[4,5-c]quinolin-4-amine (2.00 g, 5.32 mmol) was reacted with methanesulfonyl chloride (3+g) to provide 1.38 g of N-{3-[4-amino-2-(3-phenoxypropyl)-1H-imidazo[4,5-c]quinolin-1-yl]propyl}methanesulfonamide as a solid, m.p. 176–178° C. Analysis: Calculated for $C_{23}H_{27}N_5O_3S$: %C, 60.91; %H, 6.00; %N, 15.44; Found: %C, 60.71; %H, 5.98; %N, 15.45.

EXAMPLE 262

N-{4-[4-Amino-2-(3-phenoxypropyl)-1H-imidazo[4,5-c]quinolin-1-yl]butyl}methanesulfonamide

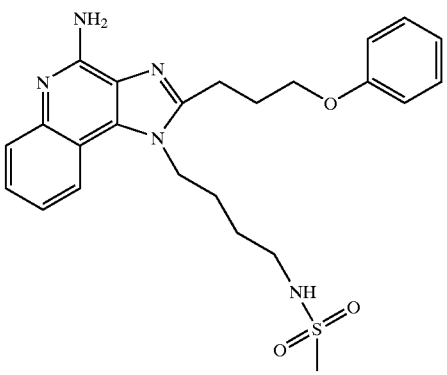

Using the general method of Example 255, except that pyridine was used in place of acetonitrile, 1-(3-aminobutyl)-2-(3-phenoxypropyl)-1H-imidazo[4,5-c]quinolin-4-amine (2.00 g, 5.1 mmol) was reacted with an excess of methanesulfonic anhydride to provide 1.36 g of N-{4-[4-amino-2-(3-phenoxypropyl)-1H-imidazo[4,5-c]quinolin-1-yl]butyl}methanesulfonamide as a solid, m.p. 156.4–157.1° C. Analysis: Calculated for $C_{24}H_{29}N_5O_3S$: %C, 60.48; %H, 6.34; %N, 14.69; Found: %C, 60.75; %H, 6.36; %N, 14.31.

EXAMPLE 263

N-[4-(4-Amino-2-methyl-6,7,8,9-tetrahydro-1H-imidazo[4,5-c]quinolin-1-yl)butyl]methanesulfonamide Hydrochloride

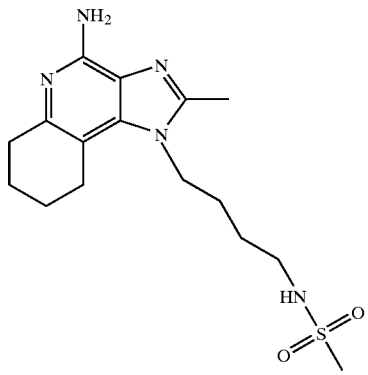

Using the general method of Example 254, 1-(4-aminobutyl)-2-methyl-6,7,8,9-tetrahydro-1H-imidazo[4,5-c]quinolin-4-amine (1.00 g, 3.7 mmol) was reacted with methanesulfonic anhydride (0.96 g, 5.5 mmol) in the presence of triethylamine (0.76 mL, 5.5 mmol) to provide 0.55 g of the free base of the desired product. This material was combined with methanol (~20 mL), warmed, allowed to cool to ambient temperature and then filtered to remove some insoluble material. The filtrate was reduced to a volume of ~10 mL and then combined with 1N hydrochloric acid (3 mL). Diethyl ether (15 mL) was added and then the mixture was concentrated under reduced pressure. The resulting residue was slurried with isopropyl alcohol to provide a white solid which was isolated by filtration and then dried to provide 0.46 g of N-[4-(4-amino-2-methyl-6,7,8,9-tetrahydro-1H-imidazo[4,5-c]quinolin-1-yl)butyl]methanesulfonamide hydrochloride, m.p. >250° C. Analysis: Calculated for $C_{16}H_{25}N_5O_2S \cdot 1.00$ HCl$\cdot 1.00$ $H_2O$: %C, 47.34; %H, 6.95; %N, 17.25; Found: %C, 47.40; %H, 6.49; %N, 17.22.

EXAMPLE 264

N-[2-(4-Amino-2-butyl-1H-imidazo[4,5-c]quinolin-1-yl)ethyl]-4-methylbenzenesulfonamide

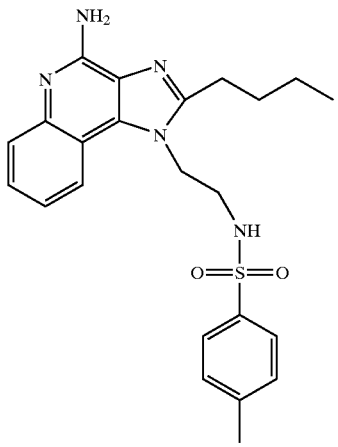

Triethylamine (1.1 g, 15.9 mmol) was added to a cooled (0° C.) solution of 1-(2-aminoethyl)-2-butyl-1H-imidazo[4,5-c]quinolin-4-amine (3.0 g, 10.6 mmol) in 1-methyl-2-pyrrolidinone (100 mL). A solution of tosyl chloride (2.11 g, 11.1 mmol) in 1-methyl-2-pyrrolidinone (20 mL) was slowly added in a dropwise fashion. The reaction was allowed to warm to ambient temperature and was maintained overnight. The reaction was poured into water (1500 mL) and adjusted to pH 9. A white precipitate was isolated by filtration and then recrystallized from acetonitrile (60 mL) to provide 3.9 g of N-[2-(4-amino-2-butyl-1H-imidazo[4,5-c]quinolin-1-yl)ethyl]-4-methylbenzenesulfonamide, m.p. 187.0–188.0° C. Analysis: Calculated for $C_{23}H_{27}N_5O_2S \cdot 0.3$ $H_2O$: %C, 62.29; %H, 6.28; %N, 15.79; Found: %C, 62.52; %H, 6.36; %N, 15.88.

EXAMPLE 265

N-[2-(4-Amino-2-butyl-1H-imidazo[4,5-c]quinolin-1-yl)ethyl]methanesulfonamide

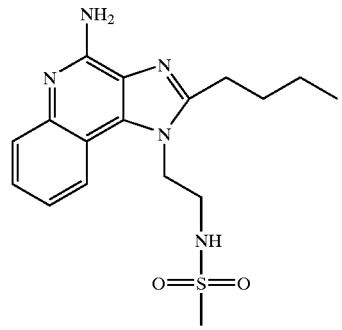

Methanesulfonyl chloride (1.27 g, 11.1 mmol) was slowly added to a solution of 1-(2-aminoethyl)-2-butyl-1H-imidazo[4,5-c]quinolin-4-amine (3.0 g, 10.6 mmol) in pyridine (60 mL). The reaction was maintained at ambient temperature overnight and then it was concentrated to dryness. The residue was combined with warm dichloroethane and water and then filtered to provide an off white solid. The dichloroethane layer was concentrated to provide an off white solid. The two solids were combined and then recrystallized from N,N-dimethylformamide to provide 1.1 g of N-[2-(4-amino-2-butyl-1H-imidazo[4,5-c]quinolin-1-yl)ethyl]methanesulfonamide as a white solid, m.p. 210.0–211.0° C. Analysis: Calculated for $C_{17}H_{23}N_5O_2S$: %C, 56.49; %H, 6.41; %N, 19.37; Found: %C, 56.45; %H, 6.49; %N, 19.50.

EXAMPLE 266

1-[4-(1,1-dioxidoisothiazolidin-2-yl)butyl]-2-(2-methoxyethyl)-1H-imidazo[4,5-c]quinolin-4-amine

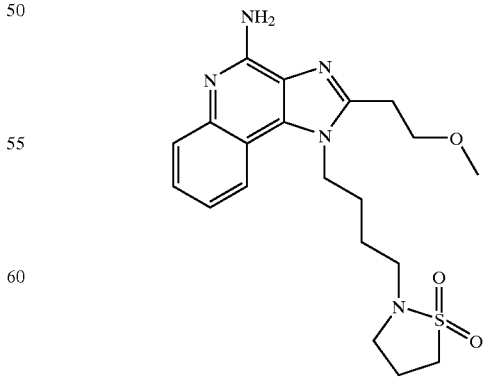

Under a nitrogen atmosphere, 1-(4-aminobutyl)-2-(2-methoxyethyl)-1H-imidazo[4,5-c]quinolin-4-amine (500 mg, 1.6 mmol) was dissolved in dichloromethane (5 mL) and triethylamine (0.33 mL, 2.4 mmol). 3-Chloropropylsulfonyl chloride (0.19 mL, 1.6 mmol) was added dropwise and the reaction was stirred for 2 hours. The solvent was removed in vacuo. The residue was dissolved in N,N-dimethylformamide (5 mL) and 1,8-diazabicyclo[5.4.0]undec-7-ene (0.48 mL, 3.2 mmol) was added. The reaction was stirred for 72 hours and then poured into water and extracted with dichloromethane. The organic layer was washed with water followed by brine; dried (Na$_2$SO$_4$); decanted and evaporated to yield crude product as a brown oil. Purification involved flash column chromatography (silica gel, gradient elution with methanol/dichloromethane 100:0 to 94:6) followed by recrystallization from acetonitrile to provide 289 mg of 1-[4-(1,1-dioxidoisothiazolidin-2-yl)butyl]-2-(2-methoxyethyl)-1H-imidazo[4,5-c]quinolin-4-amine as a yellow crystalline solid, m.p. 156.4–157.7° C.

$^1$H-NMR (500 MHz, DMSO-d$_6$) δ 8.04 (d, J=7.4 Hz, 1H), 7.62 (dd, J=8.3, 1.2 Hz, 1H); 7.42 (ddd, J=8.2, 7.0, 1.2 Hz, 1H), 7.26 (ddd, J=8.2, 7.0, 1.2 Hz, 1H), 6.48 (bs, 2H), 4.54 (t, J=7.6 Hz, 2H), 3.84 (t, J=6.7 Hz, 2H), 3.29 (s, 3H), 3.22–3.12 (t, J=6.6 Hz, 2H), 2.23–2.13 (m, 2H), 1.90–1.65 (m, 4H); $^{13}$C-NMR (125 MHz, DMSO-d$_6$) δ 151.6, 150.6, 144.8, 132.2, 126.5, 126.3, 121.2, 120.0, 114.7, 70.2, 58.1, 46.5, 46.1, 44.5, 43.6, 27.1, 24.1, 18.3; Anal calcd for C$_{20}$H$_{27}$N$_5$O$_3$S: %C, 57.53; %H, 6.52; %N, 16.77; %S, 7.68. Found: %C, 57.52; %H, 6.67; %N, 16.88; %S, 7.71.

EXAMPLE 267

2-butyl-1-[4-(1,1-dioxidoisothiazolidin-2-yl)butyl]-1H-imidazo[4,5-c]quinolin-4-amine

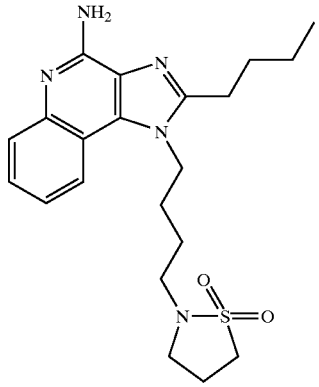

Using the general method of Example 266 except that 1-methyl-2-pyrrolidinone was used in place of dichloromethane, 1-(4-aminobutyl)-2-butyl-1H-imidazo[4,5-c]quinolin-4-amine (5.0 g, 16.0 mmol) was reacted with 3-chloropropanesulfonyl choride (2.83 g, 16.0 mmol) to provide 0.75 g of 2-butyl-1-[4-(1,1-dioxidoisothiazolidin-2-yl)butyl]-1H-imidazo[4,5-c]quinolin-4-amine as a white solid, m.p. 173.0–176.0° C.

1H-NMR (300 MHz, DMSO-d$_6$) δ 8.30 (d, J=8.1 Hz, 1H), 7.62 (d, J=8.2 Hz, 1H), 7.41 (t, J=7.6 Hz, 1H), 7.26 (t, J=8.0 Hz, 1H), 6.48 (bs, 2H), 4.51 (t, J=7.5 Hz, 2H), 3.18–3.11 (m, 4H), 2.96–2.89 (m, 4H), 2.22–2.12 (m, 2H), 1.92–1.63 (m, 6H), 1.45 (sextet, J=7.4 Hz, 2H), 0.96 (t, J=7.3 Hz, 3H); $^{13}$C-NMR (75 MHz, DMSO-d$_6$) δ 153.0, 151.7, 144.7, 132.2, 126.4, 126.2, 121.1, 120.0, 114.7, 46.5, 46.1, 44.3, 43.6, 29.7, 27.1, 26.1, 24.1, 22.0, 18.3, 13.8; MS (CI) m/e 416.2124 (416.2120 calcd for C$_{21}$H$_{30}$N$_5$O$_2$S, M+H); Anal calcd for C$_{21}$H$_{29}$N$_5$O$_2$S: %C, 60.70; %H, 7.03; %N, 16.85; %S, 7.72. Found: %C, 60.67; %H, 6.94; %N, 17.02; %S, 7.42.

EXAMPLE 268

N-{2-[4-Amino-2-(ethoxymethyl)-1H-imidazo[4,5-c]quinolin-1-yl]-1,1-dimethylethyl}methanesulfonamide

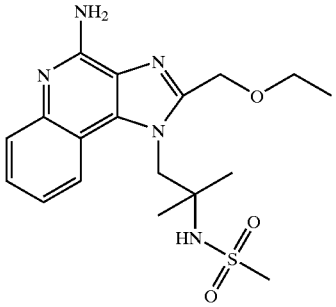

Part A

A stirred solution of 4-chloro-3-nitroquinoline (17.3 g, 83.2 mmol) in 200 mL of anhydrous CH$_2$Cl$_2$, under N$_2$, was treated with triethylamine (23.2 mL, 166.4 mmol) and 1,2-diamino-2-methylpropane (9.57 mL, 91.5 mmol). After stirring overnight, the reaction mixture was diluted with 800 mL of CHCl$_3$ washed with H$_2$O (3×300 mL) and brine (300 mL). The organic portion was dried over Na$_2$SO$_4$ and concentrated to give 2-methyl-N$^1$-(3-nitroquinolin-4-yl)propane-1,2-diamine (21.0 g) as a bright yellow solid.

Part B

A solution of 2-methyl-N$^1$-(3-nitroquinolin-4-yl)propane-1,2-diamine (2.60 g, 10.0 mmol) in 50 mL of THF, under N$_2$, was cooled to 0° C. and treated with 10 mL of 1N NaOH solution. Di-tert-butyl dicarbonate (2.18 g, 10.0 mmol) was then added to the rapidly stirred solution. The reaction mixture was then allowed to warm to ambient temperature and was stirred overnight. An additional 400 mg of di-tert-butyl dicarbonate was added and stirring was continued for 3 d. The reaction was then treated with ethyl acetate (200 mL) and washed with H$_2$O (2×) and brine. The organic portion was dried over Na$_2$SO$_4$ and concentrated to give a yellow solid that was titurated with 10% EtOAc/hexanes. The solid was isolated by filtration and dried under vacuum overnight to give tert-butyl 1,1-dimethyl-2-[(3-nitroquinolin-4-yl)amino]ethylcarbamate (2.80 g) as a yellow powder.

Part C

A solution of tert-butyl 1,1-dimethyl-2-[(3-nitroquinolin-4-yl)amino]ethylcarbamate (3.50 g, 9.72 mmol), in 150 mL of toluene was treated with 0.3 g of 5% Pt on carbon and shaken under H$_2$ (3 atm, 3 Kg/cm$^2$) for 6 h. The solution was then filtered through a Celite pad and concentrated to give 3.04 g of crude tert-butyl 2-[(3-aminoquinolin-4-yl]-1,1-dimethylethylcarbamate as a light orange foam.

Part D

A solution of tert-butyl 2-[(3-aminoquinolin-4-yl]-1,1-dimethylethylcarbamate (3.04 g, 9.21 mmol) in 50 mL of CH$_2$Cl$_2$ was cooled to 0° C. and treated with triethylamine (1.41 mL, 10.13 mmol) and ethoxyacetyl chloride (1.02 mL, 10.17 mmol). After 2 h, the reaction mixture was concentrated under reduced pressure. The resulting syrup was taken up in 100 mL of EtOH and treated with 4.5 mL of triethylamine. The solution was heated to reflux overnight. The reaction mixture was concentrated and taken up in 100 mL of CH$_2$Cl$_2$ and washed with H$_2$O (2×) and brine. The organic portion was dried over Na$_2$SO$_4$ and concetrated. The resulting syrup was purified by column chromatography (SiO$_2$, 80% EtOAc/hexanes) to give tert-butyl 2-[2-(ethoxymethy)-

1H-imidazo[4,5-c]quinolin-1-yl]-1,1-dimethylethylcarbamate (1.57 g) as a peach colored foam.

Part E

A solution of tert-butyl 2-[2-(ethoxymethy)-1H-imidazo[4,5-c]quinolin-1-yl]-1,1-dimethylethylcarbamate (1.57 g, 3.94 mmol) in 30 mL of CH₂Cl₂ was treated with 3-chloroperoxybenzoic acid (77%, 1.01 g, 4.57 mmol). After stirring for 2 h, the reaction mixture was treated with 30 mL of additional CH₂Cl₂ and was washed with 1% Na₂CO₃ solution (2×30 mL), H₂O and brine. The organic portion was then dried over Na₂SO₄ and concentrated to give tert-butyl 2-[2-(2-(ethoxymethyl)-5-oxido-1H-imidazo[4,5-c]quinolin-1-yl]-1,1-dimethylethylcarbamate (1.58 g) as a light brown foam.

Part F

A solution of tert-butyl 2-[2-(2-(ethoxymethyl)-5-oxido-1H-imidazo[4,5-c]quinolin-1-yl]-1,1-dimethylethylcarbamate (1.57 g, 3.79 mmol) in 20 mL of 1,2-dichloroethane was heated to 70° C. and treated with 2 mL of concentrated NH₄OH solution. To the rapidly stirred solution was added solid p-toluenesulfonyl chloride (795 mg, 4.17 mmol). The reaction mixture was then sealed in a pressure vessel and heating was continued for 2 h. The reaction mixture was then cooled and treated with 50 mL of CHCl₃. The reaction mixture was then washed with H₂O, 1% Na₂CO₃ solution (3×) and brine. The organic portion was dried over Na₂SO₄ and concentrated to give the product as a light brown oil. The resulting oil was purified by column chromatography (SiO₂, 2–5% MeOH/CHCl₃) to give tert-butyl 2-[4-amino-2-(ethoxymethyl)-1H-imidazo[4,5-c]quinolin-1-yl]-1,1-dimethylethylcarbamate (1.26 g) as a light yellow foam.

Part G

Tert-butyl 2-[4-amino-2-(ethoxymethyl)-1H-imidazo[4,5-c]quinolin-1-yl]-1,1-dimethylethylcarbamate (1.26 g, 3.05 mmol) was dissolved in 10 mL of EtOH and treated with 10 mL of 2 M HCl in EtOH. After heating at reflux for 2 h, the reaction mixture was cooled and concentrated under reduced pressure. The resulting yellow solid was dissolved in 50 mL of H₂O and extracted with CHCl₃ (20 mL). The organic layer was discarded and the aqueous portion was made basic (pH~12) by addition of concentrated NH₄OH solution. This was then extracted with CHCl₃ (4×20 mL) and the combined organic portions were dried with Na₂SO₄ and concentrated to give 1-(2-amino-2-methylpropyl)-2-(ethoxymethyl)-1H-imidazo[4,5-c]quinoline-4-amine (808 mg) as a light brown powder.

m. p. 161.0–162.0° C.; MS m/z 314 (M+H); ¹H NMR (300 MHz, d₆-DMSO) δ 8.30 (d, J=7.7 Hz, 1H), 7.59 (dd, J=1.2, 8.3 Hz, 1H), 7.40 (ddd, J=1.0, 7.2, 8.1 Hz, 1H), 7.21 (ddd, J=1.2, 7.0, 8.2 Hz, 1H), 6.57 (s, 2H), 4.94 (br s, 2H), 4.61 (br s, 2H), 3.52 (q, J=7.0 Hz, 2H), 1.61 (s, 2H), 1.31 (t, J=7.0 Hz, 3H), 1.07 (s, 6H); ¹³C NMR (75 MHz, d₆-DMSO) δ 152.4, 151.1, 145.7, 134.3, 126.8, 126.7, 121.7, 120.8, 115.7, 65.6, 65.2, 55.8, 52.5, 29.2, 15.4. Anal. Calcd for C₁₇H₂₃N₅O: %C, 65.15; %H, 7.40; %N, 22.35. Found: %C, 65.04; %H, 7.52; %N, 22.07.

Part H 1-(2-Amino-2-methylpropyl)-2-(ethoxymethyl)-1H-imidazo[4,5-c]quinoline-4-amine (111 mg, 0.355 mmol) was dissolved in 5 mL of anhydrous CH₂Cl₂ and cooled to 0° C. under N₂. To the stirred solution were added Et₃N (99 μL, 0.71 mmol) and methanesulfonyl chloride (28 μL, 0.36 mmol) and the reaction was allowed to warm to ambient temperature overnight. The reaction mixture was then quenched by addition of saturated NaHCO₃ solution (5 mL). The organic layer was separated and washed with H₂O (2×5 mL) and brine, dried over Na₂SO₄ and concentrated under reduced pressure to give a tan foam. Purification by column chromatography (SiO₂, 2.5%–5% MeOH/CHCl₃) gave N-{2-[4-amino-2-(ethoxymethyl)-1H-imidazo[4,5-c]quinolin-1-yl]-1,1-dimethylethyl}methanesulfonamide (75 mg) as a white foam.

m.p. 105.0–110.0° C.; MS m/z 392 (M+H)⁺; ¹H NMR (300 MHz, CDCl₃) δ 8.06 (dd, J=1.0, 8.3 Hz, 1H), 7.79 (dd, J=1.1, 8.4 Hz, 1H), 7.51 (ddd, J=1.3, 7.0, 8.4 Hz, 1H), 7.31 (ddd, J=1.3, 7.0, 8.3 Hz, 1H), 5.90 (br s, 1H), 5.51 (br s, 2H), 4.96 (s, 2H), 4.92 (br s, 2H), 3.74 (q, J=7.0 Hz, 2H), 3.02 (s, 3H), 1.55 (br s, 6H), 1.29 (t, J=7.0 Hz, 3H); ¹³C NMR (75 MHz, CDCl₃) δ 152.0, 150.8, 145.5, 135.2, 127.8, 127.6, 127.2, 122.2, 120.6, 116.0, 67.2, 65.4, 58.4, 55.8, 45.3, 26.6, 15.3. Anal. Calcd for C₁₈H₂₅N₅O₃S.0.75H₂O: C, 53.38; %H, 6.60; %N, 17.29. Found: %C, 53.49; %H, 6.23; %N, 16.93.

EXAMPLE 269

N-[4-(4-Amino-2-methyl-1H-imidazo[4,5-c]quinolin-1-yl)butyl]ethanesulfonamide

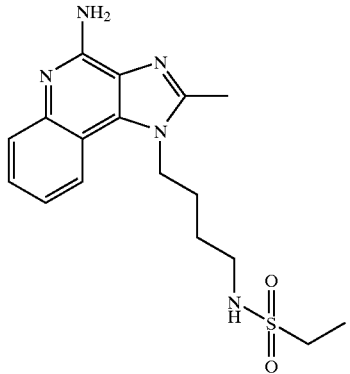

Using the general method of Example 232, 1-(4-aminobutyl)-2-methyl-1H-imidazo[4,5-c]quinolin-4-amine (1.00 g, 3.7 mmol) was reacted with ethanesulfonyl chloride (2.11 mL, 22.3 mmol) to provide 85 mg of N-[4-(4-amino-2-methyl-1H-imidazo[4,5-c]quinolin-1-yl)butyl]ethanesulfonamide as an off-white solid, m.p. 210.7–211.6° C.

EXAMPLE 270

N-{4-[4-Amino-2-(cyclopropylmethyl)-1H-imidazo[4,5-c]quinolin-1-yl]butyl}methanesulfonamide

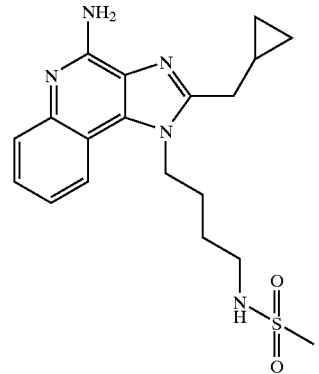

Using the general method of Example 239 Part B except that chloroform was used instead of dichloromethane, 1-(4- aminobutyl)-2-(cyclopropylmethyl)-1H-imidazo[4,5-c]quinolin-4-amine (1.00 g, 3.2 mmol) was reacted with methanesulfonic anhydride (1.29 g, 7.4 mmol) to provide 0.42 g of N-{4-[4-amino-2-(cyclopropylmethyl)-1H-imidazo[4,5-c]quinolin-1-yl]butyl}methanesulfonamide as a brown solid, m.p. 199.7–200.7° C.

CYTOKINE INDUCTION IN HUMAN CELLS

An in vitro human blood cell system was used to assess cytokine induction by compounds of the invention. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood is collected by venipuncture into EDTA vacutainer tubes from healthy human donors. Peripheral blood mononuclear cells (PBMCs) are separated from whole blood by density gradient centrifugation using Histopaque®-1077 (Sigma Chemicals, St. Louis, Mo.). The PBMCs are suspended at 3–4×10⁶ cells/mL in RPMI 1640 medium containing 10% fetal bovine serum, 2 mM L-glutamine and 1% penicillin/streptomycin solution (RPMI complete). The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells.

Incubation

The solution of test compound is added at 60 μM to the first well containing RPMI complete and serial (three fold or ten fold) dilutions are made. The PBMC suspension is then added to the wells in an equal volume, bringing the test compound concentrations to the desired range. The final concentration of PBMC suspension is 1.5–2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell culture supernatant is removed with a sterile polypropylene pipet and transferred to sterile polypropylene tubes. Samples are maintained at −30 to −70° C. until analysis. The samples are analyzed for interferon (α) and tumor necrosis factor (α) by ELISA Interferon (α) and Tumor Necrosis Factor (α) Analysis by ELISA Interferon (α) concentration is determined by ELISA using a Human Multi—Species kit from PBL Biomedical Laboratories, New Brunswick, N.J.

Tumor necrosis factor (α) (TNF)concentration is determined using ELISA kits available from Genzyme, Cambridge, Mass.; R&D Systems, Minneapolis, Minn.; or Pharmingen, San Diego, Calif.

The table below lists the lowest concentration found to induce interferon and the lowest concentration found to induce tumor necrosis factor for each compound. A "" indicates that no induction was seen at any of the tested concentrations (0.12, 0.37, 1.11, 3.33, 10 and 30 μM). A "*" indicates that no induction was seen at any of the tested concentrations (0.0001, 0.001, 0.01, 0.1, 1 and 10 μM).

Cytokine Induction in Human Cells

| Example Number | Lowest Effective Concentration (μM) | |
|---|---|---|
| | Interferon | Tumor Necrosis Factor |
| 1 | 0.12 | 3.33 |
| 2 | ** | ** |
| 3 | 0.01 | ** |
| 6 | 0.00017 | 1.11 |
| 7 | 0.01 | ** |
| 9 | 0.04 | ** |
| 11 | 0.01 | 1.11 |
| 13 | 10 | ** |
| 17 | 1.11 | 3.33 |
| 18 | 3.33 | ** |
| 19 | 0.12 | 3.33 |
| 20 | 0.12 | 3.33 |
| 21 | 1.11 | 30 |
| 22 | 0.37 | ** |
| 23 | 0.12 | 10 |
| 24 | 0.12 | 30 |
| 25 | 3.33 | ** |
| 26 | 10 | ** |
| 27 | 1.11 | 30 |
| 28 | 1.11 | 30 |
| 29 | 0.37 | 10 |
| 30 | 1.11 | ** |
| 31 | 1.11 | ** |
| 32 | 1.11 | ** |
| 33 | 1.11 | 10 |
| 34 | 0.04 | 0.37 |
| 35 | 1.11 | 10 |
| 36 | 0.0015 | 3.33 |
| 37 | 0.01 | 1.11 |
| 38 | 0.0015 | 0.37 |
| 40 | 0.0015 | 3.33 |
| 41 | 0.01 | ** |
| 42 | 0.01 | ** |
| 43 | 0.04 | ** |
| 44 | 0.0015 | 1.11 |
| 45 | 0.37 | ** |
| 46 | 0.37 | ** |
| 47 | 0.37 | ** |
| 48 | 0.37 | 10 |
| 50 | 0.12 | ** |
| 51 | 0.0015 | 0.37 |
| 52 | 0.12 | 10 |
| 53 | 0.01 | 3.33 |
| 54 | 10 | ** |
| 55 | 3.33 | ** |
| 56 | ** | ** |
| 57 | 3.33 | ** |
| 58 | 3.33 | ** |
| 59 | 3.33 | ** |
| 60 | ** | ** |
| 61 | 3.33 | ** |
| 62 | ** | ** |
| 63 | ** | ** |
| 64 | 3.33 | ** |
| 65 | 3.33 | ** |
| 66 | ** | 30 |
| 67 | 10 | ** |
| 68 | 10 | ** |
| 69 | 10 | ** |
| 70 | ** | ** |
| 71 | ** | 30 |
| 72 | 3.33 | ** |
| 73 | 0.001 | 0.1 |
| 74 | 0.001 | 0.01 |
| 75 | *** | *** |
| 76 | *** | *** |
| 77 | 0.001 | 1 |
| 78 | 0.001 | 0.1 |
| 79 | 0.01 | 1 |
| 80 | 1 | 10 |

-continued

Cytokine Induction in Human Cells

| Example Number | Lowest Effective Concentration (μM) | |
|---|---|---|
| | Interferon | Tumor Necrosis Factor |
| 81 | 0.001 | 1 |
| 82 | 0.001 | 1 |
| 83 | 0.001 | 1 |
| 84 | 1 | 10 |
| 85 | 1 | *** |
| 86 | 0.01 | 1 |
| 87 | 0.001 | 1 |
| 88 | 0.01 | 1 |
| 89 | 0.001 | 1 |
| 90 | 0.01 | 1 |
| 91 | 0.01 | 1 |
| 92 | 0.1 | 10 |
| 93 | 0.001 | 0.1 |
| 94 | 0.001 | 1 |
| 95 | 0.001 | 1 |
| 96 | 1 | *** |
| 97 | 0.1 | 10 |
| 98 | 1 | *** |
| 99 | 0.1 | 10 |
| 100 | 0.01 | 10 |
| 101 | 0.01 | 10 |
| 102 | 0.001 | 10 |
| 103 | 0.1 | 10 |
| 104 | 0.01 | *** |
| 105 | 1 | 10 |
| 106 | 1 | 1 |
| 107 | 1 | *** |
| 108 | 0.1 | 10 |
| 109 | 1 | 10 |
| 110 | 10 | *** |
| 111 | 0.001 | 10 |
| 112 | 0.0001 | *** |
| 113 | 0.0001 | *** |
| 114 | 0.01 | *** |
| 116 | 0.001 | 1 |
| 117 | 0.0001 | 1 |
| 120 | 0.0001 | 1 |
| 121 | 0.0001 | 10 |
| 122 | 0.0001 | 1 |
| 123 | 0.0001 | 10 |
| 127 | 0.0001 | 10 |
| 128 | 0.0001 | 1 |
| 131 | 0.0001 | 1 |
| 138 | 0.0001 | 10 |
| 148 | 0.0001 | 1 |
| 152 | 0.0001 | 10 |
| 154 | 0.001 | 10 |
| 158 | 0.0001 | 1 |
| 159 | 0.0001 | 0.1 |
| 160 | 0.001 | 1 |
| 161 | 0.01 | 10 |
| 184 | 0.0001 | 1 |
| 200 | 0.01 | 0.1 |
| 202 | 0.0001 | 1 |
| 203 | 0.0001 | 1 |
| 204 | 0.0001 | 1 |
| 205 | 0.0001 | 1 |
| 206 | 1 | *** |
| 207 | 0.001 | 1 |
| 208 | 0.0001 | 1 |
| 209 | 0.0001 | 0.1 |
| 210 | 0.0001 | 1 |
| 211 | 0.0001 | 1 |
| 212 | 0.0001 | 0.01 |
| 213 | 0.0001 | 1 |
| 214 | 0.01 | 10 |
| 215 | 0.01 | 1 |
| 217 | 1 | *** |
| 218 | 0.0001 | 1 |
| 220 | 0.0001 | 1 |
| 221 | 0.0001 | 1 |
| 224 | 0.0001 | 10 |
| 226 | 0.0001 | 0.1 |
| 227 | 0.001 | *** |
| 229 | 0.0001 | 0.1 |
| 230 | 0.0001 | 1 |
| 231 | 0.0001 | 1 |
| 232 | 0.12 | 1.11 |
| 233 | 0.37 | 1.11 |
| 234 | 1.11 | 1.11 |
| 235 | 0.04 | 1.11 |
| 236 | 0.01 | 0.12 |
| 237 | 0.37 | 0.04 |
| 238 | 0.04 | 0.37 |
| 239 | 0.01 | 1.11 |
| 240 | 0.37 | 3.33 |
| 241 | 0.12 | 1.11 |
| 242 | 0.01 | 0.01 |
| 243 | 0.01 | 0.01 |
| 244 | 0.01 | 0.01 |
| 245 | 3.33 | ** |
| 246 | 1.11 | 3.33 |
| 247 | 0.01 | 0.01 |
| 248 | 0.12 | 0.01 |
| 249 | 0.01 | 1.11 |
| 250 | 0.01 | 0.12 |
| 251 | 0.12 | 10 |
| 252 | 0.37 | 1.11 |
| 253 | 0.04 | 0.12 |
| 254 | 0.01 | 1.11 |
| 255 | 0.12 | 3.33 |
| 256 | 0.01 | 0.04 |
| 257 | 1.11 | 3.33 |
| 258 | 0.37 | 10 |
| 259 | 0.01 | 10 |
| 260 | 0.01 | 0.37 |
| 261 | ** | 10 |
| 262 | ** | 10 |
| 263 | 0.12 | ** |
| 264 | 1.11 | 1.11 |
| 265 | 0.01 | 0.04 |
| 267 | 0.01 | 0.12 |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. The compound N-{2-[4-amino-2-(ethoxymethyl)-1H-imidazo[4,5-c]quinolin-1-yl)-1,1-dimethylethyl}methanesulfonamide, or a pharmaceutically acceptable salt thereof.

2. A pharmaceutical composition comprising a therapeutically effective amount of a compound or salt of claim 1.

3. A method of inducing cytokine biosynthesis in an animal comprising administering an effective amount of a compound of claim 1 to the animal.

* * * * *

UNITED STATES PATENT AND TRADEMARK OFFICE
CERTIFICATE OF CORRECTION

PATENT NO.    : 6,677,349 B1
DATED         : January 13, 2004
INVENTOR(S)   : Griesgraber, George W.

It is certified that error appears in the above-identified patent and that said Letters Patent is hereby corrected as shown below:

Column 2,
Line 16, please delete "reponse" and insert -- response --, therefore.
Line 21, please delete "pharmaceutial" and insert -- pharmaceutical --, therefore.
Line 51, please delete "–$R_5$–" and insert -- –$NR_5$– --, therefore.
Line 63, please delete "heterocyclyt" and insert -- heterocyclyl -therefore.

Column 3,
Lines 8, 9, 10, 11, 12 and 13, please delete "–alkyl)$_{0-1}$" and insert -- –(alkyl)$_{0-1}$ --, therefore.
Line 14, please delete "-$R_3R_3$" and insert -- -$NR_3R_3$ --, therefore.
Lines 19 and 20, Please delete "-$R_3$–" and insert -- -$NR_3$– --, therefore.
Line 29, after "alkyl" insert -- , --.
Line 49, please delete "–$_3$;" and insert -- -$N_3$; --, therefore.

Column 4,
Line 18, please delete "Formnula" and insert -- Formula --, therefore.

Column 7,
Line 66, please delete "phannaceutically" and insert -- pharmaceutically --, therefore.

Column 9,
Line 46, please delete "step (I)" and insert -- step (1) --, therefore.

Column 13,
Line 29, please delete "pharmnaceutical" and insert -- pharmaceutical --, therefore.

Column 17,
Line 51, please delete "dichloromethanemethanol" and insert
-- dichloromethane/methanol --, therefore.
Line 55, please delete "dichloromethanediethyl" and insert -- dichloromethane/diethyl --, therefore.
Line 63, after "Hz" insert -- , --.

Column 18,
Line 32, please delete "dichloro\methanemethanol" and insert -- dichloromethane/methanol --, therefore.

Column 19,
Line 14, please delete "J'5.7" and insert -- J = 5.7 --, therefore.

UNITED STATES PATENT AND TRADEMARK OFFICE
CERTIFICATE OF CORRECTION

PATENT NO. : 6,677,349 B1
DATED : January 13, 2004
INVENTOR(S) : Griesgraber, George W.

It is certified that error appears in the above-identified patent and that said Letters Patent is hereby corrected as shown below:

Column 21,
Line 28, please delete "[4,5-clquinoline" and insert -- [4,5-c]quinoline --, therefore.

Column 22,
Line 55, please delete "dichloromethanemethanol" and insert
-- dichloromethane/methanol --, therefore.

Column 23,
Line 31, please delete "dichloromethanemethanol" and insert
-- dichloromethane/methanol --, therefore.

Column 27,
Line 13, please delete "11.1" and insert -- 1.1 --, therefore.

Column 28,
Line 3, please delete "confirmn" and insert -- confirm --, therefore.

Column 124,
Line 60, please delete "vide" and insert -- vacuum to provide --, therefore.
Line 61, after "1H-" insert -- imidazo[4,5-c] --.
Line 64, please delete "trahydroimidazoquinoline" and insert
-- tetrahydroimidazoquinoline --, therefore.

Column 131,
Line 5, please delete "Trifluoroacetat" and insert -- Trifluoroacetate --, therefore.
Line 29, after "butyl]" insert -- -N --.
Line 57, please delete "lodomethane" and insert -- Iodomethane --, therefore.

Column 132,
Line 17, after "butyl]-" insert -- N- --.
Line 65, after "by" insert -- LC- --.
Line 67, please delete "triflroacetate" and insert -- trifluoroacetate --, therefore.

Column 149,
Line 22, please delete "choride" and insert -- chloride --, therefore.

Column 150,
Line 1, please delete "didhloromethane" and insert -- dichloromethane --, therefore.
Line 13, please delete "methoxyetyl" and insert -- methoxyethyl --, therefore.
Line 63, please delete "(m, 2)" and insert -- (m, 2H) --, therefore.

UNITED STATES PATENT AND TRADEMARK OFFICE
CERTIFICATE OF CORRECTION

PATENT NO. : 6,677,349 B1
DATED : January 13, 2004
INVENTOR(S) : Griesgraber, George W.

It is certified that error appears in the above-identified patent and that said Letters Patent is hereby corrected as shown below:

Column 154,
Example 250, Chemical Structure on lines 13-28, please delete:

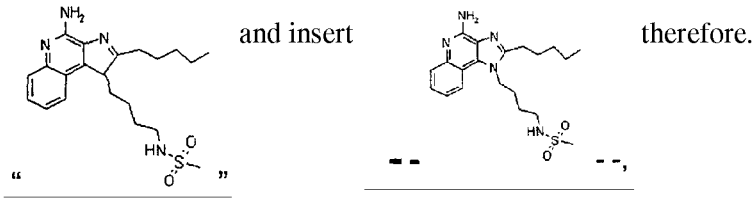

Example 251, Chemical Structure on lines 42-59, please delete:

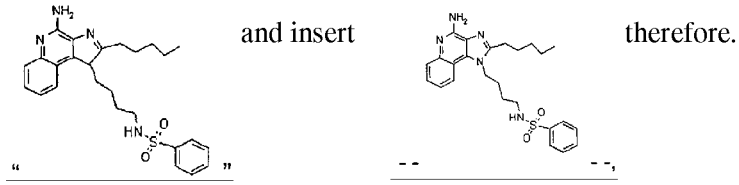

Column 155,
Line 29, please delete "nmmol" and insert -- mmol --, therefore.

Column 163,
Line 20, after "3.12" insert -- (m, 6H), 2.93 --.
Line 52, please delete "choride" and insert -- chloride --, therefore.

Column 164,
Line 65, please delete "concetrated" and insert -- concentrated --, therefore.
Line 67, please delete "ethoxymethy" and insert -- ethoxymethyl --, therefore.

UNITED STATES PATENT AND TRADEMARK OFFICE
CERTIFICATE OF CORRECTION

PATENT NO. : 6,677,349 B1
DATED : January 13, 2004
INVENTOR(S) : Griesgraber, George W.

It is certified that error appears in the above-identified patent and that said Letters Patent is hereby corrected as shown below:

Column 165,
Line 4, please delete "ethoxymethy" and insert -- ethoxymethyl --, therefore.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,677,349 B1
DATED : January 13, 2004
INVENTOR(S) : Griesgraber, George W.

It is certified that error appears in the above-identified patent and that said Letters Patent is hereby corrected as shown below:

Column 170,
Line 57, delete "quinolin-1-yl)-1", insert in place thereof -- quinolin-1-yl]-1 --.

Signed and Sealed this

Eighteenth Day of January, 2005

JON W. DUDAS
*Director of the United States Patent and Trademark Office*